United States Patent
de Figueiredo et al.

(10) Patent No.: US 9,340,768 B2
(45) Date of Patent: May 17, 2016

(54) TRANSFORMATION OF GLYCEROL AND CELLULOSIC MATERIALS INTO HIGH ENERGY FUELS

(75) Inventors: Paul de Figueiredo, College Station, TX (US); Lei Li, College Station, TX (US); Zivko Nikolov, College Station, TX (US); Brian D. Shaw, College Station, TX (US); Martin B. Dickman, College Station, TX (US); Eliezer S. Louzada, McAllen, TX (US); Joseph M. Sturino, College Station, TX (US); Ying-Ying Chang, Taipei (TW)

(73) Assignee: THE TEXAS A&M UNIVERSITY SYSTEM, College Station, TX (US)

( * ) Notice: Subject to any disclaimer, the term of this patent is extended or adjusted under 35 U.S.C. 154(b) by 592 days.

(21) Appl. No.: 13/003,931

(22) PCT Filed: Jul. 16, 2009

(86) PCT No.: PCT/US2009/050905
§ 371 (c)(1),
(2), (4) Date: Sep. 26, 2011

(87) PCT Pub. No.: WO2010/009348
PCT Pub. Date: Jan. 21, 2010

(65) Prior Publication Data
US 2012/0115193 A1    May 10, 2012

Related U.S. Application Data

(60) Provisional application No. 61/081,275, filed on Jul. 16, 2008.

(51) Int. Cl.
*C12N 1/22* (2006.01)
*C12N 1/32* (2006.01)
(Continued)

(52) U.S. Cl.
CPC .. *C12N 1/22* (2013.01); *C12N 1/32* (2013.01); *C12N 9/1205* (2013.01); *C12P 5/00* (2013.01); *C12P 5/02* (2013.01); *C12P 7/6409* (2013.01); *C12P 7/649* (2013.01); *C12P 7/6463* (2013.01); *Y02E 50/13* (2013.01); *Y02P 20/52* (2015.11)

(58) Field of Classification Search
None
See application file for complete search history.

(56) References Cited

U.S. PATENT DOCUMENTS

| 4,220,720 A | 9/1980 | Taoka et al. |
| 4,461,648 A * | 7/1984 | Foody .......................... 127/37 |

(Continued)

FOREIGN PATENT DOCUMENTS

| EP | 0207475 B1 | 9/1992 |
| WO | 2007120801 A2 | 10/2007 |

(Continued)

OTHER PUBLICATIONS

Fierro-Monti et al., Differential Expression of Clostridium acetobutylicum Antisense RNA: Implications for Regulation of Glutamine Synthetase., Journal of Bacteriology (1992), vol. 1992, pp. 7642-7647.*

(Continued)

*Primary Examiner* — Alexander Kim
(74) *Attorney, Agent, or Firm* — Edwin S. Flores; Daniel J. Chalker; Chalker Flores, LLP

(57) ABSTRACT

The present invention includes a system and method for making a biofuel comprising: providing a nitrogen-limiting, minimal growth media comprising glycerol, sugars generated from cellulosic biomass or both, under conditions in which an oleaginous microbe converts the growth media into at least one of triacylglycerol, neutral lipids, fatty acids, long-chain fatty acids, and hydrocarbons that is secreted by the microbe.

20 Claims, 38 Drawing Sheets

(51) Int. Cl.
  *C12N 9/12* (2006.01)
  *C12P 5/00* (2006.01)
  *C12P 5/02* (2006.01)
  *C12P 7/64* (2006.01)

(56) References Cited

U.S. PATENT DOCUMENTS

| | | | |
|---|---|---|---|
| 5,697,986 | A | 12/1997 | Haas |
| 6,803,218 | B1 | 10/2004 | Seyfried et al. |
| 7,135,309 | B1 | 11/2006 | Laffend et al. |
| 7,169,588 | B2 | 1/2007 | Burch et al. |
| 7,285,403 | B2 | 10/2007 | Jeffries et al. |
| 7,371,558 | B2 | 5/2008 | Cervin et al. |
| 7,691,159 | B2 | 4/2010 | Li |
| 7,854,774 | B2 | 12/2010 | Renninger et al. |
| 7,905,930 | B2 | 3/2011 | Oyler |
| 2002/0069987 | A1* | 6/2002 | Pye ................................ 162/77 |
| 2006/0236595 | A1 | 10/2006 | Nakamura |
| 2007/0054385 | A1* | 3/2007 | Yadav et al. ................ 435/134 |

FOREIGN PATENT DOCUMENTS

| | | |
|---|---|---|
| WO | 2008006037 A2 | 1/2008 |
| WO | 2010009348 A2 | 1/2010 |

OTHER PUBLICATIONS

Horne et al., Secretion of lipids induced by inhibition of peptidoglycan synthesis in streptococci., Journal of Bacteriology (1977), vol. 132(2), pp. 704-717.*
Breuer et al., Debaryomyces hansenii—an extremophilic yeast with biotechnological potential., Yeast (2006), vol. 23, pp. 415-437.*
Q6BT31 (last viewed on Dec. 17, 2013).*
Ma et al., Overexpression of autophagy-related genes inhibits yeast filamentous growth, Autophagy (2007), vol. 3(6), pp. 604-609.*
Cebollero et al., Induction of Autophagy by Second-Fermentation Yeasts during Elaboration of Sparkling Wines, Applied and Environmental Microbiology (2006), vol. 72, pp. 4121-4127.*
Gori et al., Proteomic changes in Debaryomyces hansenii upon exposure to NaCl stress., FEMS Yeast Research (2006), vol. 7, pp. 293-303.*
Merdinger et al., Lipids of Debaryomyces hansenii, Journal of Bacteriology (1965), vol. 89(6), pp. 1488-1493.*
Suzuki et al., Interrelationship among Atg proteins during autophagy in *Saccharomyces cerevisiae*., Yeast (2004), vol. 21, pp. 1057-1065.*
Papanikolaou et al., Single cell oil production by *Yarrowia lipolytica* growing on an industrial derivative of animal fat in batch cultures., Applied Microbiology and Biotechnology (Mar. 2002), vol. 58, Issue 3, pp. 308-312.*
Papanikolaou et al., Single cell oil (SCO) production by *Mortierella isabellina* grown on high-sugar content media., Bioresource Technology (2004), vol. 95, pp. 287-291.*
Holdsworth et al., Triacylglycerol Synthesis in the Oleaginous Yeast Candida curvata D, Lipids (1991), vol. 26, pp. 111-118.*
Iassonova, Diliara., Lipid synthesis and encapsulation by Cryptococcus curvatus (2009), Iowa State Univerity Graduate Theses and Dissertations, pp. 1-106.*
Chen et al., Fermentation of Sugarcane Bagasse Hemicellulose Hydrolysate to Xylitol by a Hydrolysate-Acclimatized Yeast., Journal of Food Science (1985), vol. 50, Issue 1, pp. 226-228.*
Gill et al., Lipid accumulation in an oleaginous yeast (Candida 107) growing on glucose in single-stage continuous culture., Appl Environ Microbiol. Feb. 1977; 33(2): 231-239.*
Korean Intellecutal Property Office (ISA), International Search Report and Written Opinion for PCT/US2009/050905 dated Mar. 15, 2010, 11 pp.
European Patent Office, Extended European Search Report for Application No. 09798773.9 dated Dec. 7, 2011. 14 pp.

Adler, et al. "Glycerol Metabolism and Osmoregulation in the Salt-Tolerant Yeast Debaryomyces hansenii" Journal of Bacteriology, Apr. 1985, pp. 300-306.
Alvers, et al., Autophagy is required for extension of yeast chronological life span by rapamycin. Autophagy 5:6, 1-3; Aug. 2009.
Breuer, et al., "Debaryomyces hansenii—an extremophilic yeast with biotechnological potential" Yeast 2006, 23, 415-437.
Butinar, et al., "Yeast diversity in hypersaline habitats" FEMS Microbiol Lett, Feb. 3, 2005, 244, 229-234.
Charles, et al., "Public policy and biofuels: The way forward?" Energy Policy 2007, 35, 5737-5746.
Chen, et al., "Autophagy is Enhanced and Floral Development is Impaired in AtHVA22d RNA Interference Arabidopsis" Plant Physiol, Apr. 2009, vol. 149, 1679-1689.
Chisti, Y., "Biodiesel from microalgae" Biotechnol Advances, Feb. 13, 2007, 25, 294-306.
Coleman, et al., "Enzymes of triacylglycerol synthesis and their regulation" Progress in Lipid Research 2004, 43, 134-176.
Dai, et al., "Biodiesel generation from oleaginous yeast *Rhodotorula glutinis* with xylose assimilating capacity" African Journal of Biotechnology, Sep. 19, 2007, 6, 2130-2134.
Dharmadi, et al., "Anaerobic Fermentation of Glycerol by *Escherichia coli*: A New Platform for Metabolic Engineering" Biotechnol Bioeng, May 20, 2006, 94, 821-829.
Fujimoto, et al., "Lipid droplets: a classic organelle with new outfits" Histochem Cell Biol 2008, 130: 263-279.
Gangar, et al., "Alteration in the cytosolic triacylglycerol biosynthetic machinery leads to decreased cell growth and triacylglycerol synthesis in oleaginous yeast" Biochemical Journal 2002, 365, 577-589.
Goodman, Joel M., "The Gregarious Lipid Droplet" J Biol Chem, Oct. 17, 2008, vol. 283, 28005-28009.
Granger, et al., "Efficiency of Fatty-Acid Synthesis by Oleaginous Yeasts—Prediction of Yield and Fatty-Acid Cell Content from Consumed C/N Ratio by a Simple Method" Biotechnology and Bioengineering 1993, 42, 1151-1156.
Greenberg, et al. "Many Roads Lead to the Lipid Droplet" Cell Metabolism, Jun. 7, 2008, 472-473.
Homann, et al. "Harnessing Natural Diversity to Probe Metabolic Pathways" PLoS Genetics, Dec. 2005, 1:715-729.
Kourtis, et al. "Autophagy and cell death in model organisms" Cell Death and Differentiation (2009) 16, 21-30.
Li, et al. "The Yeast Lysosome-like Vacuole: Endpoint and Crossroads" Biochim Biophys Acta 2009, 1793(4), 650-663.
Longatti, et al., "Vesicular trafficking and autophagosome formation" Cell Death Differ 2009, 16, 956-965.
Mabee, W. E., Policy Options to Support Biofuel Production. Adv Biochem Engin/ Biotechnol, Apr. 11, 2007, 108, 329-357.
Merdinger, et al., "Lipids of Debaryomyces hansenii" Journal of Bacteriology, Jun. 1965, vol. 89, 1488-1493.
Murarka, et al., "Fermentative Utilization of Glycerol by *Escherichia coli* and its Implications for the Production of Fuels and Chemicals" Appl Environ Microbiol, Feb. 2008, vol. 74, No. 4, 1124-1135.
Nedvetsky, et al., "Regulation of Aquaporin-2 Trafficking" Handb Exp Pharmacol 190, 2009, 133-157.
Pan, et al. "Biomass Yields and Energetic Yields of Oleaginous Yeasts in Batch Culture" Biotechnology and Bioengineering, vol. XVIII, 1986, 112-114.
Pollack, et al., "Autophagy in filamentous fungi" Fungal Genet Biol, 2009, 46, 1-8.
Prista, et al., "Mechanisms underlying the halotolerant way of Debaryomyces hansenii" FEMS Yeast Res 2005, 5, 693-701.
Schu, et al. "Phosphatidylinositol 3-Kinase Encoded by Yeast VPS34 Gene Essential for Protein Sorting" Science, vol. 260, Apr. 2, 1993.
Suzuki, et al. "Molecular machinery of autophagosome formation in yeast, *Saccharomyces cerevisiae*" FEBS Letters 581 (2007), 2156-2161.
Thiele, et al., "Cell biology of lipid droplets" Curr Opin Cell Biol, Jul. 5, 2008, 20, 378-385.

(56) References Cited

OTHER PUBLICATIONS

Wang, et al., "Glycerol production by microbial fermentation: A review" Biotechnol Adv 2001, 19, 201-223.

Wynn, et al., "Biochemical events leading to the diversion of carbon into storage lipids in the oleaginous fungi Mucor circinelloides and Mortierella alpina" Microbiology 2001, 147, 2857-2864.

Jarvis, et al. "Formate and ethanol are the major products of glycerol fermentation produced by a Klebsiella planticola strain isolated from red deer" Journal of Applied Microbiology 1997, 83, 166-174.

Biebel, H. "Fermentation of glycerol by Clostridium pasteurianum—batch and continuous culture studies" Journal of Industrial Microbiology & Biotechnology (2001) 27, 18-26.

European Patent Office "Communication pursuant to Article 94(3) EPC" for European Regional Patent Appl. No. 09 798 773.9 dated Dec. 11, 2014, 6 pp.

Dai, et al. "Biodiesel generation from oleaginous yeast Rhodotorula glutinis with xylose assimilating capacity" African Journal of Biotechnology, vol. 6 (18), pp. 2130-2134, Sep. 19, 2007.

* cited by examiner

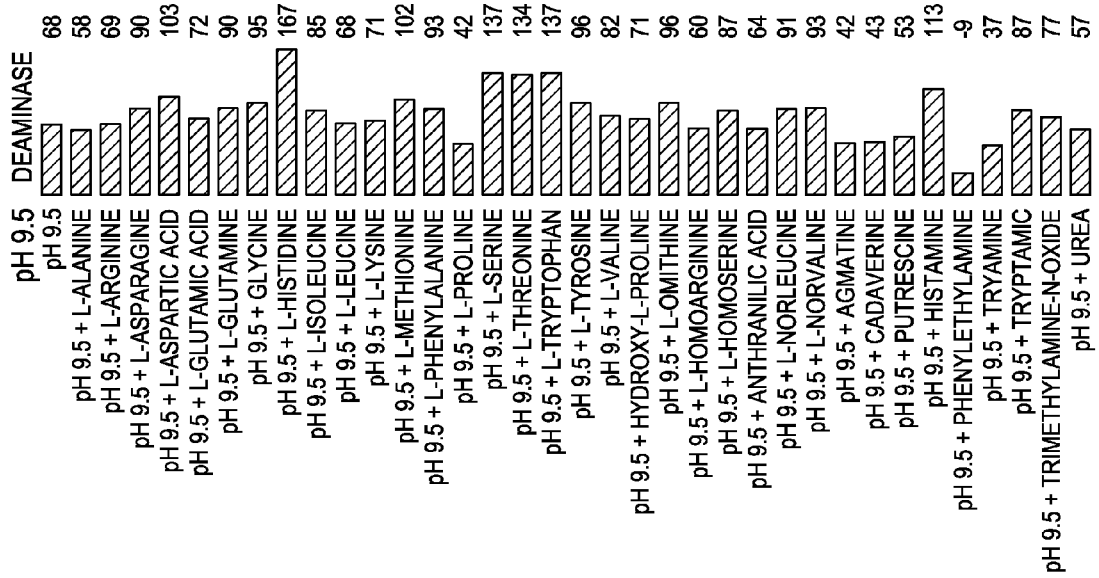
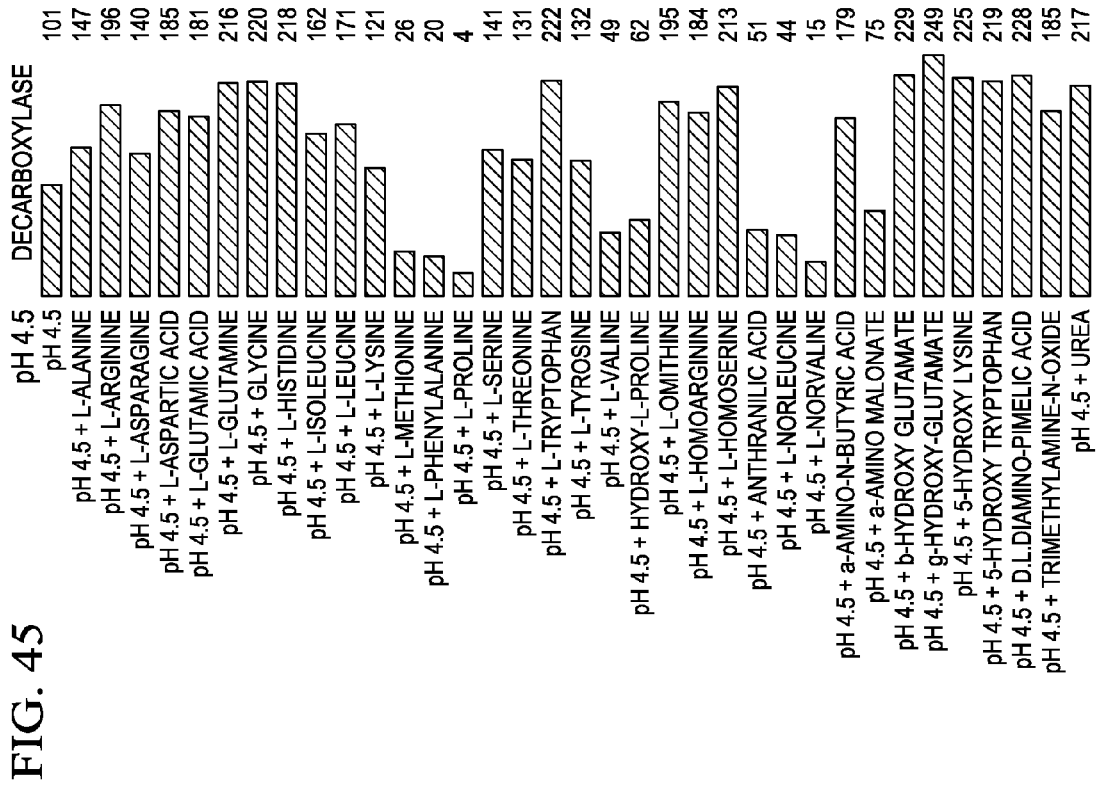
FIG. 45

TRANSFORMATION OF GLYCEROL AND CELLULOSIC MATERIALS INTO HIGH ENERGY FUELS

CROSS-REFERENCE TO RELATED APPLICATIONS

This application is a National Stage of International Application No. PCT/US2009/050905 filed on Jul. 16, 2009, which claims the benefit of U.S. Provisional Patent Application Ser. No. 61/081,275 filed on Jul. 16, 2008.

TECHNICAL FIELD OF THE INVENTION

The present invention relates in general to the field of biofuels, and more particularly, to the conversion of short chain carbohydrates from biofuel formation and cellulosic biomass into high energy fuels.

BACKGROUND OF THE INVENTION

Without limiting the scope of the invention, its background is described in connection with biofuel formation.

A number of investigators have been developing alternative fuels to partially or completely replace fossil fuels. As proven reserves of fossil fuel reservoirs decrease, a great need has arisen for the development of fuels based on renewable sources.

One such renewable source of energy is taught in U.S. Pat. No. 7,371,558, issued to Cervin, et al. for a process on the biological production of 1,3-propanediol with high yield. Briefly, a microorganism useful for biologically producing 1,3-propanediol from a fermentable carbon source at higher yield is taught. Cofactor complexity required the use of whole cell catalyst for an industrial process to produce 1,3-propanediol. A microorganism is included with disruptions in specified genes and alterations in the expression levels of specified genes that is useful in a higher yielding process to produce 1,3-propanediol.

U.S. Pat. No. 7,285,403, issued to Jeffries, et al., teaches a xylose-fermenting recombinant yeast strain. Briefly, xylose-fermenting recombinant yeast strains are taught that express xylose reductase, xylitol dehydrogenase, and xylulokinase and have reduced expression of PHO13 or a PHO13 ortholog, as well as methods of fermenting xylose to obtain ethanol using the recombinant yeast strains. One specific embodiment of the invention is a recombinant xylose-fermenting strain of *Saccharomyces cerevisiae* expressing Pichiastipis XYL123 and having a transposon or disruption mutation in PHO13.

Another such renewable source is taught in U.S. Pat. No. 5,697,986, issued to Haas, for fuels as solvents for the conduct of enzymatic reactions. Briefly, this patent describes a method of producing biofuels by carrying out the enzymatic transesterification of fatty acid-containing materials directly in automotive fuels. The method includes forming a reaction mixture of automotive or related fuel, fatty acid-containing substances, alcohol and lipase, all in amounts effective for a reaction to occur, and water in an amount sufficient to confer enzymatic activity, incubating the reaction mixture for a time and at a temperature sufficient for transesterification between the fatty acid-containing substance and the alcohol to occur, and separating the by-products from the biofuel portion of the mixture.

Yet another method is taught in United States Patent Application No. 20080092829, filed by Renninger, et al., for fuel components, fuel compositions and methods of making and using same that includes a fuel composition with at least a $C_5$ isoprenoid compound or its derivative and a conventional fuel additive. The $C_5$ isoprenoid compound or its derivative can be used as a fuel component or as a fuel additive in the fuel composition. The fuel composition may further be a conventional fuel component selected from a diesel fuel, jet fuel, kerosene or gasoline. Methods of making and using the fuel composition are also disclosed.

Another method is taught in United States Patent Application No. 20080071125, filed by Li for a method of converting triglycerides to biofuels. Briefly, the application discloses a triglyceride-to-fuel conversion process that includes the steps of (a) pre-conditioning unsaturated triglycerides by catalytic conjugation, cyclization, and cross-link steps; (b) contacting the modified triglycerides with hot-compressed water containing a catalyst, wherein cracking, hydrolysis, decarboxylation, dehydration, aromatization, or isomerization, or any combination thereof, of the modified triglycerides produce a crude hydrocarbon oil and an aqueous phase containing glycerol and lower molecular weight molecules, and (c) refining the crude hydrocarbon oil to produce various grades of biofuels. The biofuel composition may include straight-chain, branched and cycloparaffins, and aromatics. The paraffins are derived from conversion of triglycerides and the aromatics are derived from conversion of either triglycerides, petroleum, or coal.

United States Patent Application No. 20060236595, filed by Nakamura teaches a biofuel conversion process. Briefly, a process, method, apparatus and materials for efficient conversion of waste vegetable oils into biofuel that does not use methanol as a reactant or catalyst is disclosed. The biofuel is mixed with kerosene or heavy oil to form a stable diesel fuel grade fuel that is mixable with diesel fuel. In addition, the process and apparatus are also applicable to the conversion of virgin vegetable oils and other waste or virgin oils, such as used motor oil, into fuels or fuel additives.

SUMMARY OF THE INVENTION

The present invention includes systems and methods for the conversion of short-chain carbohydrates from biofuel formation and cellulosic biomass into high-energy fuels.

In one embodiment, the present invention includes compositions, cells and methods of making a biofuel comprising: providing a nitrogen-limiting, minimal growth media comprising glycerol, sugars generated from cellulosic biomass or both, under conditions in which an oleaginous microbe converts the growth media into at least one of triacylglycerol, neutral lipids, fatty acids, long-chain fatty acids, and hydrocarbons that is secreted by the microbe. In one aspect, the media comprise 0.5, 1.0, 1.5, or 2.0 M salt. In another aspect, the media comprise at least one of a cellulose, a cellulosic substrate, cellobiose, carboxymethylcellulose, hemicellulose, a sweet sorghum extract, a sugar cane extract, a sugar cane baggasse, or cellulosic substrates derived therefrom. In another aspect, the neutral lipid is at least one of a triacylglycerol (TAG) comprising saturated esterified fatty acids; a TAG comprising unsaturated esterified fatty acids; a TAG comprising oleic acid; or a TAG comprising oleic acid at the Sn-1, Sn-2 or Sn-3 position. In another aspect, the hydrocarbons comprise C16, C18, C20, C22, C24, C26, C28, C30, and/or C40 and the hydrocarbons are further processed into a lubricant, biodiesel, gasoline, jet fuel, or a liquid transportation fuel. In another aspect, the hydrocarbons contain C15, C17, C19, C21, C23, C25, C27, C29, and/or C31.

In yet another aspect, the mixture of hydrocarbons is optimized for a specific application, selected from a precursor for liquid transportation fuel biosynthesis, a precursor for lubricant biosynthesis or derivatives thereof. In another aspect, the microbes are grown for 48, 72, 96, or 120 hours at a temperature of 25° C., 30° C., or 37° C. and at a pH of 5.0, 5.5, 6.0, 6.5, 7.0 or 7.5. In another aspect, the media comprise 0.01% nitrogen. In another aspect, the microbes secrete the triacylglycerol, neutral lipids, fatty acids, long-chain fatty acids, and hydrocarbons without cell death. In another aspect, the microbes are induced to overexpress one or more autophagy-associated genes. In another aspect, the microbes are induced to overexpress one or more autophagy-associated genes selected from ATG1, ATG2, ATG3, ATG4, ATG5, ATG6, ATG7, ATG8, ATG9, ATG10, ATG11, ATG12, ATG13, ATG14, ATG15, ATG16, ATG17, ATG18, ATG19, ATG20, ATG21, ATG22, ATG23, ATG24, ATG25, ATG26, ATG27, ATG28, ATG29, ATG30, ATG31. In another aspect, the microbes are genetically modified to overexpress one or more autophagy-associated S. cerevisiae genes selected from ATG1, ATG2, ATG3, ATG4, ATG5, ATG6, ATG7, ATG8, ATG9, ATG10, ATG11, ATG12, ATG13, ATG14, ATG15, ATG16, ATG17, ATG18, ATG19, ATG20, ATG21, ATG22, ATG23, ATG24, ATG25, ATG26, ATG27, ATG28, ATG29, ATG30, ATG31. In another aspect, the microbes are genetically modified to overexpress one or more autophagy-associated genes that are orthologous or paralogous to a gene selected from ATG1, ATG2, ATG3, ATG4, ATG5, ATG6, ATG7, ATG8, ATG9, ATG10, ATG11, ATG12, ATG13, ATG14, ATG15, ATG16, ATG17, ATG18, ATG19, ATG20, ATG21, ATG22, ATG23, ATG24, ATG25, ATG26, ATG27, ATG28, ATG29, ATG30, ATG31. In yet another aspect, the microbes are genetically modified to overexpress one or more autophagy-associated genes integrated into the genome or on an autonomously replicating plasmid. In another aspect, the microbes are selected from *Debaryomyces* sp., *Saccharomyces* sp., *Rhodococcus* sp., *Nocardia* sp., *Mycobacterium* sp., *Rhodosporidium* sp., *Cryptococcus* sp., *Rhodotorula* sp., *Yarrowia lipolytica* and/or *Lipomyces* sp. In another aspect, combinations of these microbes are used in a single reaction vessel.

Another embodiment of the present invention includes a method of producing a biofuel comprising: growing an oleaginous microbe in a nitrogen-limiting, minimal media to late log phase and/or stationary phase, whereby the oleaginous microbe secretes an oil. In one aspect, the media comprise 0.01% nitrogen. In another aspect, the microbes are grown for 48, 72, 96, or 120 hours at a temperature of 25° C., 30° C., or 37° C. and at a pH of 5.0, 5.5, 6.0, 6.5, 7.0 or 7.5. In another aspect, the media comprise 0.5, 1.0, 1.5, or 2.0 M salt, e.g., at least one of NaCl, KCl, or both KCl and NaCl. In another aspect, the microbes are treated with an agent that increases PI-3 kinase activity. In another aspect, the microbes have been genetically modified to overexpress PI-3 kinase. In another aspect, the microbes have been genetically modified to comprise a PI-3 kinase overexpression cassette into the cell, wherein the PI-3 kinase overexpression cassette is integrated into the genome or the PI-3 kinase is in an overexpression cassette on an autonomously replicating plasmid.

Yet another embodiment of the present invention includes an oleaginous microbe comprising that has been engineered to secrete enhanced amounts of oil by upregulating PI-3 kinase activity. In one aspect, the microbes have been genetically modified to overexpress PI-3 kinase. In one aspect, the microbes have been genetically modified to comprise a PI-3 kinase overexpression cassette into the cell, wherein the PI3-kinase overexpression cassette is integrated into the genome or the PI-3 kinase is in an overexpression cassette on an autonomously replicating plasmid. In another aspect, the microbes are selected from wherein the organism used for biofuel formation are selected from *Debaryomyces* sp., *Saccharomyces* sp., *Rhodococcus* sp., *Nocardia* sp., *Mycobacterium* sp., *Rhodosporidium* sp., *Cryptococcus* sp., *Rhodotorula* sp., *Yarrowia lipolytica* and/or *Lipomyces* sp.

Yet another embodiment of the present invention includes an oleaginous microbe comprising that has been engineered to secrete enhanced amounts of oil by modulating the expression of autophagy-associated genes. In one aspect, the microbes are induced to modify the expression of one or more autophagy-associated *S. cerevisiae* genes selected from ATG1, ATG2, ATG3, ATG4, ATG5, ATG6, ATG7, ATG8, ATG9, ATG10, ATG11, ATG12, ATG13, ATG14, ATG15, ATG16, ATG17, ATG18, ATG19, ATG20, ATG21, ATG22, ATG23, ATG24, ATG25, ATG26, ATG27, ATG28, ATG29, ATG30, ATG31. In another aspect, the microbes are induced to modify the expression of one or more autophagy-associated genes that are orthologous or paralogous to the *S. cerevisiae* genes selected from ATG1, ATG2, ATG3, ATG4, ATG5, ATG6, ATG7, ATG8, ATG9, ATG10, ATG11, ATG12, ATG13, ATG14, ATG15, ATG16, ATG17, ATG18, ATG19, ATG20, ATG21, ATG22, ATG23, ATG24, ATG25, ATG26, ATG27, ATG28, ATG29, ATG30, ATG31. In another aspect, the microbes are genetically modified to vary the expression of one or more autophagy-associated genes selected from ATG1, ATG2, ATG3, ATG4, ATG5, ATG6, ATG7, ATG8, ATG9, ATG10, ATG11, ATG12, ATG13, ATG14, ATG15, ATG16, ATG17, ATG18, ATG19, ATG20, ATG21, ATG22, ATG23, ATG24, ATG25, ATG26, ATG27, ATG28, ATG29, ATG30, ATG31. In another aspect, the microbes are genetically modified to vary the expression of one or more autophagy-associated genes by integrating the genes into the genome, by expression of the genes on an autonomously replicating plasmid or by modifying the expression of the genes post-translationally. In another aspect, the microbes are engineered to under-express the autophagy-associated genes to decrease oil secretion. In another aspect, the microbes are engineered to overexpress the autophagy-associated genes to increase oil secretion. In another aspect, the microbes are further genetically modified to overexpress PI-3 kinase.

Yet another embodiment of the present invention is a method of reducing bioreactor waste comprising: mixing a reaction waste product comprising glycerol with a growth media and an inoculum of *Debaryomyces hansenii* under conditions in which *D. hansenii* converts the glycerol into long-chain fatty acids and hydrocarbons; and recovering the long-chain fatty acids and hydrocarbons produced thereby.

Yet another embodiment of the present invention is a method of reducing bioreactor waste comprising: generating a biofuel by fermentation; collecting a glycerol waste stream from the fermentation; mixing a biofuel reactor waste product comprising glycerol with a growth media and an inoculum of *D. hansenii* under conditions in which *D. hansenii* converts the glycerol into long-chain fatty acids and hydrocarbons; and recovering the long-chain fatty acids and hydrocarbons produced thereby.

Yet another embodiment of the present invention is a biofuel reactor comprising: a vessel comprising an internal volume capable of holding a growth medium; a microbe capable of converting glycerol into a long-chain fatty acids and hydrocarbons in the growth medium; and a source of glycerol.

BRIEF DESCRIPTION OF THE DRAWINGS

For a more complete understanding of the features and advantages of the present invention, reference is now made to the detailed description of the invention along with the accompanying figures and in which:

FIG. 45. Growth of *D. hansenii* at various pH values (as measured using the OMNILOG PM).

DETAILED DESCRIPTION OF THE INVENTION

Figure 1:
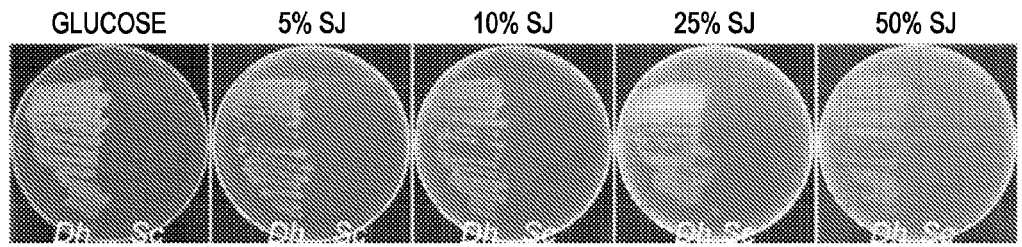
FIG. 1. Growth of *D. hansenii* on sugarcane juice.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the terms "tolerant" and "greater tolerance" refer to the ability of a cell or organism to survive and grow better in a given environmental condition better than a reference cell or organism. Typically in the present invention, the reference cell or organism is a wild type cell or organism, or a cell or organism that is isogenic except for a specified genetic difference.

As used herein, the term "salt tolerance" refers to the tolerance of an organism to elevated levels of dissolved salts, e.g., NaCl and/or osmolytes, e.g., glycerol, but can also include tolerance to elevated levels of other dissolved salts, e.g., potassium, calcium, and magnesium salts or osmolytes.

As used herein, the term "culturing" refers to a process of growing cells or organisms under conditions that allow increase in size and/or number of cells or organisms, or that are intended to test for such increase in size and/or number. For example, culture includes growth of yeast cells in liquid or solid media culture, as well as growth of plants in soil. Thus, culturing is distinguished from mere storage of cells or organisms.

As used herein, the term "cell culture" refers to culture of cells as distinguished from culturing multicellular organisms, such as plants. That is, the cells are present as generally separated cells without organization into natural complex structures such as tissues. Commonly, cell culture is carried out with liquid media, with the cells either on a surface or surfaces and bathed by the media, or suspended in the media.

As used herein, the phrase "high salt conditions" refers to the presence of salt and other osmolytes, e.g., sodium chloride (or sodium ion), carbohydrates and glycerol in solution or in position to become solubilized at a concentration higher than normal for a particular cell type or organisms of interest, e.g., to eliminate or prevent the growth of unwanted organisms. For example, increasing the salt concentration of a bioreactor or fermentor waste stream that includes fermenting bacteria or yeasts can be used to eliminate or prevent the continued growth of those organisms, while permitting the halophilic yeast of the present invention to convert glycerol and cellulosic materials into long-chain hydrocarbons with little or no interference from other fermenting bacteria or yeast.

As used herein, the phrase "growth conditions" refers to conditions that allow growth, preferably including increase in numbers, of a reference cell or organism such as *Debaryomyces hansenii*.

As used herein, the phrase "exponential growth phase" refers to the period of growth of cells (e.g., yeasts) in non-replenished medium during which active growth occurs. When number of cells is plotted in a semi-log plot versus time, the exponential growth phase is shown as a generally linear section of the curve, typically between an upward curving initial growth period (generally representing a lag phase and induction of growth) and a later portion of the curve where the slope decreases as growth in the number of cells substantially slows and usually essentially stops (stationary phase).

As used herein, the phrases "stationary growth phase" or "stationary phase" refer to the period in growth of cells in non-replenished medium during which the increase in the number of cells substantially slows and typically stops. Cells can also be maintained in exponential growth phase in continuous culture, e.g., by replenishment of media and removal of cells.

As used herein, the phrase "increased yield" refers to a culture that produces a greater amount of the product than a reference culture, or a greater amount in a specified time period. The increase may, for example, be due to the presence of a greater density (number) of cells in a particular volume of culture.

As used herein, the term "fermentation" refers to a metabolic process (and the associated culture process) that is not principally a respiration process. Thus, fermentation is a generally anaerobic process.

As used herein, the term "liquid culture" refers to a culture of cells or organisms that is carried out with the cells or organisms primarily suspended in a liquid growth medium.

As used herein, the term "lipid" refers insoluble compounds that are soluble in nonpolar (e.g., chloroform and benzene) solvents.

As used herein, the term "hydrocarbon" refers to a particular class of lipids, with particular emphasis on the aliphatic hydrocarbons, such as n-alkanes and n-alkenes. It should also be noted that n-alkanes tend to be odd-numbered as they result from enzymatic decarboxylation of fatty acids.

As used herein, the term "fatty acid" refers to compounds the building blocks of lipids and exist in free forms (e.g., free fatty acids), bound forms (e.g., through ester linkages in lipid classes such as wax esters, triacylglycerols, and phospholipids), and in combination with other biochemical classes such as glycolipids (macromolecules formed by combination of lipids with carbohydrates) and lipoproteins (macromolecules formed by the combination of lipids with proteins). As used herein, the term fatty acids includes even-chain, odd-chain or combinations of both even- and odd-chain fatty acids.

As used herein, the term "n-alkanols" (fatty alcohols) are a type of lipid synthesized by enzymatic reduction of fatty acids.

As used herein, the term "neutral lipids" are defined as (lipid weight)/(cell dry weight) produced by the organism under defined conditions.

As used herein, the term "secretion" refers to a process whereby a biological molecule is transported from the inside of the cell to the outside of the cell via a process that does not involve concomitant cell death.

As used herein, the term "lipid body secretion" refers to a process whereby lipid bodies are secreted.

As used herein, the term "lipid body" also referred to as "oil body" is a subcellular organelle that is enriched in lipids and/or biological oils. Lipid bodies can be enriched in particular kinds of lipids, including, but not limited to triacylglycerols. It should be noted that lipid bodies may comprise inorganic molecules, protein, small organic molecules, ions, and other biological biologicals associated with them.

While the present invention includes, as an example, a biofuel made by *D. hansenii*, other oleaginous yeast and oleaginous bacteria may be used with the present invention. Examples of oleaginous yeast that may be used with the present invention include, but are not limited to: *Yarrowia, Candida, Rhodotorula, Rhodosporidium, Cryptococcus, Trichosporon* and *Lipomyces*. Other examples of oil-synthesizing yeast include: *Rhodosporidium toruloides, Lipomyces starkeyii, Lipomyces lipoferus, Candida revkaufi, Candida pulcherrima, Candida tropicalis, Candida utilis, Candida valida, Candida utilis, Codermyces poitrasii, Cryptococcus curvatus, Cryptococcus albidus, Pichia angusta, Trichosporon pullans, Trichosporon cutaneum, Rhodotorula glutinus, Rhodotorula graminis* and *Yarrowia lipolytics* (formerly classified as *Candida lipolytics*). As used herein, the term "oleaginous yeast," refers to those microorganisms classified as yeast that can accumulate at least 25% of their dry cell weight as oil. Examples of oleaginous yeast include (but are not limited to) the following genera: *Yarrowia, Candida, Rhodotorula, Rhodosporidium, Cryptococcus, Trichosporon* and *Lipomyces*. Examples of bacteria that may be used in conjunction with the present invention include, but are not limited to, *Rhodococcus opacus, Klebsiella, Clostridium* or *Escherichia*.

Example 1

Growth and Lipid Accumulation of *D. hansenii*

FIG. 1 shows plates with the growth of *D. hansenii* on sugarcane juice. *D. hansenii* (Dh) and *S. cerevisiae* (Sc) grown on medium A containing glucose or various concentrations of sugarcane juice. Minimal media were supplemented with 1.5% yeast extract as well as 5%, 10%, 25%, and 50% (v/v) sugarcane juice. *D. hansenii* grew well on media containing up to 50% sugarcane juice and *S. cerevisiae* did not grow on media containing more than 5% of the sugarcane juice. Lipid accumulation was indicated by Nile Red fluorescence in *D. hansenii* but not in *S. cerevisiae*.

Figure 2:
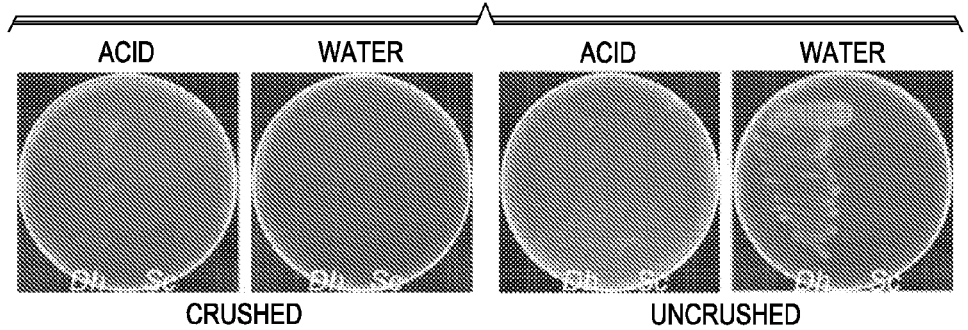
FIG. 2. Plates with the growth of *D. hansenii* using sugarcane bagasse extracts as carbon source.

FIG. 2 shows plates with the growth of *D. hansenii* using sugarcane bagasse extracts as carbon source. *D. hansenii* (Dh) and *S. cerevisiae* (Sc) inoculated on minimal media containing sugarcane bagasse extracts using sulfuric acid or water as solvents. Crushed or uncrushed sugarcane bagasse were pre-treated with 2% sulfuric acid or water at 121° C., 15 psi for 45 min. The supernatant were collected and supplemented in the media at 50% (v/v), and pHs of the media were adjusted to 5.5 with NaOH pellets.

Figure 3:
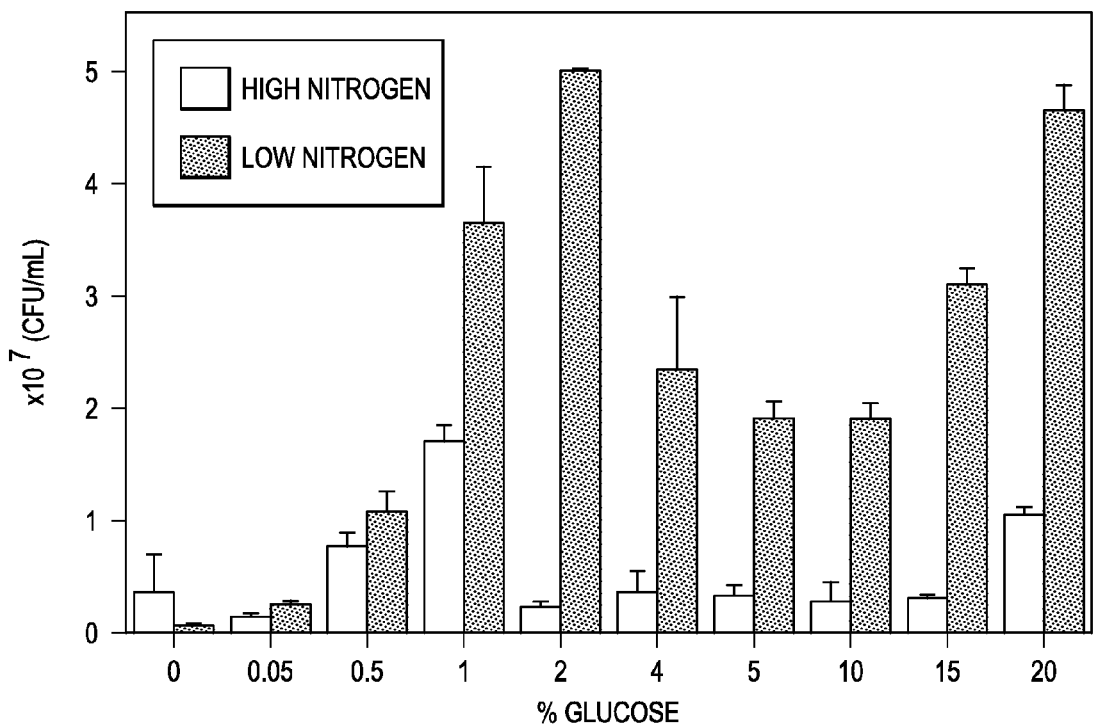
FIG. 3. Growth of *D. hansenii* in liquid media with various concentrations of glucose.

FIG. 3 is a graph that shows the growth of *D. hansenii* in liquid media with various concentrations of glucose. *D. hansenii* growth in Media A with various concentrations of glucose (0, 0.05, 0.5, 1, 2, 4, 5, 10, 15, 20%) and various concentrations of $NH_4Cl$ (low: 0.01 g/L; high: 5 g/L). *D. hansenii* were inoculated in various liquid media and cultured at 30° C. for 120 hr and plated on YPD.

Figure 4:
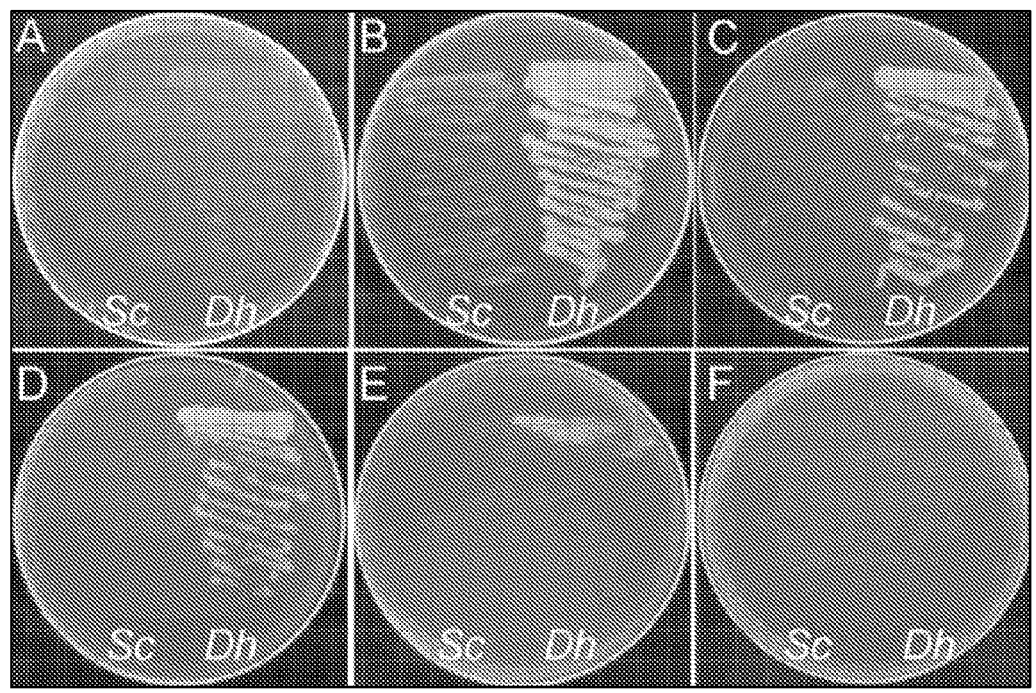
FIG. 4. Growth and oleagenicity of *D. hansenii* on glucose and glycerol containing media.

FIG. 4 shows plates with the growth and oleagenicity of *D. hansenii* on glucose and glycerol containing media. Comparison of *D. hansenii* (Dh) and *S. cerevisiae* (Sc) grown on minimal media. All media were supplemented with 1.5% yeast extract as well as (A) no carbon source, (B) 30 g/L glucose, (C) 10% glycerol, (D) 20% glycerol, (E) 30% glycerol, or (F) 40% glycerol. Plates were illuminated with UV light source (302 nm) to demonstrate lipid accumulation indicated by in vivo lipid staining using Nile Red, which is also supplemented in the media, and upon excitation, fluoresced red in *D. hansenii*. Photographs were taken 6 days post inoculation.

Figure 5:
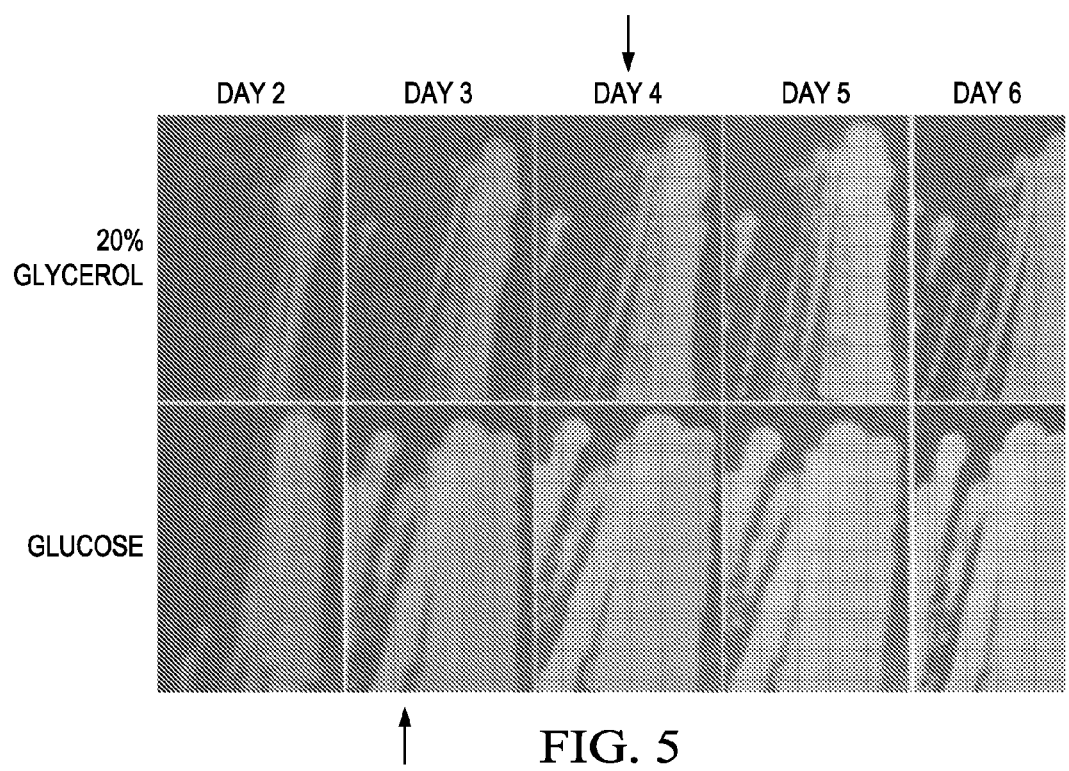
FIG. 5. Time course of lipid accumulation in *D. hansenii*.

FIG. 5 shows a time course of lipid accumulation in *D. hansenii*. Lipids accumulation in *D. hansenii* when grown on minimal media containing 0.5 µg/mL Nile Red plus 20% glycerol or 30 g/L glucose two to six days post inoculation. Cultures were photographed every 24 hr. On glycerol substrate, *D. hansenii* cells fluorescent on day four (red arrow) while on glucose substrate, *D. hansenii* cells fluorescence on day three (green arrow).

Figure 6:
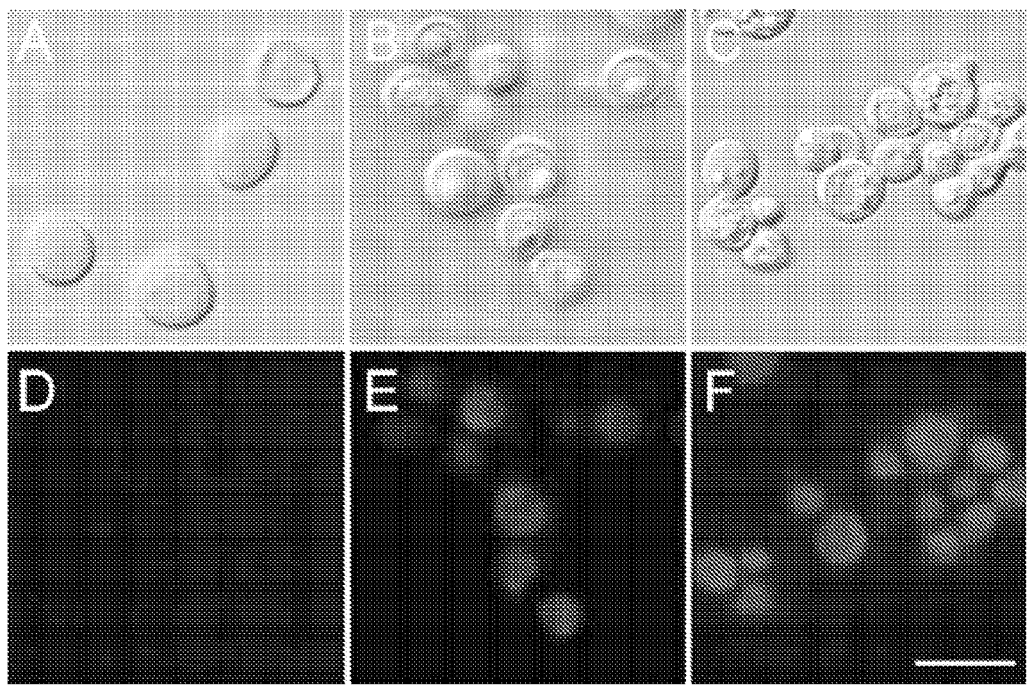
FIG. 6. Micrographs that show the cellular lipid accumulation in *D. hansenii*.

FIG. 6 are micrographs that show the cellular lipid accumulation in *D. hansenii*. Fluorescence microscopy of lipids loaded *D. hansenii* grown on glycerol. *D. hansenii* was grown on minimal media containing Nile Red (0.5 µg/mL) with glycerol (B and E) or glucose (C and F) as carbon sources. Stained with Nile Red (E and F), lipid accumulated in *D. hansenii* cells fluoresced upon UV excitation (560 nm) (E and F), while non-stained cells (D) did not fluoresce. Scale bar=10 µm.

Figure 7A:
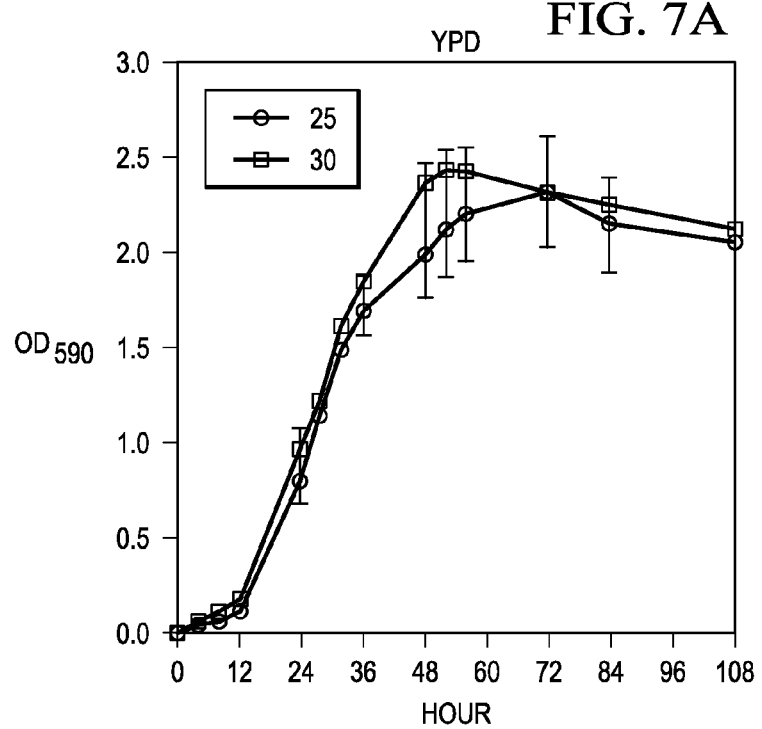
FIG. 7. growth of *D. hansenii* in three different liquid culture media.
Figure 7B:
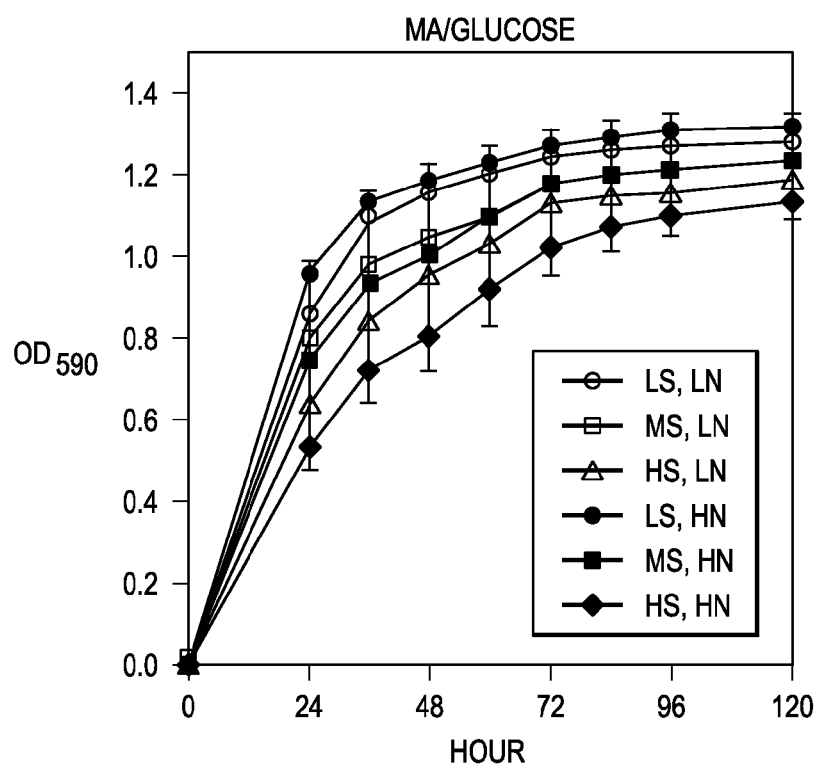
Figure 7C:
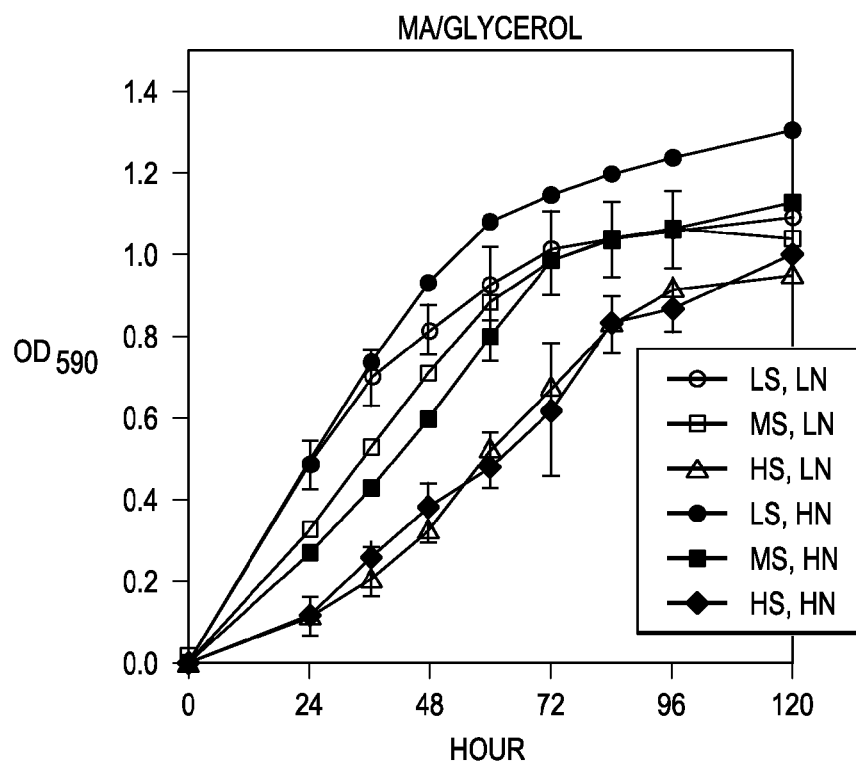

FIG. 7 are graphs that show the growth of *D. hansenii* in liquid media. A. Growth kinetics of *D. hansenii* in YPD liquid medium at 25° C. and 30° C. B. *D. hansenii* grown in minimal media (MM) with glucose (30 g/L) as the sole carbon source. C. *D. hansenii* grown in minimal medium (MM) with 20% glycerol (v/v) as the sole carbon source. LN: 0.1 g/L $NH_4Cl$ low nitrogen concentration; HN: 5 g/L $NH_4Cl$ high nitrogen concentration; LS: 14 mM NaCl low salt concentration; MS: 0.8M NaCl medium salt concentration; HS: 1.6M NaCl high salt concentration. Approximate hours at which cells entered exponential growth phase were 12, 48 and 72 hr for A, B and C, respectively.

TABLE 1

Biomass of *D. hansenii* and *S. cerevisiae*. Cultures initiated with $1 \times 10^6$ cells/mL in 1 L of Medium A grown to saturation after 4 days in shake culture (150 rpm at 30° C.).

| Organism | Medium | Final Cell count (per mL) | Wet[a] weight/L (g) | Dry[b] weight/L (g) |
|---|---|---|---|---|
| *Saccharomyces cerevisiae* | Medium A (with glucose) | $3.3 \times 10^7$ | 2.51 | 0.64 |
| *Debaryomyces hansenii* | Medium A (with glucose) | $1.16 \times 10^8$ | 7.14 | 2.3 |
| *Debaryomyces hansenii* | Medium A with 20% glycerol (no glucose) | $1.73 \times 10^8$ | 8.88 | 3.31 |

[a]Wet weight determined by pelleting cells by centrifugation;
[b]Dry weight determined by lyophilizing pellets.

TABLE 2

*D. hansenii* lipid composition. All lipids were extracted and analyzed using the method of Canuel and Martens (1996). Identification of individual compounds were based on relative retention times of standard compounds and subsequently verified with combined gas chromatography-mass spectrometry. The results here indicate that oleic acid and hexadecane are the most abundant long-chain fatty acids and hydrocarbons in *D. hansenii*. It should be noted that long-chain n-alkanes (e.g., $C_{27}$, $C_{29}$, and $C_{31}$) are generally found in the epicuticular waxes of vascular plants (Bianchi, 2007, and references therein). In contrast, short-chain n-alkanes (e.g., $C_{15}$, $C_{17}$, and $C_{19}$), are derived from algal sources. However, some compounds within $C_{20}$ to $C_{28}$ range are likely produced by bacteria. Earlier work by by Merdinger and Devine (1965) also showed high concentrations of oleic acid, as well as the C22 hydrocarbon anthanthrene, with some hydrocarbons ranging as high C39. Overall, our results did show significant effects of growth media and N-limitation on the relative percentages and composition of lipids in *D. hansenii*. Percent relative abundance of fatty acids, n-alkanols, and hydrocarbons in *D. hansenii* grown in media containing glucose, glycerol or YPD.

| Compound Class | MA with 30 g/L Glucose (high C/N) (% of total) | MA with 20% Glycerol (high C/N) (% of total) | YPD (low C/N) (% of total) |
|---|---|---|---|
| Fatty Acids | | | |
| C-16:1 (oleic acid) | 72.7 | 55.0 | 81.0 |
| C-17 (unknown) | 3.1 | | 2.5 |
| C-20 (unknown) | 14.3 | 25.0 | |
| C-30 (unknown) | 9.9 | 20.0 | 16.5 |
| n-alkanols | | | |
| C-30 | 95.6 | | 10.5 |
| C-40 | 4.4 | | 89.5 |
| Hydrocarbons | | | |
| C-16 (hexadecane) | 77.9 | 96.2 | 25.0 |
| C-16 (unknown) | 5.4 | 0.3 | 12.5 |
| C-17 | | 3.5 | |
| C-20 | 2.3 | | |
| C-26 | 0.9 | | |
| C-27 | 6.3 | | 37.5 |
| C-30 | 3.6 | | |
| C-35 | 2.3 | | |
| C-36 | 1.4 | | 25.0 |
| C-40 | | | |
| C-44 | | | |

Figure 8A:
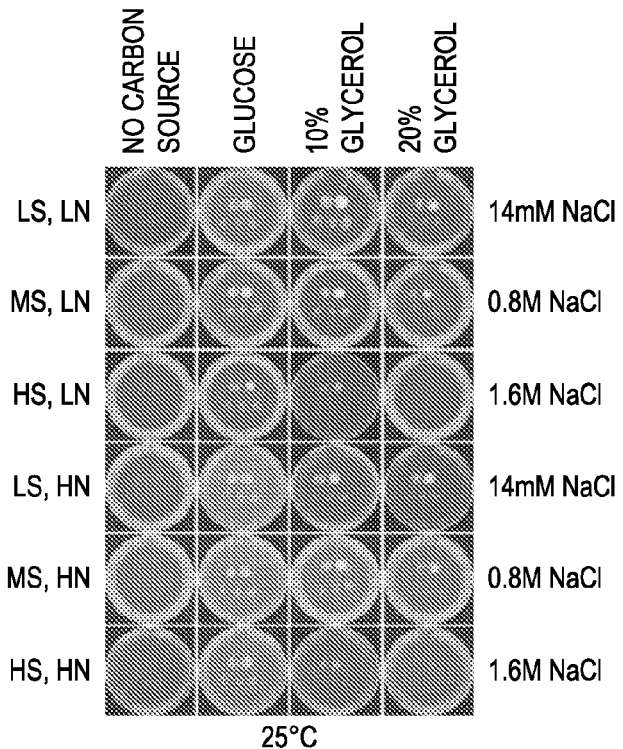
FIG. 8. Lipid accumulation in *D. hansenii* on media containing salt at two different temperatures.
Figure 8B:
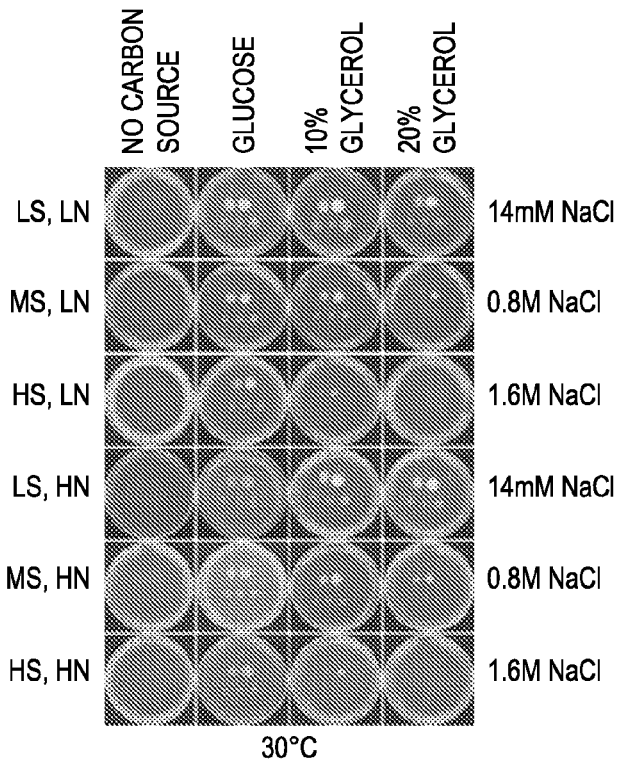

FIGS. 8A and 8B show the lipid accumulation in *D. hansenii* on media containing salt. Lipids-loaded *D. hansenii* grown on Nile red and glucose- or glycerol-containing solid medium at 25° C. (A) or 30° C. (B). Differences in Nile Red staining of serial dilutions of *D. hansenii* cells grown on media containing high (HN: 5 g/L) or low concentrations of $NH_4Cl$ (LN: 0.1 g/L) were insignificant. Fluorescence of Nile Red stained *D. hansenii* grown on various NaCl concentrations (LS: 14 mM, MS: 0.8M, and HS: 1.6M) were similar in strength. Cells grown at 30° C. had slightly stronger fluorescence than that of 25° C.

Figure 9:
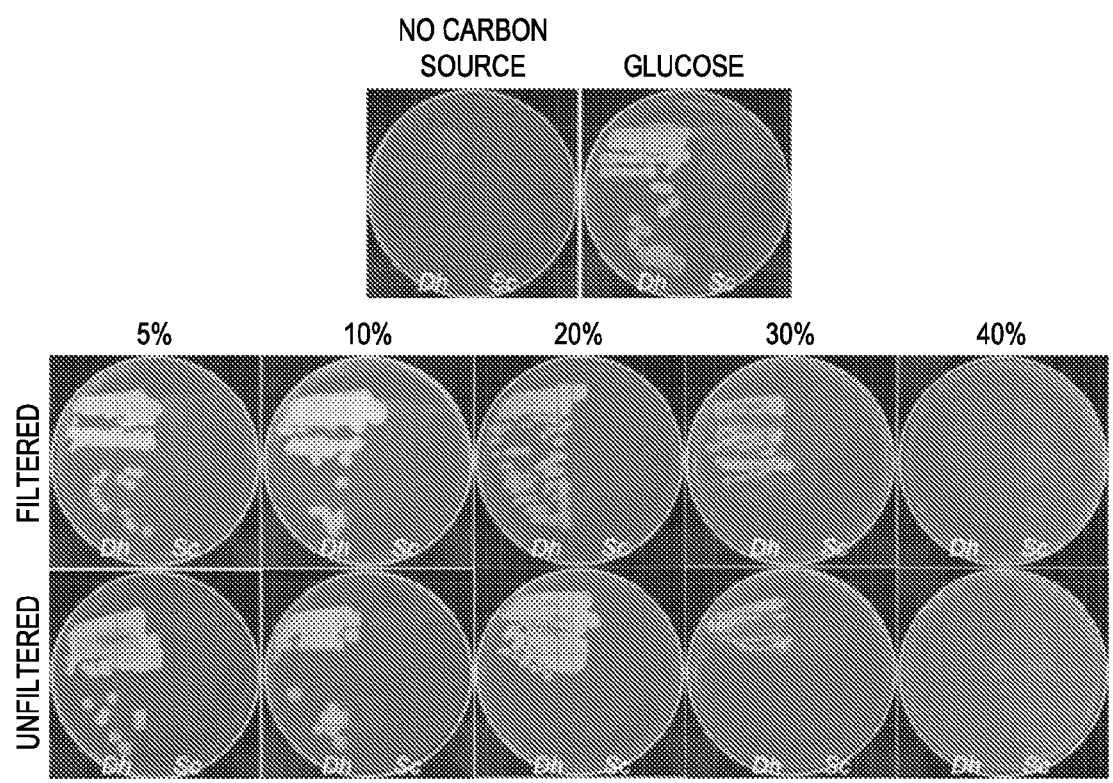
FIG. 9. Growth of *D. hansenii* on crude glycerol.

FIG. 9 shows the growth of *D. hansenii* on crude glycerol. *D. hansenii* (Dh) and *S. cerevisiae* (Sc) grown on minimal media containing various concentrations of crude glycerol generated from a biodiesel plant. Minimal media were supplemented with 1.5% yeast extract as well as 5% (A), 10% (B), 20% (C), 30% (D) and 40% (F) filtered (upper panels) or unfiltered (lower panel) crude glycerol. *D. hansenii* grew well on media containing up to 30% of the crude glycerol and *S. cerevisiae* did not grow on media containing more than 5% of the crude glycerol. Lipid accumulation was indicated by Nile Red fluorescence in *D. hansenii* but not in *S. cerevisiae*.

Figure 10:
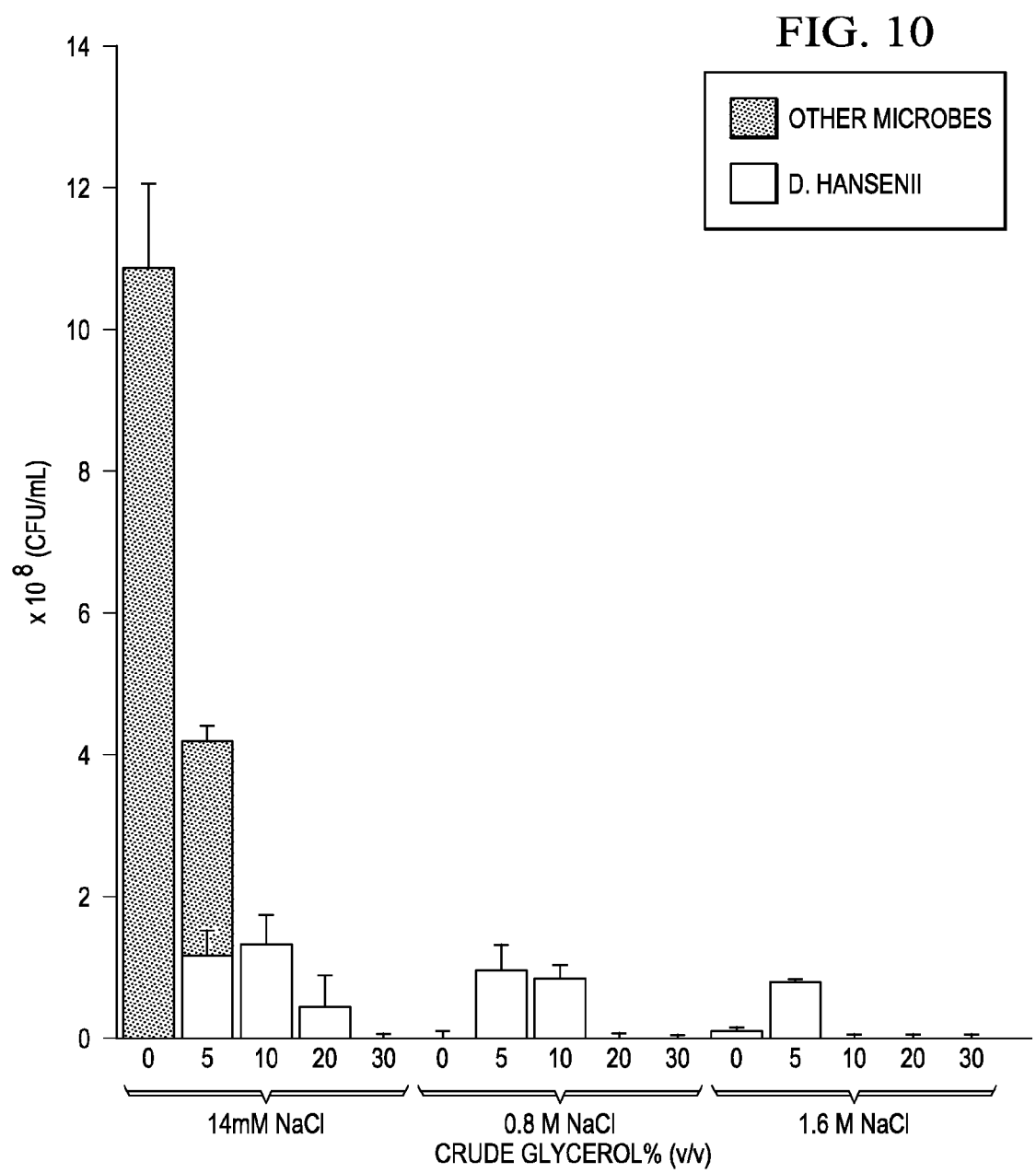
FIG. 10. Inhibition of microbial contamination with salt in growing cultures of *D. hansenii*.

FIG. 10 is a graph that shows inhibition of microbial contamination with salt in growing cultures of *D. hansenii*. Microbial growth in non-sterile tap water-based media with crude glycerol from a biodiesel plant and various concentrations of NaCl. *D. hansenii* were inoculated in various liquid media and cultured at 30° C. for 48 hr and plated on YPD. All microbe colonies formed on solid YPD plates were counted. Total osmolarity of the media calculated based on NaCl and glycerol were indicated in red below the X-axis label. Total osmolarity of 1.5M inhibited contamination of cultures from other microbes.

Figure 11:
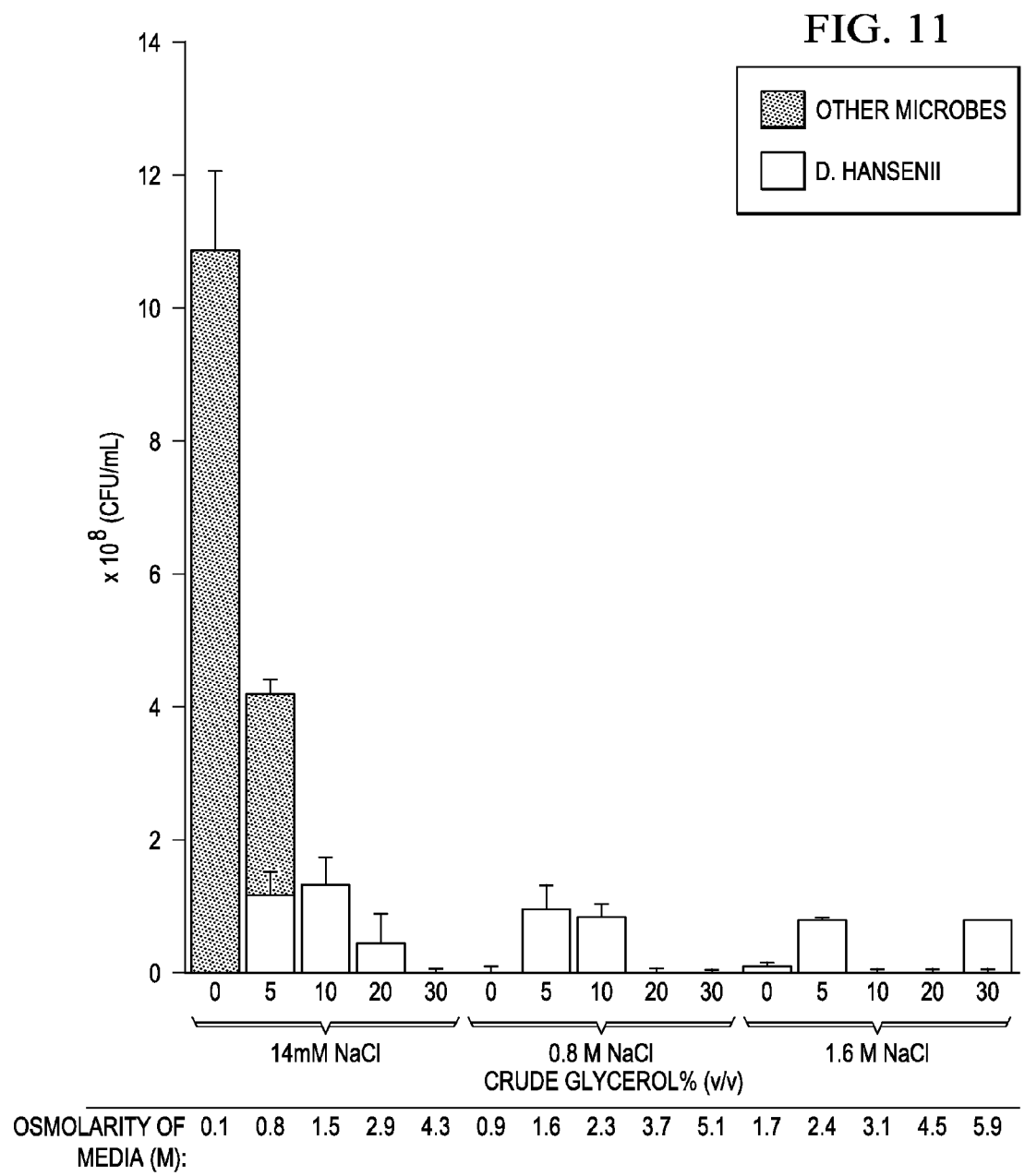
FIG. 11. Inhibition of microbial contamination with salt in growing cultures of *D. hansenii*.

FIG. 11 is a graph that shows inhibition of microbial contamination with salt in growing cultures of *D. hansenii*. Microbial growth in non-sterile tap water with crude glycerol from a biodiesel plant and various concentrations of NaCl. *D. hansenii* were inoculated in various liquid media and cultured at 30° C. for 48 hr and plated on YPD. All microbe colonies formed on solid YPD plates were counted.

Figure 12:
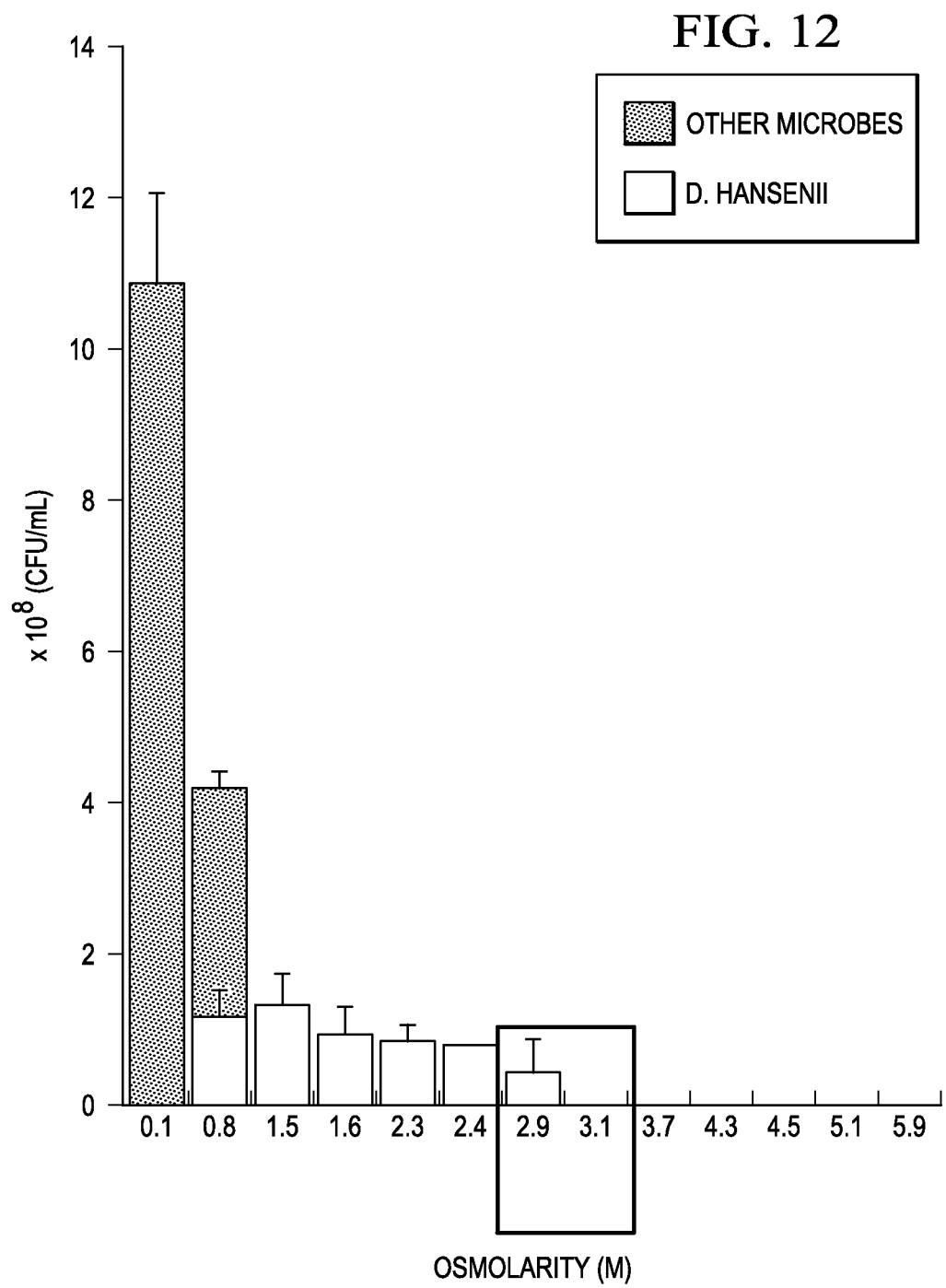
FIG. 12. Salt-tolerance of *D. hansenii*.

FIG. 12 is a graph that shows the salt-tolerance of *D. hansenii*. Microbial growth in non-sterile tap water-based media with crude glycerol from a biodiesel plant and various concentrations of NaCl plotted again osmolarity of the media. *D. hansenii* were inoculated in various liquid media and cultured at 30° C. for 48 hr and plated on YPD. All microbe colonies formed on solid YPD plates were counted. *D. hansenii* tolerated salt to osmolarity of 2.9 M.

Figure 13:
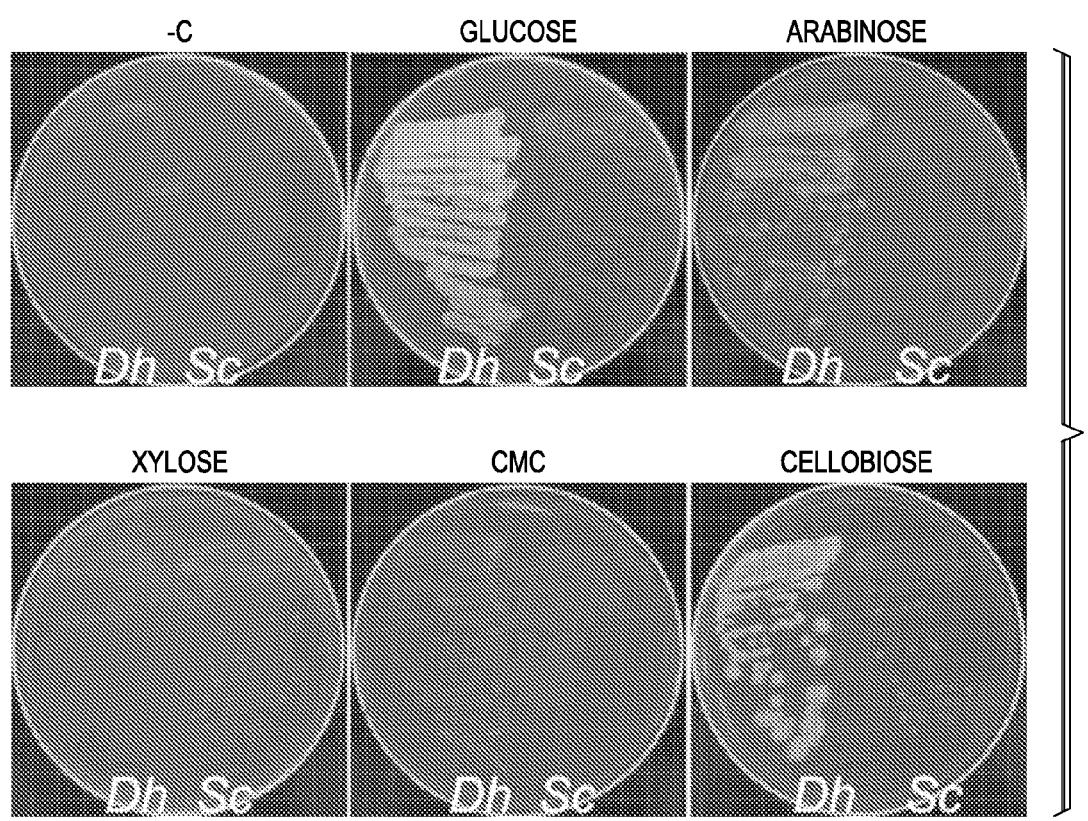
FIG. 13. Growth of *D. hansenii* on pure carbon sources.

FIG. 13 shows the Growth of *D. hansenii* on pure carbon sources. *D. hansenii* (Dh) and *S. cerevisiae* (Sc) grown on minimal media containing no carbon source, 30 g/L of glucose, arabinose, xylose, carboxymethylcellulose or cellobiose. *D. hansenii* grew well on media containing glucose, arabinose and cellobiose. Lipid accumulation was indicated by Nile Red fluorescence in *D. hansenii* grown on glucose but not on cellobiose.

Figure 14:
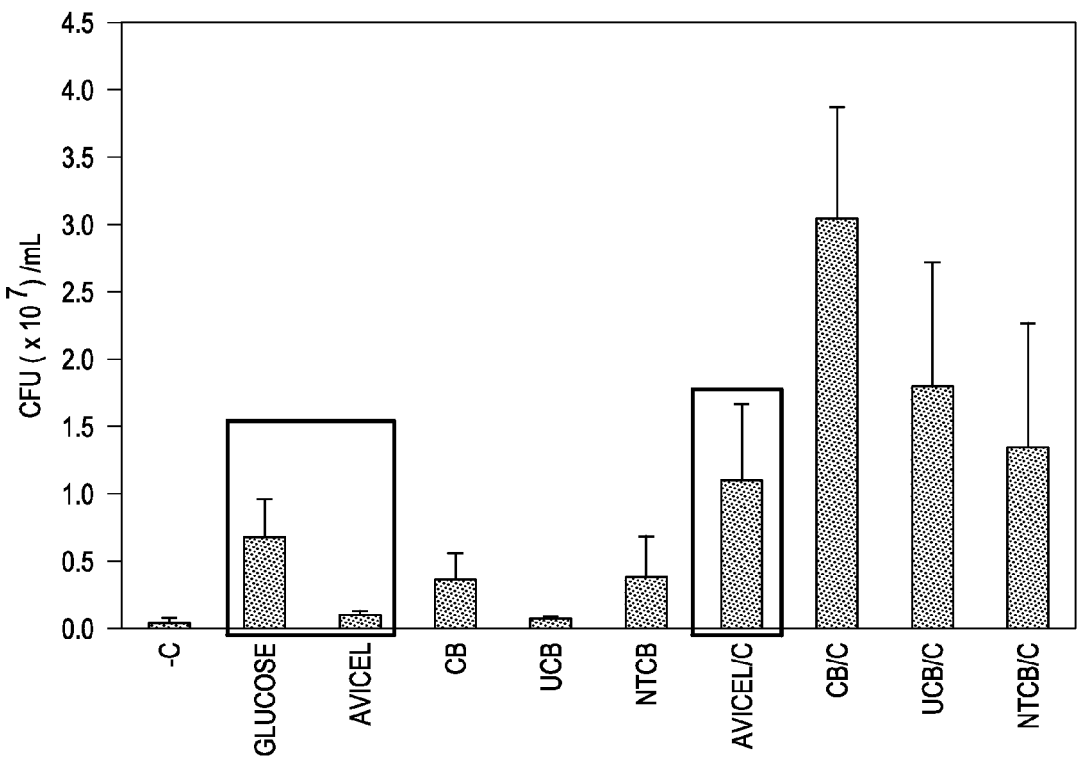
FIG. 14. Growth of *D. hansenii* in liquid media containing Avicel (microcrystalline cellulose) and cellulase—treated Avicel.

FIG. 14 is a graph that shows the growth of *D. hansenii* in liquid media containing Avicel (microcrystalline cellulose) and cellulase—treated Avicel. Growth of *D. hansenii* in liquid media containing cellulose (avicel) or cellulosic biomass (sugarcane bagasse). —c: no carbon source; CB: acid pretreated crushed bagasse; UCB: acid pretreated uncrushed bagasse; NTCB: non-treated crushed bagasse; Avicel/C: cellulase digested Avicel; CB/C: cellulase digested acid pretreated crushed bagasse; UCB/C: cellulase digested acid pretreated uncrushed bagasse; NTCB/C: cellulase digested non-treated crushed bagasse. Glucose and bagasse (dry) were added to the media at 30 g/L.

Figure 15:
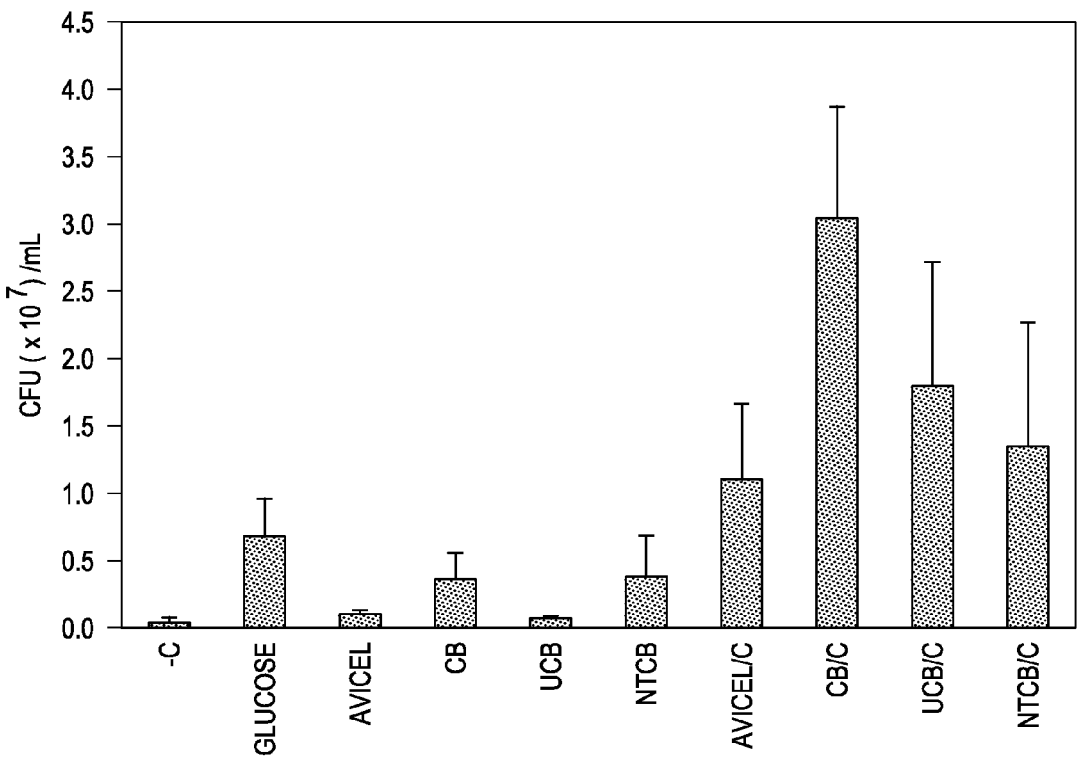
FIG. 15. Growth of *D. hansenii* using cellulase—treated sugarcane bagasse as carbon source FIG. 16. *D. hansenii* hygromycin sensitivity test.

FIG. 15 is a graph that shows growth of *D. hansenii* using cellulase-treated sugarcane bagasse as carbon source. Growth of *D. hansenii* in liquid media containing cellulose (avicel) or cellulosic biomass (sugarcane bagasse). —c: no carbon source; CB: acid pretreated crushed bagasse; UCB: acid pretreated uncrushed bagasse; NTCB: non-treated crushed bagasse; Avicel/C: cellulase digested Avicel; CB/C: cellulase digested acid pretreated crushed bagasse; UCB/C: cellulase digested acid pretreated uncrushed bagasse; NTCB/C: cellulase digested non-treated crushed bagasse. Glucose and bagasse (dry) were added to the media at 30 g/L.

Figure 16:
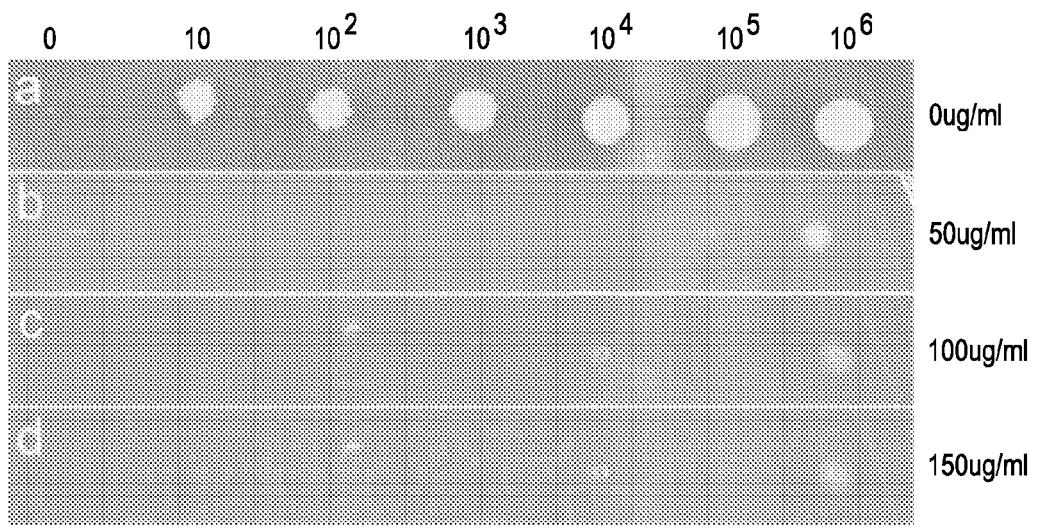

FIG. 16 shows a *D. hansenii* hygromycin sensitivity test. *D. hansenii* is sensitive to hygromycin. Various amount of *D. hansenii* cells were inoculated on plates containing 0 (a), 50 (b), 100 (c) or 150 (d) μg/mL hygromycin. A working concentration of 100 μg/mL medium for hygromycin resistance gene transformation into *D. hansenii* can be used.

TABLE 3

Growth and oleagenicity of *D. hansenii* on pure oligosaccharides

| Carbon source | Growth | Oleagenicity |
|---|---|---|
| Glucose | +++ | Yes |
| Arabinose | +++ | No |
| Xylose | + | No |
| Cellobiose | ++ | No |

TABLE 3-continued

Growth and oleagenicity of D. hansenii on pure oligosaccharides

| Carbon source | Growth | Oleagenicity |
|---|---|---|
| CMC (carboxymethyl cellulose) | ++ | No |
| Avicel (microcrystalline cellulose) | ++ | No |

As will be apparent to one skilled in the arts, the invention has broad implications beyond oleaginous microbes, and can be readily extended—by one skilled in the arts, to other kinds organisms, including but not limited to green algae.

The present invention includes systems and methods for the conversion of short-chain carbohydrates from biofuel formation and cellulosic biomass into high energy fuels. The present invention may be used with one or more known methods for final recovery of hydrocarbons and other lipids. The recovery of long chain fatty acids and hydrocarbons may include of one or several steps. For maximum recovery of fatty acids and hydrocarbons, water content of yeast cells may be reduced to 10-20% w/w by a suitable method. Suitable methods include oven drying, spray draying, drum drying, pneumatic flush drying and similar method used in food, feed and chemical industries. Dried cell biomass can then be ground/homogenized/sheared in the presence of organic solvent or a mixture of organic solvents. Organic solvents of choice may include hexane, mixture of hexane and ethanol, chloroform and methanol. Organic solvent(s) are separated from the lipophilic compounds (fatty acids and hydrocarbons) by evaporation to yield a solvent-free mixture of fatty acids and hydrocarbons that are further processed into biodiesel, gasoline or jet fuel.

Strains. $D.$ $hansenii$ strain NRRL Y-1448 (ATCC 10619) and $S.$ $cerevisiae$ strain BY4742 were obtained from the American Type Culture Collection (Virginia, USA) and maintained on YPD agar (casein peptone 2%, yeast extract 1%, glucose 2%, 1.5% agar; USB Corporation, Ohio, USA).

Culture media and cultivation conditions. For liquid culture, single colony of $D.$ $hansenii$ or $S.$ $cerevisiae$ were pre-cultured in 2 mL YPD or other desired media (see below) and incubated at 30° C. for 24 hr. Cells were counted using a hemacytometer and spun down at 3000 rpm for 15 minutes. Cells at a concentration of $1\times10^6$/mL were used to inoculate the desired media with 1% of the total volume. Medium A with limited nitrogen source (glucose 30 g/L, yeast extract 1.5 g/L, $NH_4Cl$ 0.1 g/L, $KH_2PO_4$ 7.0 g/L, $Na_2HPO_4$ 1.983 g/L, $MgSO_4\cdot7H_2O$ 1.5 g/L, $FeCl_3\cdot6H_2O$ 0.08 g/L, $ZnSO_4\cdot7H_2O$ 0.01 g/L, $CaCl_2\cdot2H_2O$ 0.1 g/L, $MnSO_4\cdot H_2O$ 0.07 mg/L, $CuSO_4\cdot5H_2O$ 0.1 mg/L, $Co(NO_3)_2\cdot6H_2O$ 0.1 mg/L, pH 5.5; see Kimura et al., 2004) was used to support the growth of $D.$ $hansenii$ and induce cellular lipid accumulation. Medium A with sufficient nitrogen supply ($NH_4Cl$ 5 g/L) was used to support growth without the induction of lipid accumulation. To test the growth of $D.$ $hansenii$ on carbon sources other than glucose, glucose was dropped out from medium A and replaced with desired carbon sources at the same concentration except for glycerol, which was at 10% or 20% (v/v). Sorgum juice was obtained from Department of Soil and Crop Sciences, Texas A&M University, and had an average sugar content of 13.42% (brix %). For making media containing sorghum juice, raw juice was filter sterilized and added in the media at various concentrations of 5%, 10%, 25%, and 50% (v/v). Crude glycerol (Future Fuel Chemical Company, Arkansas, USA) contained 6% water, 88% glycerol, 2.564% ash by weight.

Nile red plate staining assay. Nile red (9-diethylamino-5H-benzo[α]phenoxazine-5-one) obtained from Sigma-Aldrich (Missouri, USA) was dissolved in Dimethyl sulfoxide (DMSO) at a concentration of 0.5 mg/mL and supplemented in medium A at a final concentration of 0.5 μg/mL. For direct observation of cellular lipid accumulation, $D.$ $hansenii$ grown on solid medium A with Nile red were observed using a UV light source (312 nm) as described (Spiekemann et al., 1999).

Growth, lipid accumulation and substrate utilization kinetics. For growth kinetics studies, $D.$ $hansenii$ cells were inoculated in 2 mL of desired media and cultured overnight. Then 500 uL $D.$ $hansenii$ cell suspension at a concentration of $10^6$ cells/mL were inoculated into 50 mL media and incubated at 30° C. Optical cell density was measured at 590 nm on a microplate reader SPECTRAFluor (Tecan Group Ltd., Männedorf, Switzland) every 12 hr for 84-96 hr. Total lipid accumulation were determined by Nile red fluorescence with the method by Kimura et al. (ref). Glucose concentration in growth media at different growth stages were determined using LabAssay™ Glucose (Wako Chemicals USA, Inc. Richmond, Va.). Glycerol/triglyceride concentrations in growth media at different growth stages were determined using Triglyceride Assay Kit (Cayman Chemical Company, Ann Arbor, Mich.). All experiments were performed in triplicates.

Fluorescent microscopy. After cultivation on Nile red supplemented solid media, cells were suspended in sterile water and mounted on a microslide for microscopy. Microscopic photographs were taken with an Olympus BX51 microscope (Olympus America, New York, USA) equipped with an Olympus DP70 camera using a 530-550 nm excitation filter, a 570 nm diachronic mirror and a 590 nm emission filter with a 60× objective lens.

Osmostress tolerance study. For growth comparison in liquid media (made with tap water and no sterilization was involved) containing osmolytes, $D.$ $hansenii$ cells were inoculated in 2 mL of the desired media, and aliquots were spread on YPD plates and cells were counted as colony-forming units after 2 days of growth at 30° C.

Treatment of cellulosic materials. Crushed (dry and chopped) and uncrushed (wet and untreated) sugarcane bagasse were obtained from field. For pretreatment with acid, 100 g crushed and 200 g of uncrushed bagasse were soaked individually in 1 L 2% $H_2SO_4$ and autoclaved at 121° C. and 16 psi for 60 min. Then the bagasse was kept at room temperature in acid for 2 hr. The liquid was filtered through whatman filter paper followed by continuous wash of the bagasse with deionized water till pH 7. Medium A containing sugarcane bagasse extract were made using the flow through and the pH was adjusted to 5.5. For pretreatment with water, the same procedures were followed using deionized water for the initial treatment. Avicel was obtained from Sigma (St. Louis, Mo.). Cellulase (108 U/mg dry weight) was obtained from Worthington (Lakewood, N.J.). Stock enzyme solution was prepared in deionized water at 10 mg/mL and filter sterilized. For cellulase treatment, 1 mg (100 μL) enzyme were added to cellulosic materials and incubated at 37° C. overnight.

Example 2

Oleaginous Microbes to Provide Bioenergy Feedstocks and High Value Transportation Fuels Utilization of biofuels provides the promise of reducing greenhouse gas emissions and enhancing domestic energy independence. However, current platforms for biofuel production are inefficient. For example, biodiesel synthesis via transesterification of oil seeds yields a 10% waste stream of glycerol. Harnessing microbes to convert this waste stream directly to biodiesel has the potential of dramatically improving the economics of the industry. *D. hansenii* is a notable microbe because it is oleagenic, producing greater than 50% of its biomass as long chain hydrocarbons, fatty acids and sterols. Remarkably this yeast can utilize glycerol as its sole carbon source. Therefore *D. hansenii* shows great promise for the direct conversion of the glycerol waste stream into high-energy transportation fuels. To harness this extraordinary capacity for the biofuels industry, the present invention developed compositions and methods to optimize hydrocarbon synthesis. Furthermore, downstream optimization of metabolic pathways requires an enhanced understanding of the genetic pathways that contribute to glycerol utilization and hydrocarbon synthesis.

Biofuels hold great promise for reducing greenhouse gas emissions and enhancing domestic energy independence [1-3]. In addition, the activities of the biofuel industry are expected to positively impact the development of rural and agricultural economies, including impoverished regions along the U.S.-Mexico border where agriculture is a particularly important to the regional economy [4-6]. Despite this promise, the biofuel industry remains plagued by production inefficiencies that may jeopardize its long-term viability [3, 7, 8]. Therefore, technologies that improve the efficiency and economics of biofuel production are critical to the success of the industry [2, 9].

A salient example of biofuel production inefficiency is associated with biodiesel synthesis, where large quantities of glycerol wastes are generated during the refining process. With every 100 kg of biodiesel produced by the transesterification of oil seeds, 10 kg of crude glycerol are generated. Processes that can capture value from this waste stream by converting crude glycerol into high value products have the potential to dramatically improve the economics of the industry. In fact, the efficient utilization of this waste stream has been recognized as being critical to the economic viability of the industry [10, 11]. Recently, microbes that ferment glycerol into ethanol have been described [12-15]. However, ethanol is not compatible with existing transportation infrastructure, and possesses less energy per molecule than gasoline and other long-chain hydrocarbons. Therefore, technologies that enable the direct bioconversion of glycerol into long-chain hydrocarbons, including biodiesel and jet fuel, hold significant promise. The present invention is a novel biotechnology platform, the oleaginous and halotolerant yeast *D. hansenii* [16], for the direct bioconversion of glycerol into high-energy transportation.

Oleaginous microbes provide a compelling route for converting bioenergy feedstocks into high value transportation fuels. By definition, oleaginous microbes are organisms in which long-chain hydrocarbons and lipids constitute greater than 25% of the cell dry weight [17-21]. To date, several oleaginous microbes have been described, including oleaginous bacteria (e.g., *Rhodococcus opacus, Nocardia restricta, Mycobacterium avium*) and yeasts (e.g., *Debaryomyces* sp., *Rhodosporidium* sp., *Rhodotorula* sp., and *Lipomyces* sp.) [17, 18, 20].

Oleaginous yeasts possess several intriguing properties. First, several species can grow on a variety of carbon sources, including xylose, glucose, and arabinose [16, 22]. *Debaryomyces* is notable for its ability to grow on glycerol as the sole carbon source (see below). In addition, oleaginous yeasts produce triacylglycerides (TAGs) with long-chain fatty acids (LCFA), comparable to those found in vegetable oils (e.g., canola, palm, corn, coconut, and jatropha oils), animal fats, and microalgae ([23], and references therein). Finally, several oleaginous species grow rapidly in culture in both rich and selective media, and hence are amenable to laboratory manipulation [24]. Therefore, oleaginous yeasts constitute a viable candidate for the synthesis of long chain hydrocarbons used in biodiesel production.

Growth conditions that lead to maximal accumulation of lipids in oleaginous yeasts have been investigated [25]. In general, most oleaginous yeasts grown in continuous culture will accumulate lipids if an adequate carbon (C) source, such as glucose, is available ([25], and references therein). However, maximal accumulation of lipids in these microbes, typically in the form of intracellular oil droplets, occurs during a transition where the carbon source remains plentiful, but another nutrient, particularly nitrogen (N), is limiting [26, 27]. For example, in the yeast *Cryptococcus curvatus*, not only does maximum lipid production (ca. $0.59$ g lipid $L^{-1} h^{-1}$) occur during N limitation, but the composition of fatty acid constituents of the accumulated lipids are altered under this growth condition [28, 29]. During the high growth phase of *C. curvatus*, $C_{18:2}$ (linoleic acid) is the dominant component of membranes; this is followed by a dominance of $C_{18:0}$ (stearic acid) and $C_{18:1}$ (oleic acid), reflective of storage TAGs in a later accumulation phase. Typically, after the N source is exhausted, *C. curvatus* cell numbers and lipid-free biomass accumulation ceases. Then intracellular lipids accumulate—reaching greater than 60% of the dry cell weight [30, 31]. In addition to the three aforementioned LCFAs, some other LCFA commonly found in oleaginous fungi are $C_{16:0}$ (palmitic acid) and $C_{16:1}$ (palmitoleic acid) [32, 33]. Other work has shown that some of N limitation effects may be linked to a decrease in the abundance of adenosine monophosphate (AMP), via an AMP deaminase enzyme that adaptively liberates nitrogen from AMP in the form of ammonium [34, 35]. The dominant fatty acids in *C. curvatus* grown on glucose are oleic, palmitic, and stearic acids [36]. Similarly, the dominant fatty acids in the lipids of glucose-grown *D. hansenii* are palmitic acid (23.7%) and oleic acid (50.1%), with 59.7% of all of the fatty acids being unsaturated [37]. In addition, the hydrocarbons in *D. hansenii* range from $C_{16}$ to $C_{39}$ and are dominated by $C_{22}$. Finally, previous work has demonstrated *D. hansenii* contains ergo sterol, stigma sterol and another unidentified sterol [37].

The molecular mechanisms mediating fatty acid biosynthesis and triacylglyceride (TAG) accumulation in yeast have been best described in the non-oleagenous model *S. cerevisiae* [38, 39], which is closely related to *D. hansenii*. Importantly, insights gained in this system have proven useful for understanding lipid accumulation in several oleaginous microbes [40, 41], including *Debaryomyces* [16], which shares many conserved genes. TAG synthesis in *Saccharomyces* proceeds in a stepwise fashion. First, phosphatidic acid (PA) and diacylglycerol (DAG) are synthesized. During PA synthesis, glycerol 3-phosphate G-3-P is diacylated to yield PA. Alternatively, dihydroxyacetone phosphate (DHAP) is acylated by DHAP acyltransferase (DHAPAT) to form 1-acyl-DHAP. This molecule is then reduced by 1-acyl-DHAP reductase (ADR) to yield lysophosphatidic acid (LPA). This product is then acylated to form PA. PA can also be formed from phospholipids through the action of a phospholipase D, or by phosphorylation of DAG through DAG kinase. Dephosphorylation of PA by a phosphatidate phosphatase (PAP) yields DAG. Finally, diacylglycerol acyltransferases (DAGATs) convert DAG to TAG using assorted acyl donors. The ability of certain oleaginous yeasts to accumulate lipids may also be strongly linked to having another enzyme, ATP: citrate lyase (ACL), not found in non-oleaginous yeasts [42].

Yeasts also accumulate unesterified long chain hydrocarbons, which can range from 0.01 to as much as 10.2% of the cell dry weight in aerobic and anaerobic conditions, respectively [43]. In fact, D. hansenii is one of three yeasts know to produce these hydrocarbons [44], the other two are Candida guilliermondii and Saccharomyces cerervisiae [43]. The effects of C. substrate have also been shown to affect the composition of hydrocarbons in yeasts. For example, C. tropicalis grown on glucose typically produces mid-chain alkanes ($C_{16}$-$C_{19}$), while 49 to 66% of the alkanes are in long-chain ($C_{22}$-$C_{25}$) when grown on glycerol. The role of unesterified hydrocarbons in yeasts and other microorganisms remains unclear but are most likely used as membrane support structures. Nevertheless, these stable long-chain hydrocarbons are potentially very useful in development of biodiesel from yeast cells.

The present invention include compositions and methods including the culture conditions for, and strains of, the oleaginous and halotolerant yeast D. hansenii, which supports the direct bioconversion of glycerol and other carbon sources into biodiesel and other high-energy fuel oils. D. hansenii constitutes a compelling bioconversion platform. First, unlike S. cerevisiae, D. hansenii possesses the remarkable ability to mediate the biotransformation of glycerol into high value long-chain hydrocarbons and lipids commonly used for biodiesel synthesis ([37], our preliminary data). In fact, when D. hansenii is grown on glycerol, neutral lipids constitute ~50% of the dry weight of the organism (our preliminary data, see below). Importantly, glycerol utilization appears to be a property that is reserved for only a few of the oleaginous yeasts described to date. The genome sequence of D. hansenii has been determined (cbi.labri.fr/Genolevures/) and key tools for the genetic manipulation of the organism. For example, tools for transformation and heterologous gene expression have been developed for D. hansenii [45, 46]. Finally, D. hansenii grows rapidly under high salt conditions where the risk of contamination to industrial-scale bioreactors is limited ([47, 48], our preliminary data). Therefore, D. hansenii provides a potentially powerful platform for addressing a critical need in the biofuel industry.

The feasibility of developing D. hansenii into an economically viable biofuel platform is linked to the yield and composition of neutral lipids [defined as (lipid weight)/(cell dry weight)] produced by the organism under defined conditions. Higher yields translate into a more attractive process. Therefore, understanding the molecular mechanisms that determine the net yield of neutral lipids produced by D. hansenii under defined conditions constitutes a critical milestone its development as a biofuel platform. Before the described studies, a systematic analysis of the molecular genetic and culture condition dependent parameters that influence yield has not been attempted in this organism. This invention attacks this issue by defining modified genes (and corresponding biochemical pathways) that regulate the yield of harvestable (i.e., secreted) oils in D. hansenii.

As stated above, several oleaginous microbes have been described, and their extraordinary potential for biofuel synthesis has been documented. However, the extraction of microbial oils from cells, which are sequestered within cytoplasmic oil bodies, is costly, time-consuming, and prevents continuous cultivation and oil harvesting. Overcoming these obstacles is required for the long-term economic viability of this approach. Discoveries that render currently inaccessible oil bodies available for efficient extraction have the potential to dramatically transform the industry. We uncovered, modified, and exploited a novel "microdiesel" platform that uses the oleaginous yeast D. hansenii for the conversion of biomass into high-energy biocrude. This microbe possesses compelling properties for biofuel synthesis (Table 4). Most importantly, however, we have shown that this remarkable microbe can actively release oil into the environment, which creates unique opportunities for delivering next generation microbial oil solutions.

TABLE 4

Properties for biofuel synthesis.

| Properties | Baker's yeast | Debaryomyces | Debaryomyces microdiesel platform |
|---|---|---|---|
| Salt tolerance | 1.7M NaCl | 4M NaCl | Few competing demands |
| pH tolerance | 5-7 | 3-10 | Few competing demands |
| Oil accumulation | Low neutral lipids (<5%) | Large quantities of neutral lipid (20-50%) | Direct conversion of lipids |
| Growth rate | Very fast (1.5-2 hours/doubling) | Fast (3-4 hours/doubling) | High yield potential |
| Substrate utilization | No growth on glycerol and cellobiose | Use glycerol and cellobiose while synthesizing oil | Enhanced refinery profitability |
| Co-products | Few | Biopolymers Protein Polysaccharides | Added value |
| Genetics | Superb | Good | Engineered strains and designer oil production |
| Oil extraction | No release Cell breakage required | Oil actively released Aqueous extraction enabled | Low cost in oil separation |

Autophagy is a catabolic process in which (an energy starved) cell degrades its own components. The phenomena is highly organized, and tightly regulated, and critical to the maintenance of cellular homeostasis under a variety of stress and developmental conditions and processes, respectively. It is a major mechanism by which a starving cell reallocates nutrients from unnecessary processes to more-essential processes. Autophagic events occur within the autophagosome—a special organelle that contains membrane that is derived from the endoplasmic reticulum. Autophagosomes can fuse with the lysosome, which drives the digestion and processing of molecules contained within the autophagosome.

One key aspect of the invention described here is that modulation of autophagosome pathways can drive the secretion of oil bodies from microbial cells. This unexpected finding provides unique opportunities to generate that can secrete oil at high efficiency.

One embodiment of the invention includes a process whereby a natural or genetically engineered variant of an archaeal, eukaryotic or prokaryotic cell secretes oil. The process involves either growing the cell under conditions that promote secretion or engineering the cell to contain components that modulate the amount of secretion or the composition of oils and/or lipids that are secreted.

In the case where oil secretion is achieved in a process of cultivating the cell under conditions that promote oil secretion, several cultivation conditions have been defined. These include, but are not limited to, conditions in which the cell is grown under low nitrogen (e.g., nitrogen starvation) or nitrogen limiting conditions that have been established to induce autophagy [60-63].

Figure 17:
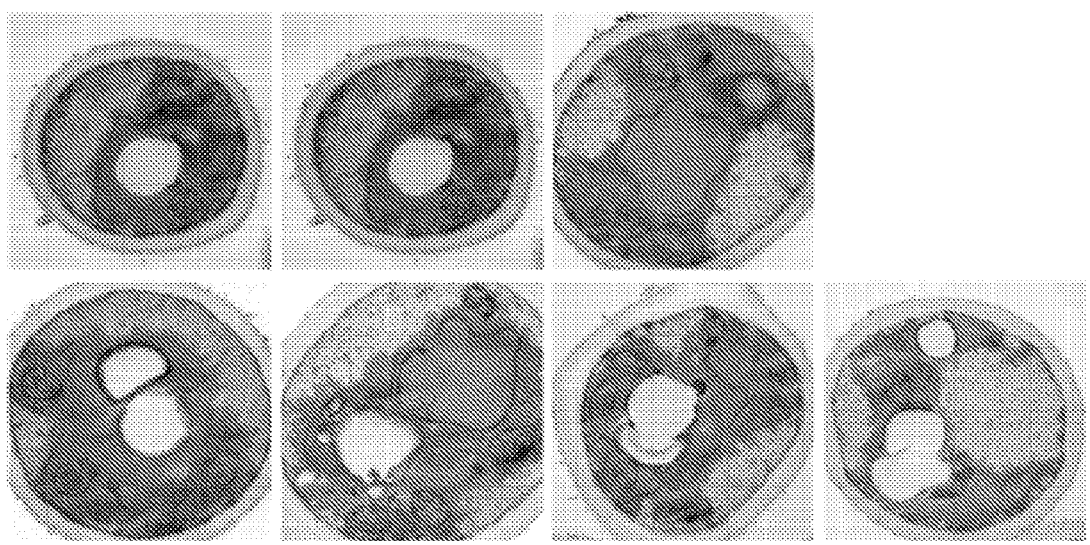
FIG. 17. Electron micrographs of *D. hansenii* cells derived from wortmannin-treated, 48 hr liquid cultures. Lipid bodies (large white inclusions) are physically separated from vacuolar and nuclear compartments.
Figure 18:
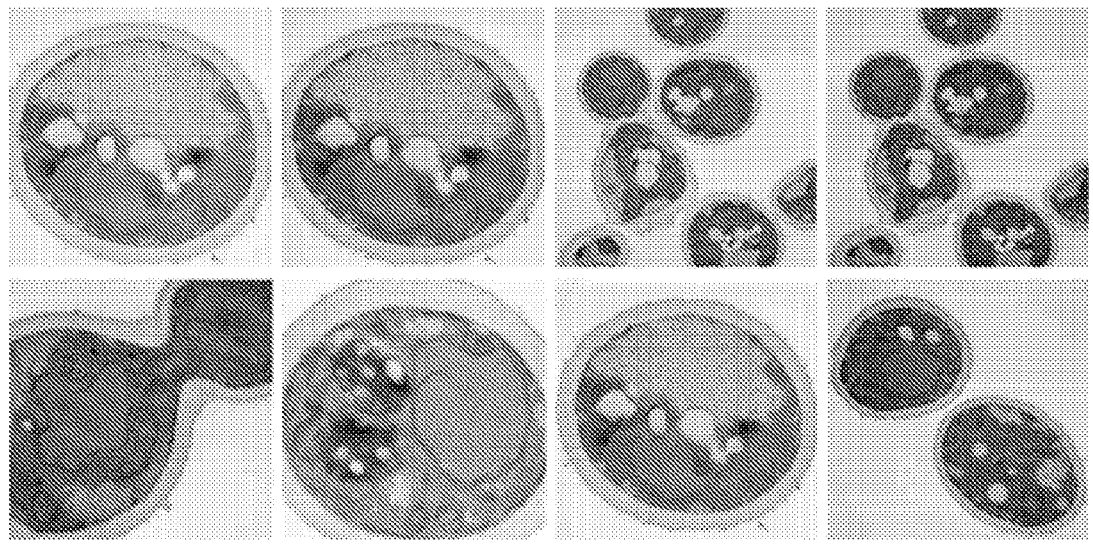
FIG. 18. Electron micrographs of *D. hansenii* cells derived from untreated 48 hr liquid cultures. Lipid bodies (large white inclusions) are physically separated from vacuolar and nuclear compartments.
Figure 19:
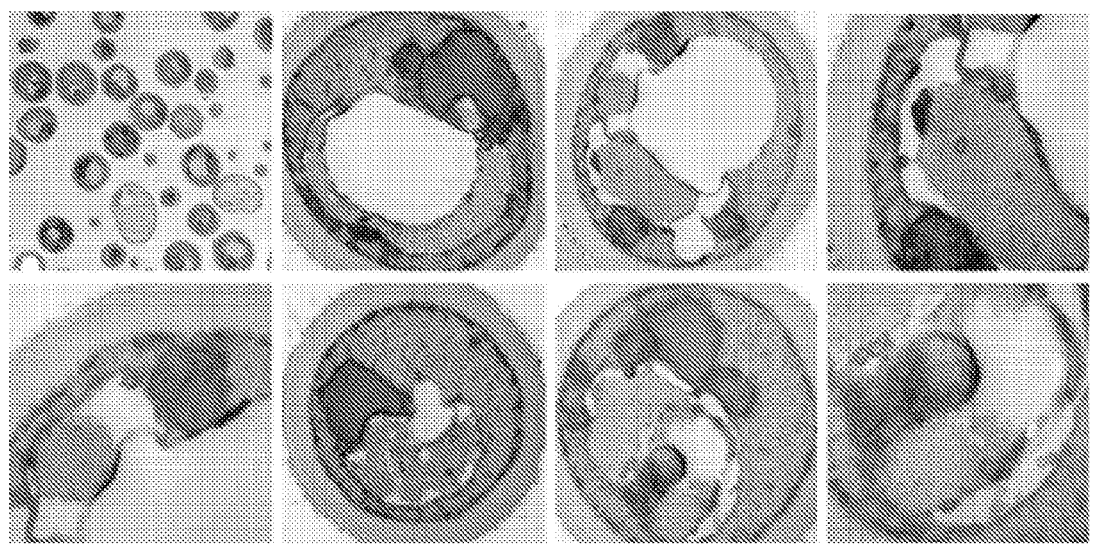
FIG. 19. Electron micrographs of *D. hansenii* cells derived from wortmannin-treated 120 hr liquid cultures. Lipid bodies (large white inclusions) are physically separated from vacuolar and nuclear compartments. Alterations in intracellular membrane morphology (compared to control) are also observed.
Figure 20:
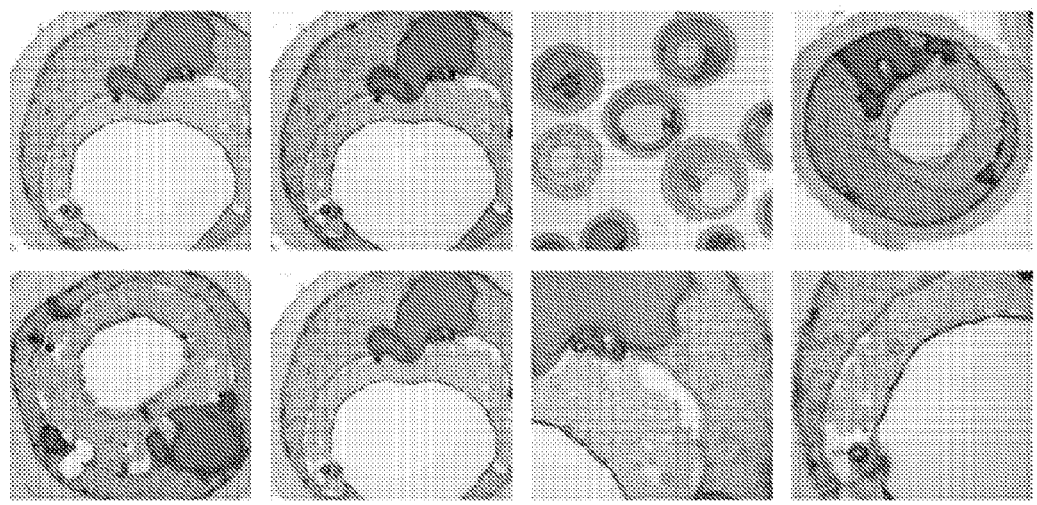
FIG. 20. Electron micrographs of *D. hansenii* cells derived from untreated 120 hr liquid cultures. Lipid bodies (large white inclusions) are physically separated from vacuolar and nuclear compartments. In addition, the data demonstrate an increase in intracellular lipid over time in this medium (glucose containing minimal medium).
Figure 21:
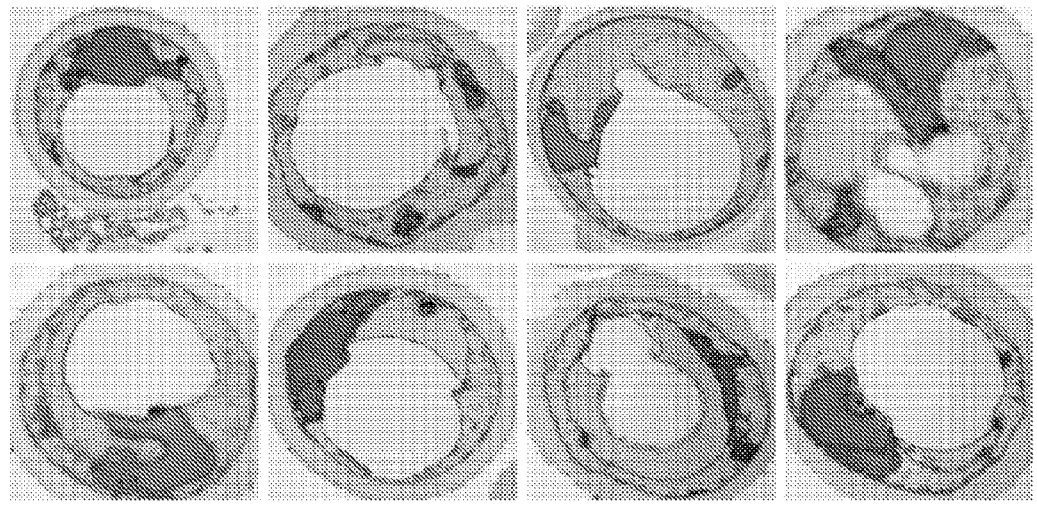
FIG. 21. Electron micrographs of *D. hansenii* cells derived from wortmannin-treated 192 hr liquid cultures. Lipid bodies (large white inclusions) are physically separated from vacuolar and nuclear compartments. Alterations in intracellular membrane morphology (compared to control) are also observed.
Figure 22:
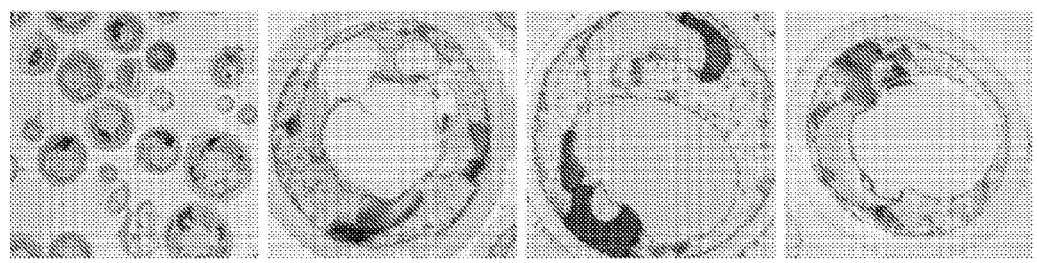
FIG. 22. Electron micrographs of *D. hansenii* cells derived from untreated 192 hr liquid cultures. Lipid bodies (very large white inclusions) remain physically separated from vacuolar and nuclear compartments. In addition, the data demonstrate an increase in intracellular lipid over time in this medium (glucose containing minimal medium).

In an exemplary embodiment of this invention, *D. hansenii* produces large amount of oils when grown under conditions of nitrogen starvation or nitrogen limitation. Electron microscopy could be used to verify oil accumulation by cells under low nitrogen conditions. Electron micrographs were taken for *D. hansenii* cells grown at 30° C. in Medium A with glucose (30 g/L) under low nitrogen conditions (0.1 g/L) with or without 100 nM wortmannin treatment (a PI-3 kinase inhibitor) for 48 hr (FIGS. 17 and 18), 120 hr (FIGS. 19 and 20) and 192 hr (FIGS. 21 and 22) post inoculation. In both wortmannin-treated and untreated cells, intracellular lipid bodies enlarged over time, but remained physically separated from vacuolar and nuclear compartments. Wortmannin-treated cells had alterations in the intracellular membrane morphology that are distinct from the untreated cells (FIGS. 17, 19 and 21). FIG. 17. Electron micrographs of *D. hansenii* cells derived from wortmannin-treated, 48 hr liquid cultures. Lipid bodies (large white inclusions) are physically separated from vacuolar and nuclear compartments. FIG. 18. Electron micrographs of *D. hansenii* cells derived from untreated 48 hr liquid cultures. Lipid bodies (large white inclusions) are physically separated from vacuolar and nuclear compartments. FIG. 19. Electron micrographs of *D. hansenii* cells derived from wortmannin-treated 120 hr liquid cultures. Lipid bodies (large white inclusions) are physically separated from vacuolar and nuclear compartments. Alterations in intracellular membrane morphology (compared to control) are also observed. FIG. 20. Electron micrographs of *D. hansenii* cells derived from untreated 120 hr liquid cultures. Lipid bodies (large white inclusions) are physically separated from vacuolar and nuclear compartments. In addition, the data demonstrate an increase in intracellular lipid over time in this media (glucose containing rich medium). FIG. 21. Electron micrographs of *D. hansenii* cells derived from wortmannin-treated 196 hr liquid cultures. Lipid bodies (large white inclusions) are physically separated from vacuolar and nuclear compartments. Alterations in intracellular membrane morphology (compared to control) are also observed. FIG. 22. Electron micrographs of *D. hansenii* cells derived from untreated 196 hr liquid cultures. Lipid bodies (very large white inclusions) remain physically separated from vacuolar and nuclear compartments.

Figure 23:
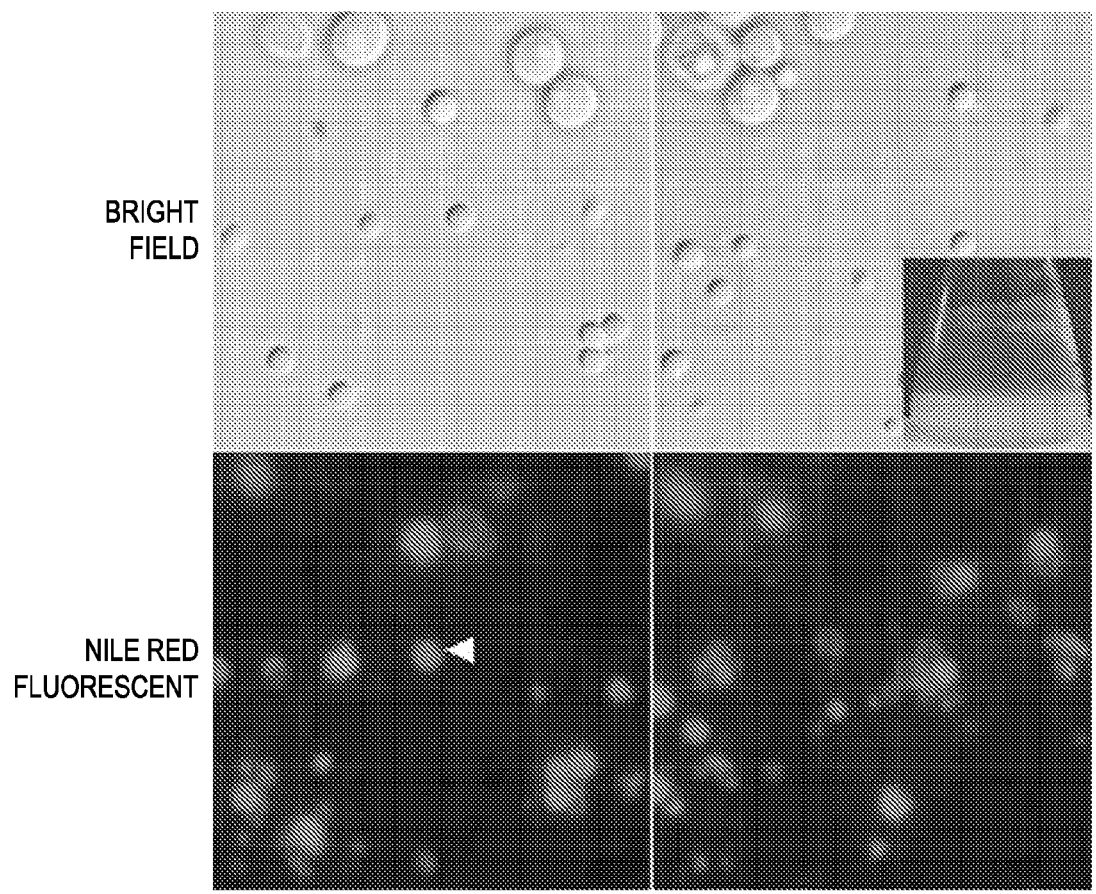
FIG. 23. Extracellular vesicles from cultures of *D. hansenii* were stained with Nile red and observed under the fluorescent microscope. Insets: release of hydrophobic materials attached to the glass wall from culture of *D. hansenii* in medium A containing 30 g/L of glucose and 0.1 g/L $NH_4Cl$.

Importantly, it was found that nitrogen starvation promoted extracellular oil accumulation. In particular, a portion of the oils synthesized by *D. hansenii* was found in the extracellular fraction after growth under these conditions. In glass flasks with *D. hansenii* cultures, a thin layer of hydrophobic materials was attached to the hydrophobic wall (inset FIG. 23). Liquid cultures of *D. hansenii* were stained with Nile red and observed under a fluorescent microscopy, and fluorescent vesicles containing lipids were observed in the culture medium (FIG. 23). [FIG. 23. Extracellular vesicles (arrow head) from cultures of *D. hansenii* were stained with Nile red and observed under the fluorescent microscope. Insets: release of hydrophobic materials attached to the glass wall from culture of *D. hansenii* in medium A containing 30 g/L of glucose and 0.1 g/L $NH_4Cl$.

Figure 24:
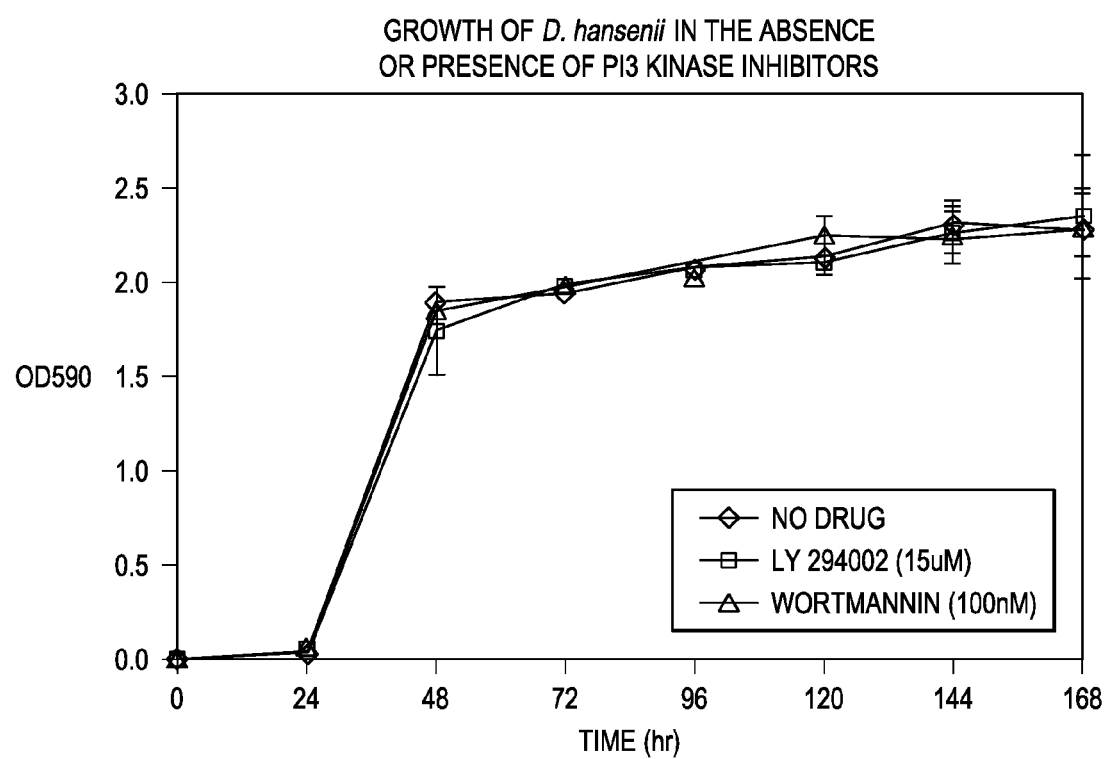
FIG. 24. Growth of *D. hansenii* in the absence and presence of PI-3 kinase inhibitors LY 294002 and wortmannin.
Figure 25A:
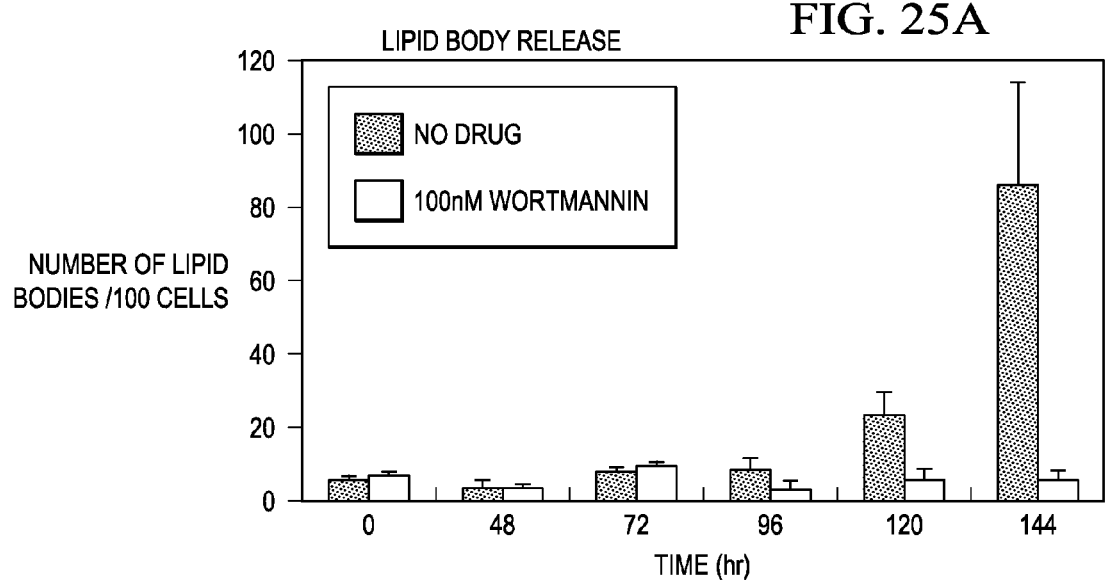
FIG. 25. Secretion of lipid by *D. hansenii*. Treatment of 100 nM wortmannin reduced the number of extracellular lipid bodies (A) while the percentage of viable cells (B) was not affected. Cell viability was determined by FUN1 stain and microscopic observation and quantifications. The data demonstrate the secretion of lipid bodies by the yeast.
Figure 25B:
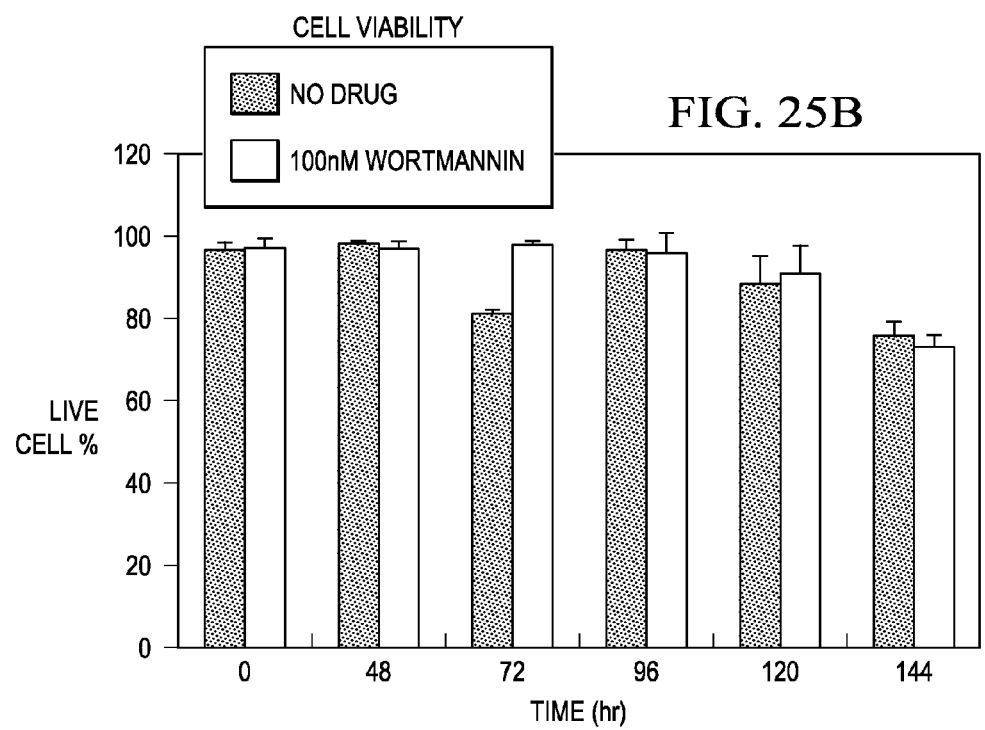
Figure 26A:
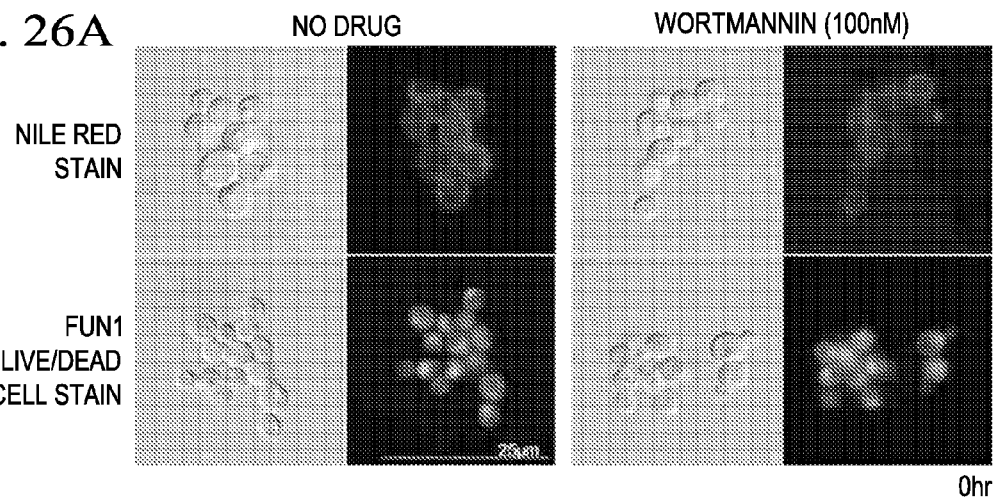
FIG. 26. Time course of lipid secretion by *D. hansenii* demonstrates that lipid secretion requires PI-3 kinase activity. Treatment of 100 nM wortmannin reduced the number of extracellular lipid bodies over a time course of treatment. However, cell viability was not affected. Cell viability was determined by FUN1 stain and microscopic observation and quantification. The data demonstrate the secretion of lipid bodies by the yeast. A. 0 hr, B. 48 hr, C. 96 hr, D. 120 hr, E. 144 hr.
Figure 26B:
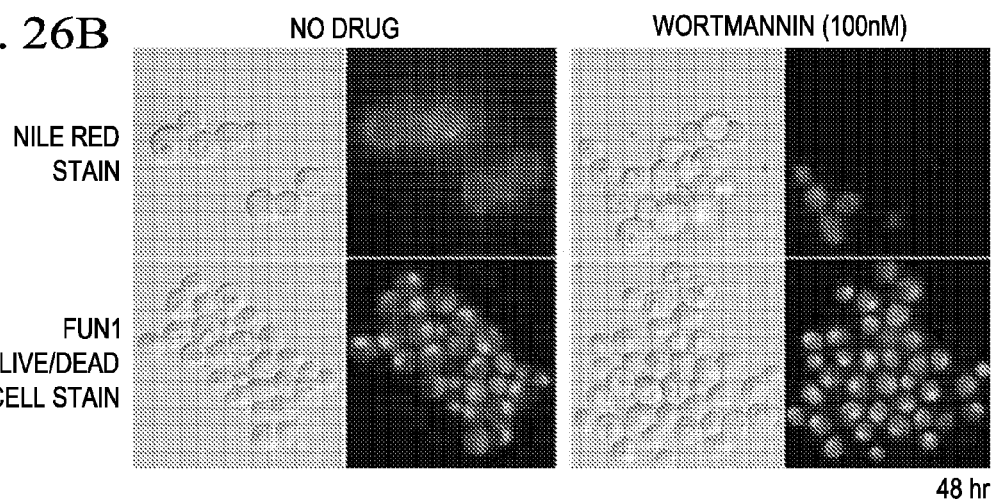
Figure 26C:
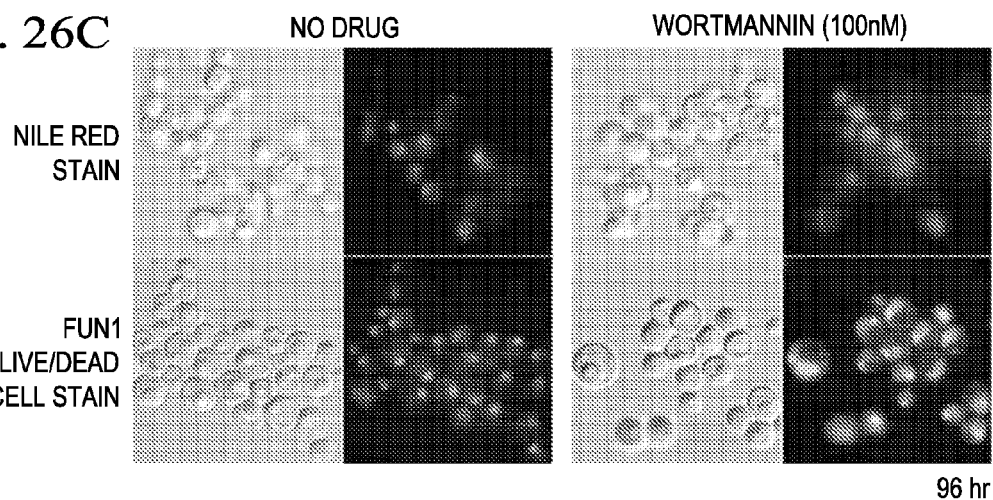
Figure 26D:
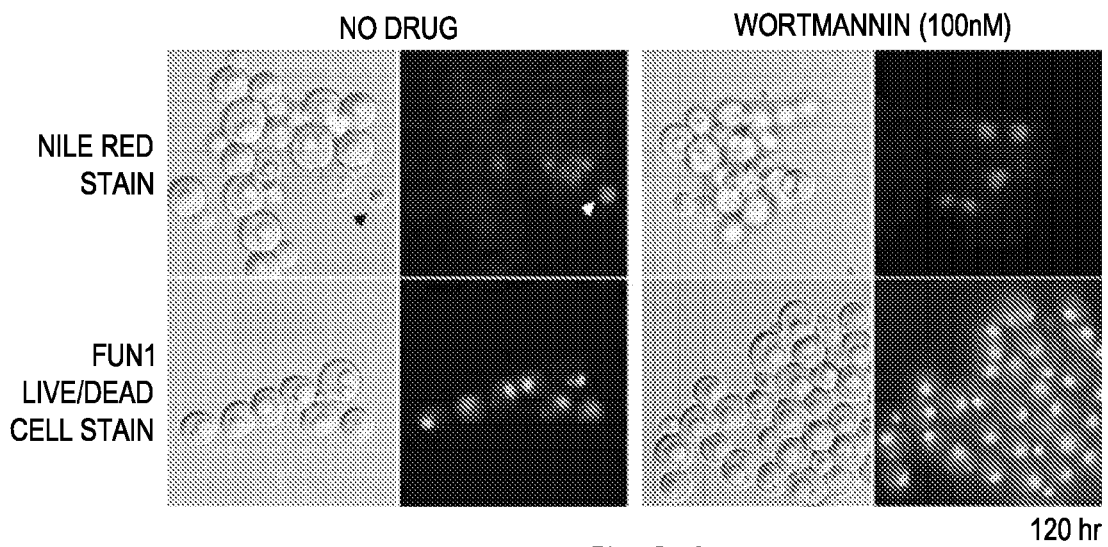
Figure 26E:
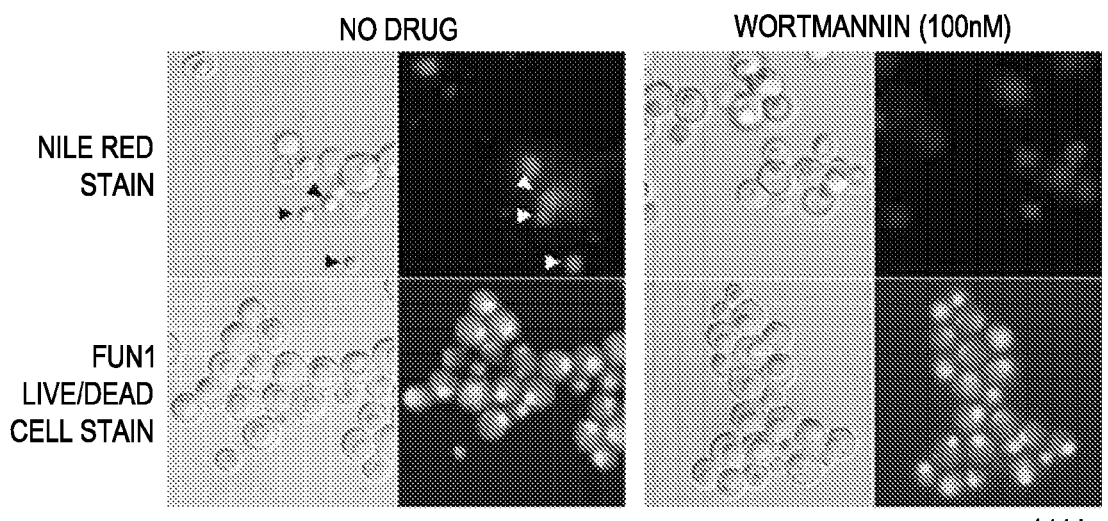

The lipid body release was determined microscopically. Low concentrations of wortmannin (100 nM) and LY 294002 (15 µM), two PI-3 kinase inhibitors, both failed to affect the growth of *D. hansenii* in medium A with glucose under low nitrogen conditions (FIG. 24). However, the lipid bodies released from *D. hansenii* cells treated with wortmannin significantly reduced to lower than 10 per 100 cells at 144 hr post inoculation, comparing to more than 80 per 100 cells from the untreated control cells (FIG. 25A, FIG. 26A-E). Meanwhile, the cell viabilities remained unaffected (FIG. 25B, FIG. 26A-E). These results indicated that the lipid body release we observed was rather an active and wortmannin-responsive process than a cell lysis related phenomenon. FIG. 24. Growth and lipid accumulation of *D. hansenii* in the absence and presence of PI-3 kinase inhibitors LY 294002 and wortmannin. FIG. 25. Secretion of lipid by *D. hansenii*. Treatment of 100 nM wortmannin reduced the number of extracellular lipid bodies (A) while cell viability (B) were not affected. Cell viability was determined by FUN1 stain and microscopic observation and quantifications. The data demonstrate the secretion of lipid bodies by the yeast. FIGS. 26A-26E. Time course of lipid secretion by *D. hansenii* demonstrates that lipid secretion requires PI3 kinase activity. Treatment of 100 nM wortmannin reduced the number of extracellular lipid bodies over a time course of treatment. However, cell viability was not affected. Cell viability was determined by FUN1 stain and microscopic observation and quantification. The data demonstrate the secretion of lipid bodies by the yeast. 26 A. 0 hr, 26 B. 48 hr, 26 C. 96 hr, 26 D. 120 hr, and 26 E. 144 hr.

In one embodiment of the present invention, specific fractions of oils are secreted. *D. hansenii* was used as an exemplary microbe to examine accumulation and secretion of lipid bodies. It should be emphasized however that the present invention is not limited to this microbial species.

Lipid body secretion was examined in *D. hansenii* in low nitrogen medium A, grown for 5 days at 28° C., 250 rpm. Different fractions of the cultures were extracted and analyzed for the presence of the lipid and proteins structures. It was determined whether the organism was capable of displaying specificity in the species of secreted/extracellular lipids structures, that is, whether the secreted fraction had a different composition than the non-secreted counterpart. Demonstration of such specificity reduces to practice whereby "designer" oils/lipids can be synthesized and secreted. These designer oils can be optimized for specific applications, including but not limited to transportation fuels, lubricants, solvents, and synthetic precursors to complex polymer synthesis.

Figure 27:
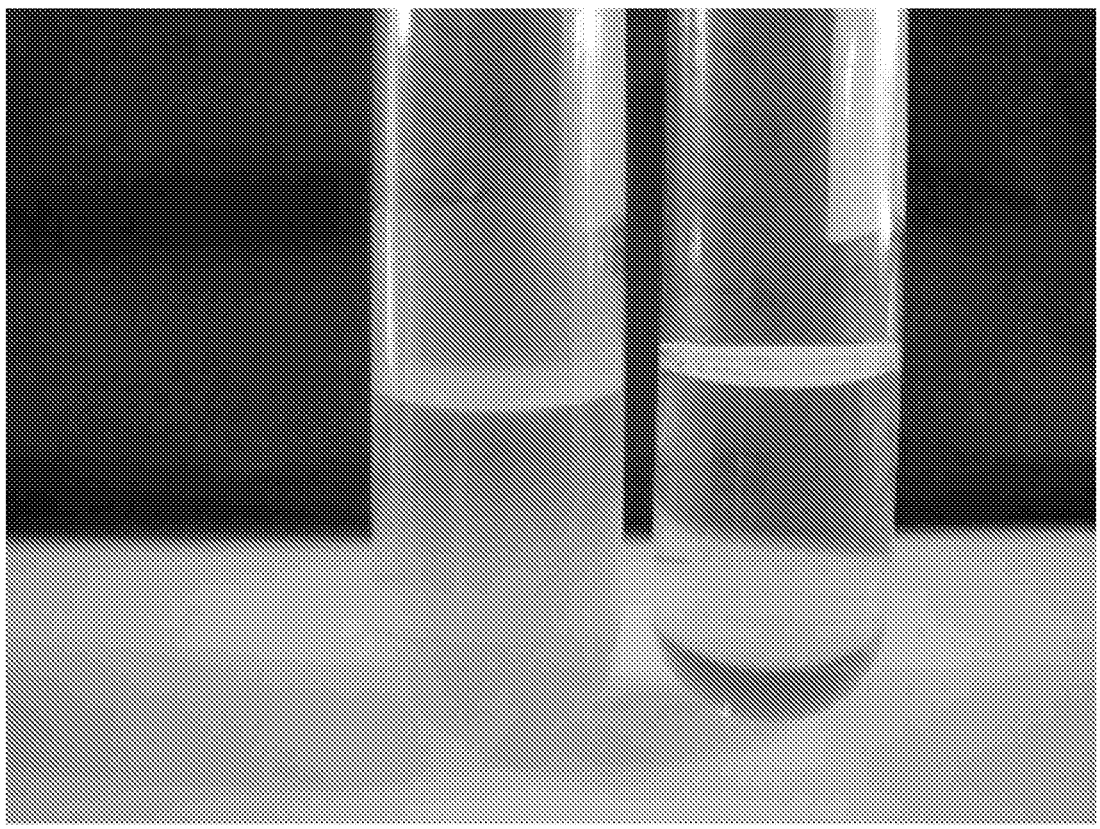
FIG. 27. Formation of the lipid film on the tube wall of *D. hansenii* culture. Day-1 culture. Right tube holds the blank culture (medium A only).

There was hydrophobic film formation on the surface of the liquid cultures throughout the 5-day growth suggesting extracellular lipid bodies. This film tended to stick to the side walls of the growth tube as well as forming an easily separable layer at the surface of the culture solution (FIG. 27). These fractions were extracted for both lipids and proteins.

Figure 28:
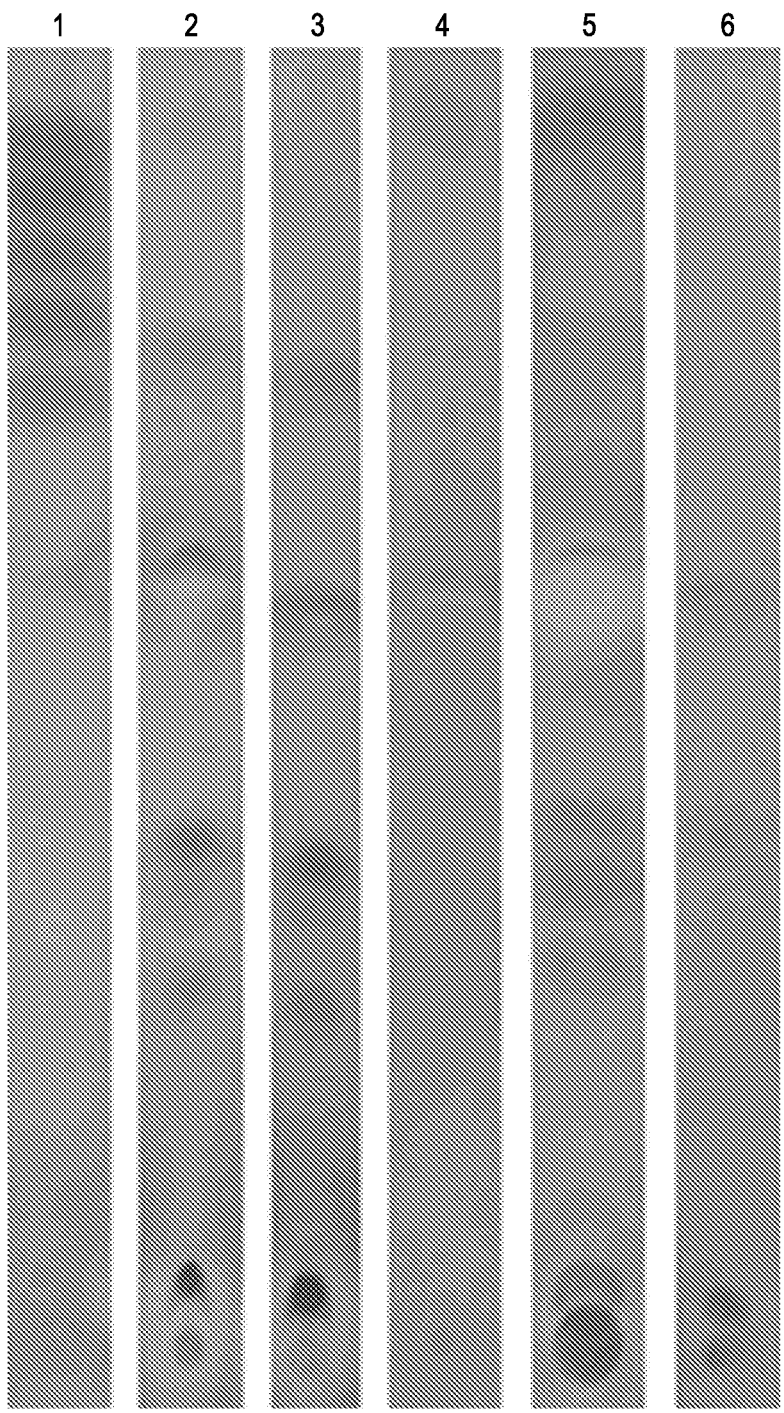
FIG. 28. Lipid composition of secreted TAGs is different from bulk cellular lipid. HPTLC profiles of lipid from secreted and non-secreted fractions demonstrate differential species present in each fraction. Six parallel cultures were processed. *D. hansenii* cultures were grown to high density (OD600>>1.5). The cultures were then diluted in low nitrogen medium N (OD600 0.05) and grown for 5-7 days. Next, cell pellets and supernatant were removed by pipetting out, a film layer on the tube walls remained. The tube walls were washed with fresh medium A 3-5 times. The pellet was separated from supernatant by centrifugation. Each fraction (pellet, supernatant, and film on the tube walls) was extracted for lipids as described in the figures. The same fractions were extracted for proteins from similarly grown cultures. Protein bands were observed in tube wall films and in the pellet but not in the supernatant. These data therefore indicated a specific (i.e., non-lytic) process for lipid secretion.

TLC of different fractions of *D. hansenii* cultures was demonstrated in FIG. 28. In TLC using a hexane:diethyl ether:acetic acid system, simple lipids such as triglycerides and free fatty acids moved with the mobile phase whereas complex lipids stayed at the origin. TLC showed the presence of lipids both in the supernatant and in the hydrophobic film on the surface of the culture. These data indicated that the lipid bodies were in fact secreted out of the cell during cultivation. Although all fractions show the presence of lipids, differences were noted in the type and the density of the lipids present in each fraction. To determine the identity ratio of the lipids in each fraction, further analysis like HLPC is required. Nevertheless, in the implication is clear to one skilled in the art, namely, that the secretion process is such that the lipid composition of the secreted fraction is different from the composition of the non-secreted counterpart. Therefore, the process is specific, and can be engineered for designer oil/lipid secretion. FIG. 28. Lipid composition of secreted TAGs is different from bulk cellular lipid. TLC profiles of lipid from secreted and non-secreted fractions demonstrate differential species present in each fraction. Six parallel cultures were process. D. hansenii cultures were grown to high density (OD600>>1.5). The cultures were then diluted in low nitrogen medium N (OD600 0.5) and grown for 5-7 days. Next, cell pellets and supernatant removed by pipetting out, a film layer on the tube walls remained. The tube walls were washed with fresh medium A 3-5 times. The pellet was separated from supernatant by centrifugation. Each fraction (pellet, supernatant, and film on the tube walls) was extracted for lipids as described in the figures. The same fractions were extracted for proteins from similarly grown cultures. Protein bands were observed in tube wall films and in the pellet but not in the supernatant. These data therefore indicated a specific (i.e., non-lytic) process for lipid secretion. 1. TAG Markers (10-20 ng); 2. $CHCl_3$-MeOH soluble Part of the film on the tube walls; 3. $CHCl_3$-MeOH soluble Part of the supernatant; 4. $CHCl_3$-MeOH soluble part of the tube walls after it is washed with protein extraction buffer; 5. $CHCl_3$-MeOH soluble part of the cell pellet; 6. $CHCl_3$ soluble part of the after it is washed with $CHCl_3$-MeOH.

In C. neoformans, the exocytosis of capsular polysaccharides and other macromolecules has been described. In S. cerevisae, extracellular secretion of free fatty acids has also been described. In animals, cytosolic neutral lipid droplets consist of a core of TAG that is surrounded by a surface monolayer of phospholipids and proteins. Protein binding to lipid bodies during yeast development is discussed and the importance of lipid bodies in biosynthesis, mobilization and cellular trafficking has been documented.

Thus, in D. hansenii, where lipids bodies are secreted out of the cell, it is important to understand which proteins are associated with the lipid bodies. For this purpose protein extraction was performed to the same three culture fractions described for lipid extraction. Cell, supernatant and lipid film fractions of the 5-day culture were extracted (50 mM Tris-HCl, 2.0 mM DTT, 100 mM NaCl, 14 mM Beta-mercaptoethanol) and extracted proteins were separated using 12.5% SDS PAGE. The gels showed the presence of proteins in film fraction and but not in the supernatant fraction. The cellular fraction, which was used as a positive control, also showed the presence of the protein on the gel as expected. Therefore, the lipid bodies and proteins are secreted together. Importantly, the protein fraction is specific, indicating a selective process regulating the lipid body secretion event.

It should be immediately apparent to one skilled in the art that the above example provides for a system in which the cell that secretes the oil also produces the oil. Thus, in an important embodiment of the present invention, the oil and/or lipid body secretion is achieved by an oil-producing cell. This oil-producing cell can, in one aspect of the invention, be an oil producing microbe, including but not limited to, D. hansenii.

One skilled in the art will recognize that nitrogen starvation promotes the differential expression and/or activation of autophagy associated genes and gene products [64-69], including but not limited to ATG1, ATG2, ATG3, ATG4, ATG5, ATG6, ATG7, ATG8, ATG9, ATG10, ATG11, ATG12, ATG13, ATG14, ATG15, ATG16, ATG17, ATG18, ATG19, ATG20, ATG21, ATG22, ATG23, ATG24, ATG25, ATG26, ATG27, ATG28, ATG29, ATG30, and/or ATG31. Therefore, in an important embodiment of the present invention, the activation and/or modulation of these genes (and/or gene products) is used to modulate the amount and/or specificity of lipid or oil body secretion.

One skilled in the art will recognize that nitrogen starvation promotes the differential expression and/or inactivation of cellular PI-3 kinase activities. Therefore, in an important embodiment of the present invention, the activation and/or modulation of these genes (and/or gene products) is used to modulate the amount and/or specificity of lipid or oil body secretion.

In one embodiment of the invention, the modulation of autophagy associated gene expression is achieved by using standard molecular genetic approaches to overexpress and/or knockout one or more of these genes. RNAi mediated approaches can also be employed to achieve knockdown of target autophagy associated genes.

In one embodiment of the present invention, oil and/or lipid body synthesis is achieved by growing an oil producing cell on a monosaccharide, disaccharide, and/or complex carbon source, including but not limited to a complex carbon source that contains pentose and/or hexose sugars, and/or cellulose and/or cellulose derived products.

Figure 29:
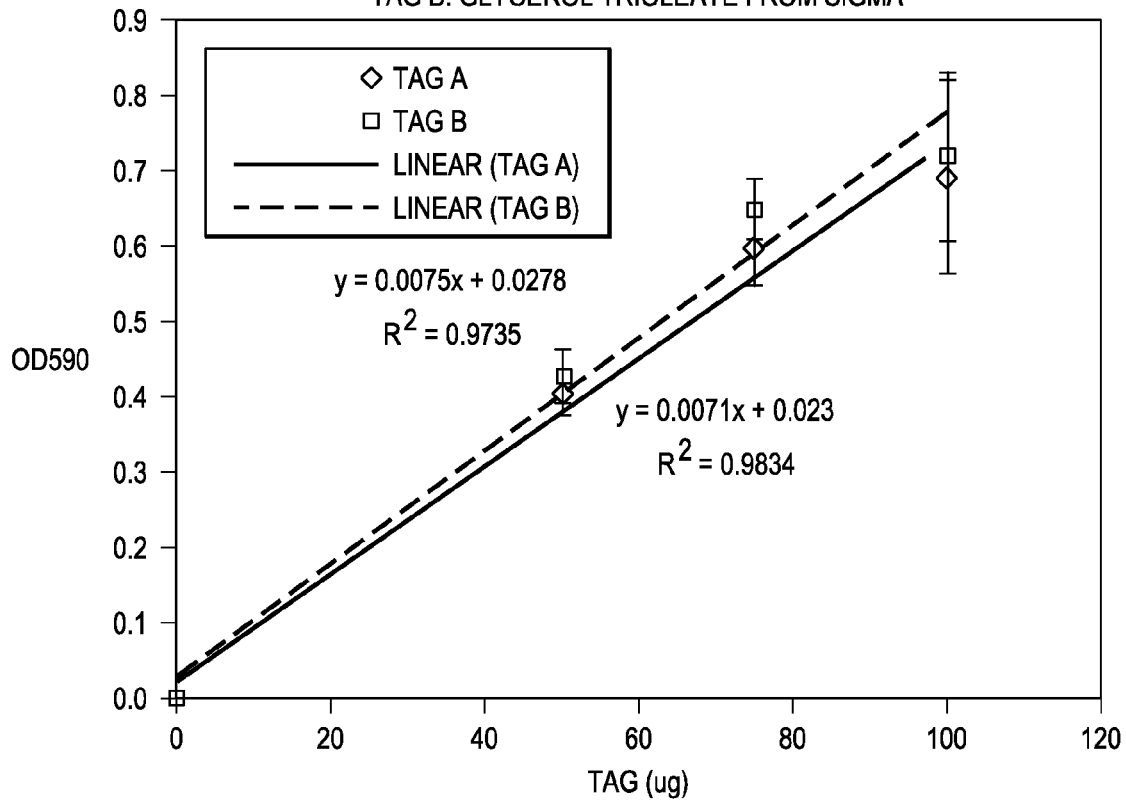
FIG. 29. An enzymatic assay to measure extracellular TAG species provides linear information over 2 logs of TAG concentrations. The enzymatic reactions convert extracellular TAGs into glycerol and then dihydroxyacetone phosphate, accompanied by the formation of hydrogen peroxide. Color reaction based on the degradation of hydrogen peroxide enables measurement with a spectrophotometer.
Figure 30A:
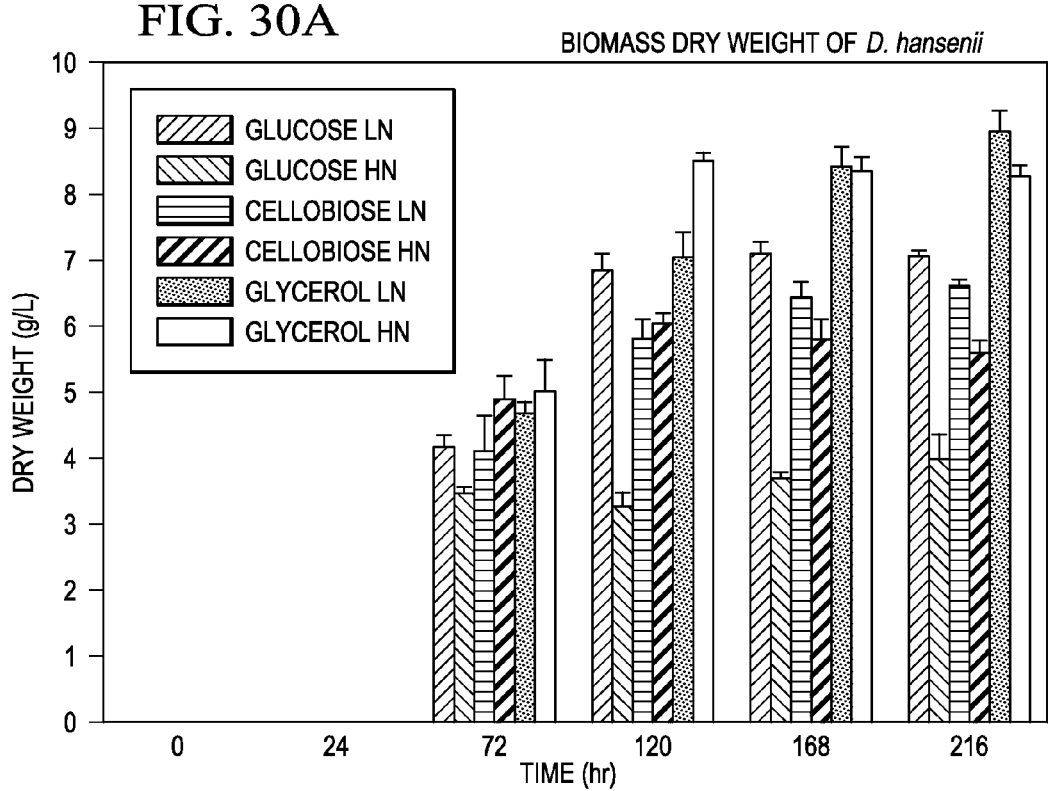
FIG. 30. An enzymatic TAG assay reveals that *D. hansenii* secretes TAG into the extracellular medium over a time course of growth in various carbon sources. The amount of TAG synthesized as a function of total cell weight (biomass) was determined (upper left). The amount of intracellular lipid, total lipid, and extracellular TAG was also measured (upper right, lower left, lower right, respectively).
Figure 30B:
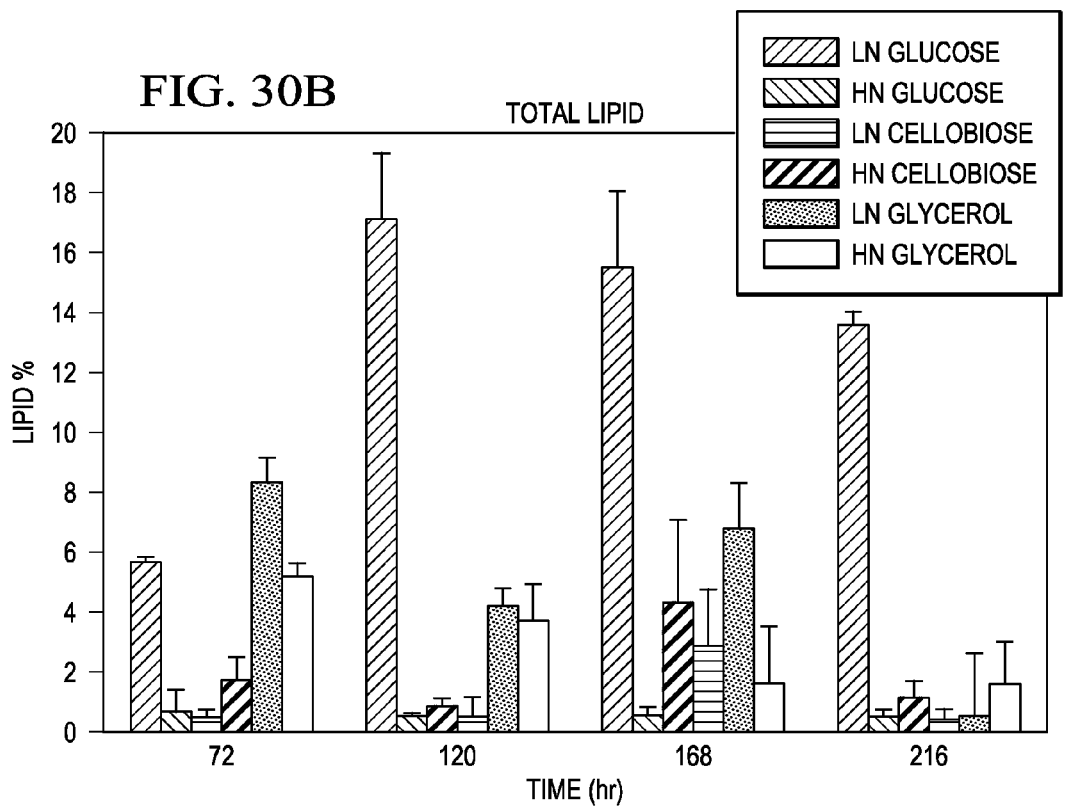
Figure 30C:
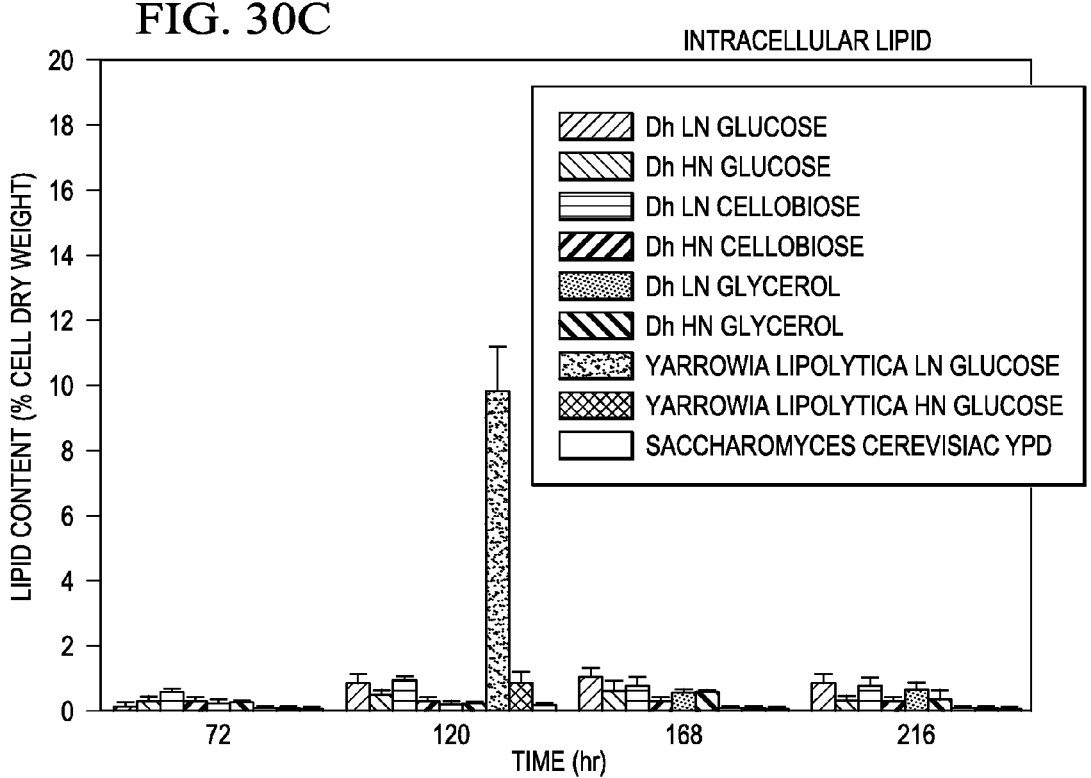
Figure 30D:
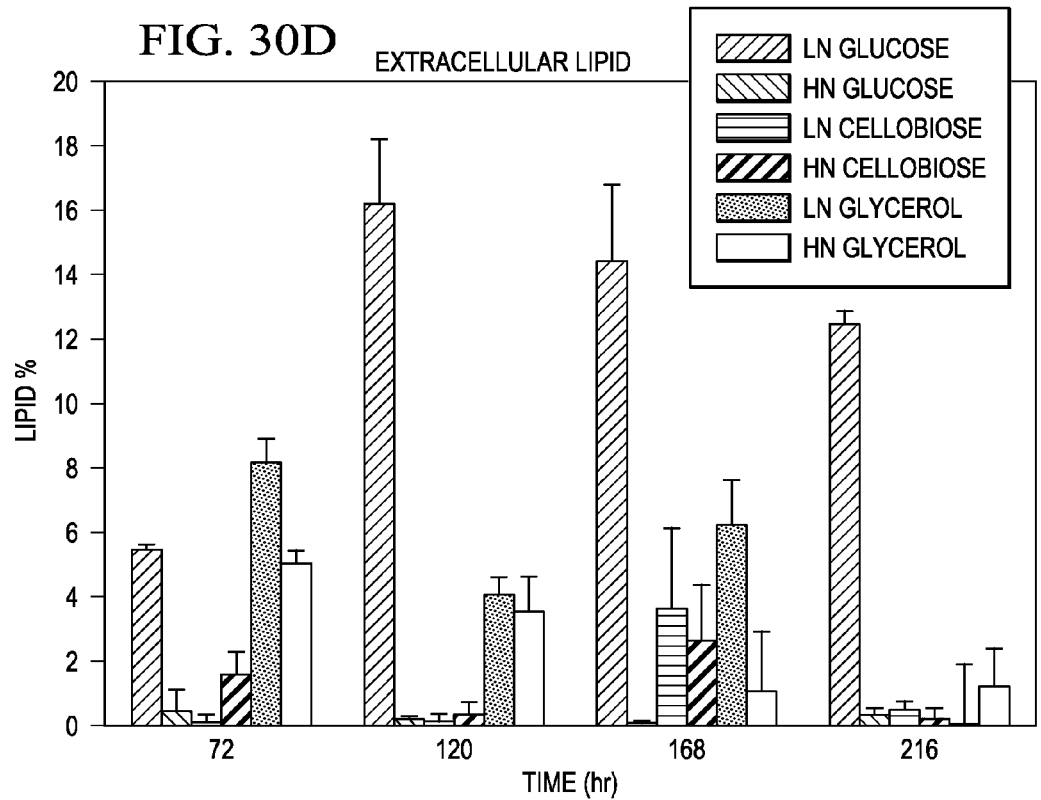

For example, D. hansenii is able to grow on assorted carbon sources including glucose, glycerol and cellobiose. The cell masses and lipid contents D. hansenii accumulated using these substrates as the pure carbon sources were quantified over a time course of growth (FIG. 30). Intracellular lipids were extracted directly from dry cells in an Accelerated Solvent Extractor (ASE) using dichloromethane as the solvent and measured gravimetrically. Extracellular triacylglycerides (TAG) were quantified using an enzymatic assay (FIG. 29) involving the following reactions catalyzed by lipase, glycerol kinase, glycerol phosphate oxidase, and peroxidase, respectively:

1. triacylglycerol+$H_2O$→>glycerol+free fatty acids
2. glycerol+ATP→>glycrol-3-phosphate+ADP
3. glycerol-3-phosphate+$O_2$→>dihydroxyacetone phosphate+$2H_2O_2$
4. $H_2O_2$+4-aminoantipyrine+3,5-dichloro-2-hydroxybenzene sulfonate→>quinoneimine dye+$2H_2O$ Clearly, the extracellular TAG accounted for majority (over 90%) of the lipids produced by D. hansenii grown in media with different carbon sources (FIG. 30). FIG. 29. An enzymatic assay to measure extracellular TAG species provides linear information over 2 logs of TAG concentrations. FIG. 30. An enzymatic TAG assay reveals that D. hansenii secretes TAG into the extracellular medium over a time course of growth in various carbon sources. The amount of TAG synthesized as a function of total cell weight (biomass) was determined (upper left). The amount of intracellular lipid, total lipid, and extracellular TAG were also measured (upper right, lower left, lower right, respectively).

Figure 31:
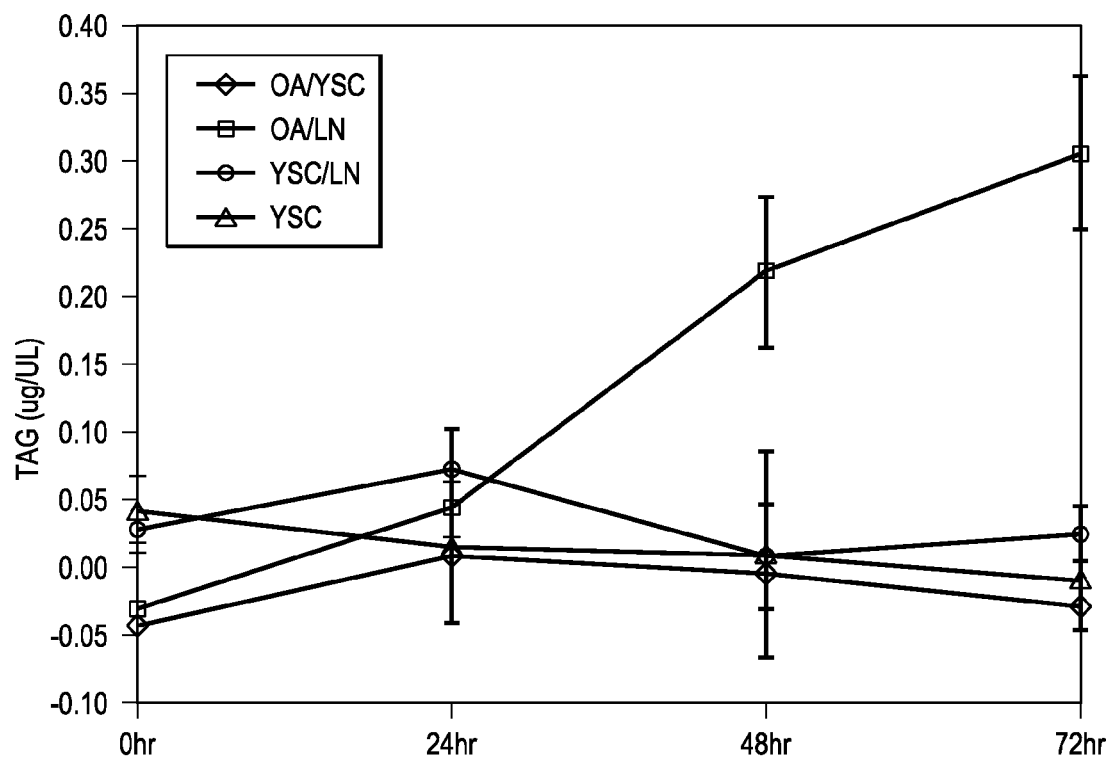
FIG. 31. *S. cerevisiae* cells were grown in synthetic medium (YSC), loaded with oleic acid (OA), switched to low nitrogen (LN) medium, and then washed with PBS. Extracellular TAG was quantified at different time points after the wash. No glycerol was detected in the extracellular lipid extract before the addition of lipase. These data indicate that oil secretion is evolutionarily conserved, and can be induced in non-oleaginous, genetically-tractable organisms. Importantly, because *S. cerevisiae* is a model for a wide variety of plant and animal secretion, these data indicate that oil secretion can be induced in both plants and animal cells.

In one embodiment, the present invention is a cell that produces and secretes TAG into the extracellular medium. In another embodiment of the invention, oil/lipid body secretion is induced to occur in non-oleaginous organisms, including non-oleaginous yeasts (e.g., S. cerevisiae). For example, to explore the possibility of using a genetically more tractable system to study the mechanism of lipid body secretion that likely caused by nitrogen starvation-induced autophagy, we tested whether *S. cerevisiae* secrets TAGs under nitrogen starvation conditions when pre-loaded with lipids (FIG. 31). While *S. cerevisiae* cells remained in nitrogen rich conditions and cells without oleic acid pre-loading did not secret TAGs, cells loaded with oleic acid produced increasing amount of TAGs extracellularly over a time course of 72 hr after transferred to nitrogen starvation medium (FIG. 31), indicating that lipid body secretion may be a general autophagy-related process induced by nitrogen starvation. FIG. 31. *S. cerevisiae* cells were grown in synthetic medium (YSC), loaded with oleic acid (OA), switched to low nitrogen (LN) medium, and then washed with PBS. Extracellular TAG were quantified at different time points after the wash. No glycerol were detected in the extracellular lipid extract before the addition of lipase. These data indicate that oil secretion is evolutionarily conserved, and can be induced in non-oleaginous, genetically-tractable organisms. Importantly, because *S. cerevisiae* is a model for a wide variety of plant and animal secretion, these data indicate that oil secretion can be induced in both plants and animal cells.

As will be apparent to one skilled in the arts, the invention has broad implications beyond oleaginous microbes, and can be readily extended—by one skilled in the arts, to other kinds organisms, including but not limited to green algae.

The present invention includes systems and methods for the conversion of short-chain carbohydrates from biofuel formation and cellulosic biomass into high-energy fuels. The present invention may be used with one or more known methods for final recovery of hydrocarbons and other lipids. The recovery of long chain fatty acids and hydrocarbons may include of one or several steps. For maximum recovery of fatty acids and hydrocarbons, water content of yeast cells may be reduced to 10-20% w/w by a suitable method. Suitable methods include oven drying, spray draying, drum drying, pneumatic flush drying and similar method used in food, feed and chemical industries. Dried cell biomass can then be ground/homogenized/sheared in the presence of organic solvent or a mixture of organic solvents. Organic solvents of choice may include hexane, mixture of hexane and ethanol, chloroform and methanol. Organic solvent (s) are separated from the lipophilic compounds (fatty acids and hydrocarbons) by evaporation to yield a solvent-free mixture of fatty acids and hydrocarbons that are further processed into biodiesel, gasoline or jet fuel.

Culture media and cultivation conditions. For liquid culture, single colony of *D. hansenii* or *S. cerevisiae* were pre-cultured in 2 mL YPD or other desired media (see below) and incubated at 30° C. for 24 hr. Cells were counted using a hemacytometer and spun down at 3000 rpm for 15 minutes. Cells at a concentration of $1\times10^6$/mL were used to inoculate the desired media with 1% of the total volume. Medium A with limited nitrogen source (glucose 30 g/L, yeast extract 1.5 g/L, $NH_4Cl$ 0.1 g/L, $KH_2PO_4$ 7.0 g/L, $Na_2HPO_4$ 1.983 g/L, $MgSO_4.7H_2O$ 1.5 g/L, $FeCl_3.6H_2O$ 0.08 g/L, $ZnSO_4.7H_2O$ 0.01 g/L, $CaCl_2.2H_2O$ 0.1 g/L, $MnSO_4.H_2O$ 0.07 mg/L, $CuSO_4.5H_2O$ 0.1 mg/L, $Co(NO_3)_2.6H_2O$ 0.1 mg/L, pH 5.5; see Kimura et al., 2004) was used to support the growth of *D. hansenii* and induce cellular lipid accumulation. Medium A with sufficient nitrogen supply ($NH_4Cl$ 5 g/L) was used to support growth without the induction of lipid accumulation. For wortmannin treatment experiment, 100 nM wortmannin (Sigma) were amended in the liquid media at 24 hr post inoculation.

Electron microscopy of *D. hansenii*. *D. hansenii* cells were grown in 150 mL Medium A containing glucose (30 g/L) as the pure carbon source with or without the presence of 100 nM wortmannin. At 48, 120 and 192 hr post inoculation, 50 mL of the culture were removed and centrifuged at 4000 rpm for 10 min. Cell pellet were fixed following the procedure described previously (Wright, 2000) and transmission electron microscopy was performed. Cell cultures were grown in triplicate.

Fluorescent microscopy. For Nile red stained cells or cultures, microscopic photographs were taken with an Olympus BX51 microscope (Olympus America, New York, USA) equipped with an Olympus DP70 camera using a 530-550 nm excitation filter, a 570 nm diachronic mirror and a 590 nm emission filter with a 60× objective lens. For microscopic quantification of secreted lipid bodies, 50 µL of the cell suspension in media A containing 0.2% agarose and Nile red, with or without the addition of 100 nM wortmannin, were inoculated in triplicate in microscopic frames that allow the agarose-based matrix to be sealed between two pieces of cover glasses. Slides were incubated in 90% moisture at 30° C. At 0, 48, 72, 96, 120, 144 hr post inoculation, the number of the cells and extracellular lipid bodies (stained with Nile red) were quantified. In parallel, the cells were stained with FUN1 (Invitrogen) for viability determination.

Extracellular triacylglyceride extraction and quantification. Cell culture supernatant was collected at different time points and extracellular TAGs were extracted from 400 µL of supernatant each sample and quantified as described (Schwartz and Wolins, 2007). Experiments were performed in triplicate.

Intracellular lipid extraction and quantification. *D. hansenii* cells were collected from 50 mL cultures at various time points and lyophilized. After dry cell weight determination, intracellular total lipids were extracted from the cells using an Accelerated Solvent Extractor (ASE) in dichloromethane with the 2 cycles of the following program at 1500 psi and 100° C.: heat for 5 min, static for 5 min, flush with 30% solvent, purge for 1 min. The solvent containing lipids were collected, dried and lipid contents were measured gravimetrically. All experiments were performed in triplicate.

Nitrogen starvation induced lipid secretion in *S. cerevisiae*. *S. cerevisiae* cells were grown in synthetic medium (YSC: 6.7 g/L yeast nitrogen base, 20 g glucose, and amino acids), loaded with oleic acid (OA), switched to low nitrogen synthetic medium (1.7 g/L yeast nitrogen base without ammonium sulfate, 20 g glucose and amino acids), and then washed with phosphate buffer saline (PBS). Extracellular TAGs were quantified at different time points after the wash. All experiments were performed in triplicate.

Lipid and protein extraction from different fractions. Experiments were performed with 6 parallel cultures. Briefly, twelve 3.0 mL low-nitrogen medium A cultures were inoculated with *D. hansenii* from a previously grown *D. hansenii* YPD plate. They were grown for 5 days at 28° C., 250 rpm, and then centrifuged at 2500 g for 5 min. Six of the twelve cultures were transferred into 1.5 mL Eppendorf tubes by pipetting out the clear supernatant together with cell pellet. A lipid film remained on the side wall of the falcon tube (which was used for extraction, see below). Care was taken not to contaminate the film on the sides of the tube while transferring the supernatant and the pelleted cells out. The falcon tubes were washed with 3×500 µL fresh medium A without disturbing the lipid film on the side wall of the tube. The wash solution was then discarded. The lipid film was extracted from the side wall, as well as from the pelleted cells and the supernatant for lipids. For the lipid film, 200 µL $CHCl_3$: MeOH (2:1, v/v) were added to the tube, vortex well, and centrifuged to precipitate any debris at 4000 rpm for 10 min.

Transfer the supernatant into a new tube, use empty tubes for further extraction, evaporate the solvent, disperse the remaining content in 10 μL CHCl$_3$ and ran 2.0 μL on TLC plate. Alternatively, we took the tubes after CHCl$_3$:MeOH treatment (still there was some film on the side walls), added 100 μL CHCl$_3$, vortexed well, transferred it to a fresh tube, evaporated the CHCl$_3$, and dispersed the tube contents in 10 μL CHCl$_3$, and run 2.0 μL on TLC plate. For the supernatant and cell fractions, we took the tube containing supernatant cell separated from the lipid film, centrifuged at 4000 rpm for 15 min, separated the supernatant into a new tube, and used this in downstream extractions (See below). Alternatively, we added 500 μL CHCl$_3$: MeOH (2:1, v/v) to the pellet, vortexed well, centrifuged to separate any cell debris, transferred the supernatant into a new tube, evaporated the supernatant and dispersed the tube contents in 10 μA, CHCl$_3$, and ran 2.0 μA, on TLC plate (See image D). Alternatively, 500 μA, were pipetted of 3.0 mL supernatant separated from the cell pellet, added 500 μL CHCl$_3$:MeOH (2:1, v/v), spun the sample as above, separated the bottom layer into a new tube, evaporated and dispersed the tube contents in 10 μL CHCl$_3$, and ran 2.0 μL on TLC plate (Sample Set 3, FIG. 28). The remaining 6 tubes were centrifuged, and pipetted clear supernatant together with cell pellet to new tubes. A lipid film remained on the side wall of the falcon tube as described above. We were careful not to contaminate the film on the sides of the tube while transferring the supernatant and the pelleted cells to a new tube. A protein extraction buffer was added, vortexed well, and centrifuged again. The supernatant were separated and added 200 μL CHCl$_3$: MeOH (2:1, v/v), centrifuged at 4000 rpm for 15 min, separated the bottom layer of the liquid part into a new tube. Finally, we evaporated and dispersed the tube contents in 10 μL, CHCl$_3$, and run 2.0 μL, on TLC plate. The results of these studies are shown in FIG. 28.

Example 3

D. hansenii growth study in PM Plates

Phonemics, an emergent scientific discipline within systems biology, is the study of global phenotypes resulting from interactions between a genome and its environment. The OmniLog Phenotype Microarray (PM) (Biolog, Hayward, Calif.) provides phonemic data by simultaneously assaying multiple cellular responses to a number of physiochemical stimuli and as a function of time. Exemplary chemical stimuli include chemical sensitivity or the ability to catabolize various carbon or nitrogen compounds. This assays indirectly measures the generation (or subsequent utilization) of cellular reducing power (e.g., NADH) by directly measuring the pixel intensity of one or more redox-responsive colorimetric dyes, which are converted from colorless to colored (e.g., purple) when reduced. Colorimetric pixel density is converted to arbitrary units (AU), such higher AU signal values are indicative of greater relative cellular respiration or activity.

PM was previously employed to characterize S. cerevisiae peptide catabolism. Herein, we use PM as a tool to determine responsiveness of D. hansenii to various physiochemical stimuli that are known to inhibit other fermentation inhibitors (e.g., pH, salts) and thus to define conditions under which D. hansenii could optimally produce and/or secret oil. In this current example, D. hansenii was assayed using four different 96-well PM panels: PM1 and PM2 (carbon source utilization and/or sensitivity); PM9 (osmolytes); and PM10 (pH).

Figure 32:
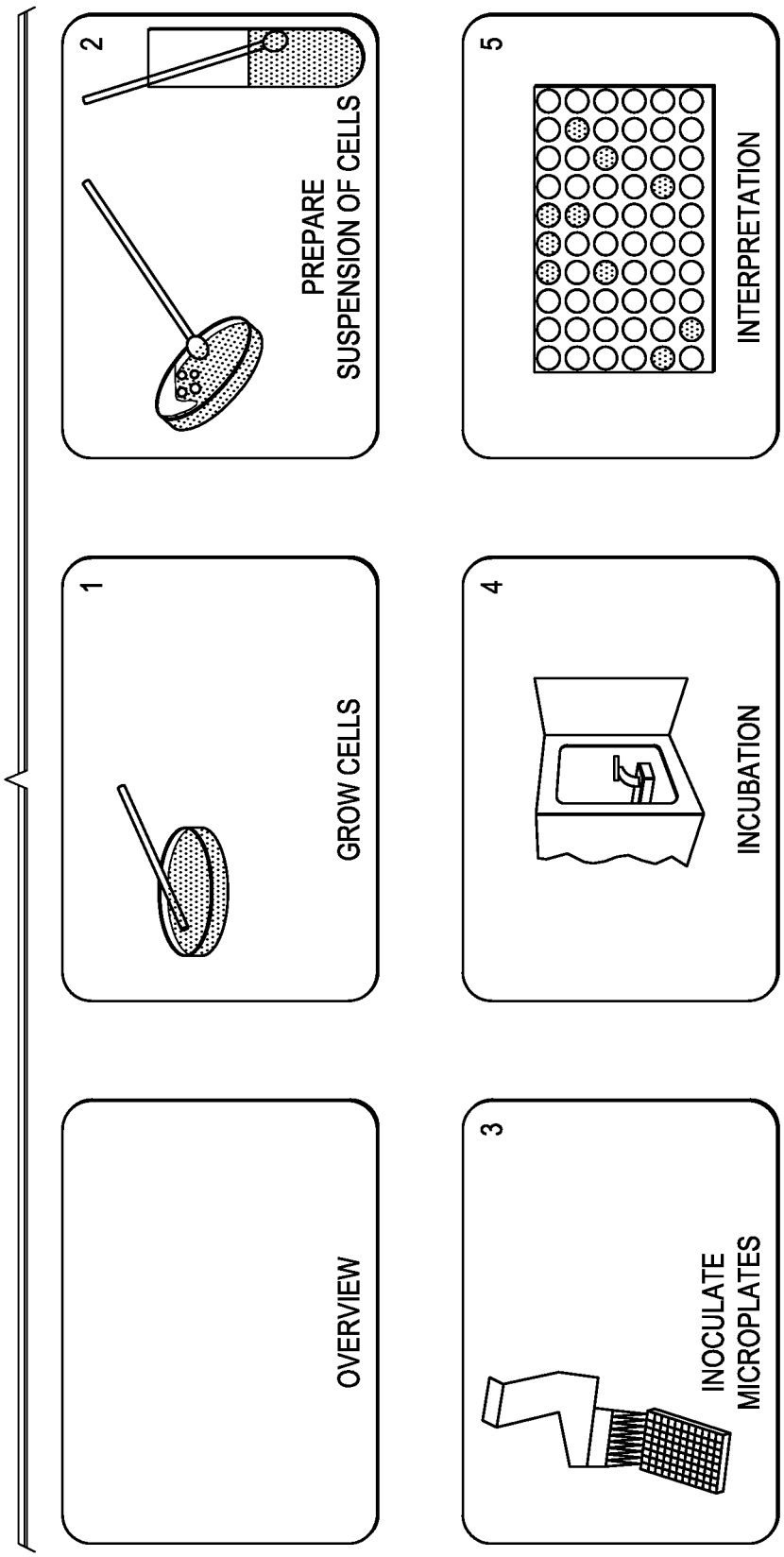
FIG. 32. Phenotype Microarray (PM) strategy. Phenotype microarrays were used to define conditions under which *D. hansenii* optimally secreted oil. The strategy for PM analysis is depicted.

In one embodiment of the present invention, optimal conditions under which oil synthesis, accumulation and secretion are defined. For example, to optimize the growth conditions at which D. hansenii secrets lipid bodies, we first investigated carbon utilization profiles and osmo- and pH-tolerance of D. hansenii using the Phenotype Microarray (PM) (FIG. 32). [FIG. 32. Phenotype Microarray (PM) strategy. Phenotype microarrays were used to define conditions under which D. hansenii optimally secreted oil. The strategy for PM analysis is depicted.]

Figure 33:
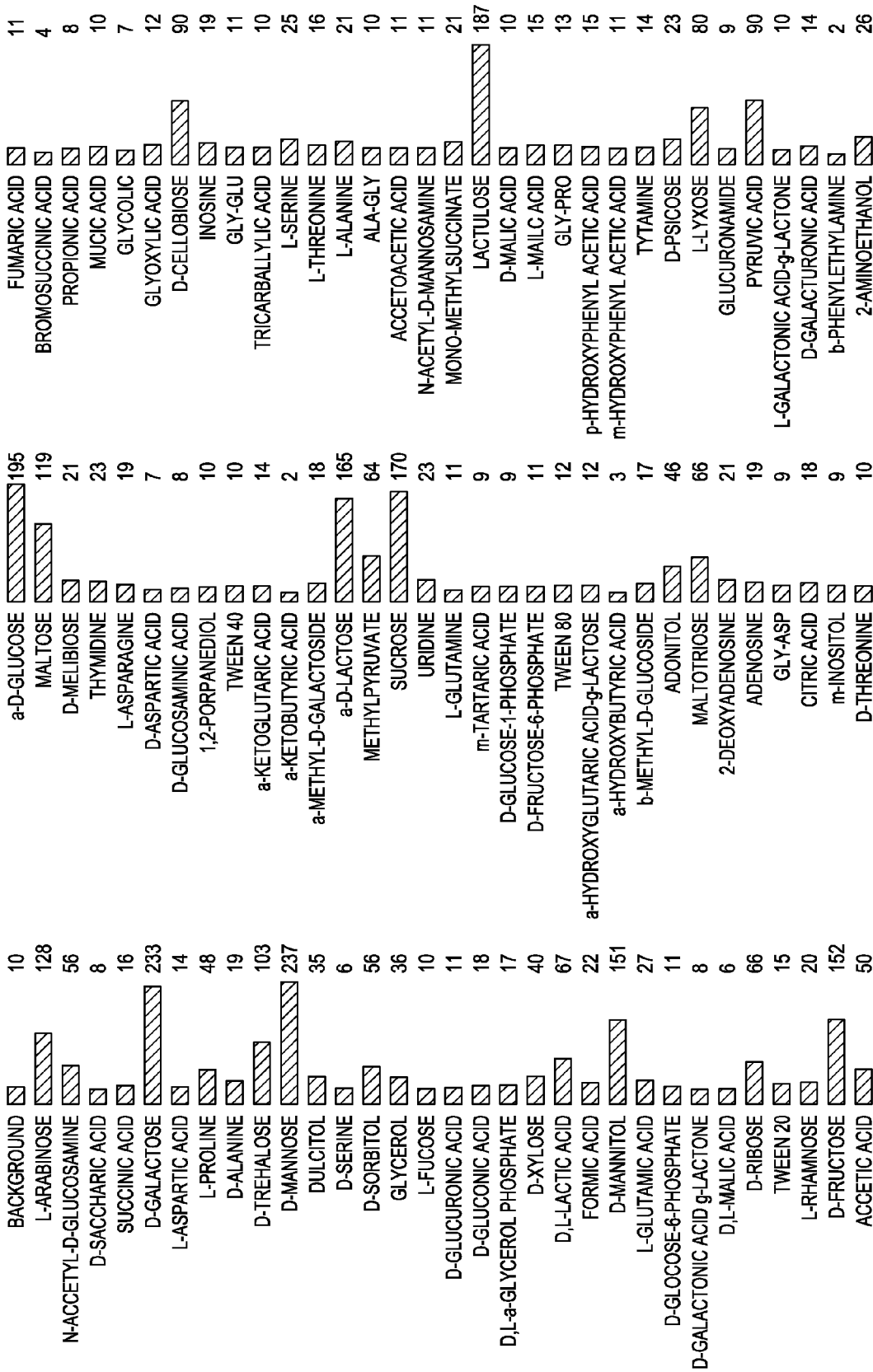
FIGS. 33 and 34. Growth of *D. hansenii* in the presence of various carbon sources (as measured using the OMNILOG PM).
Figure 34:
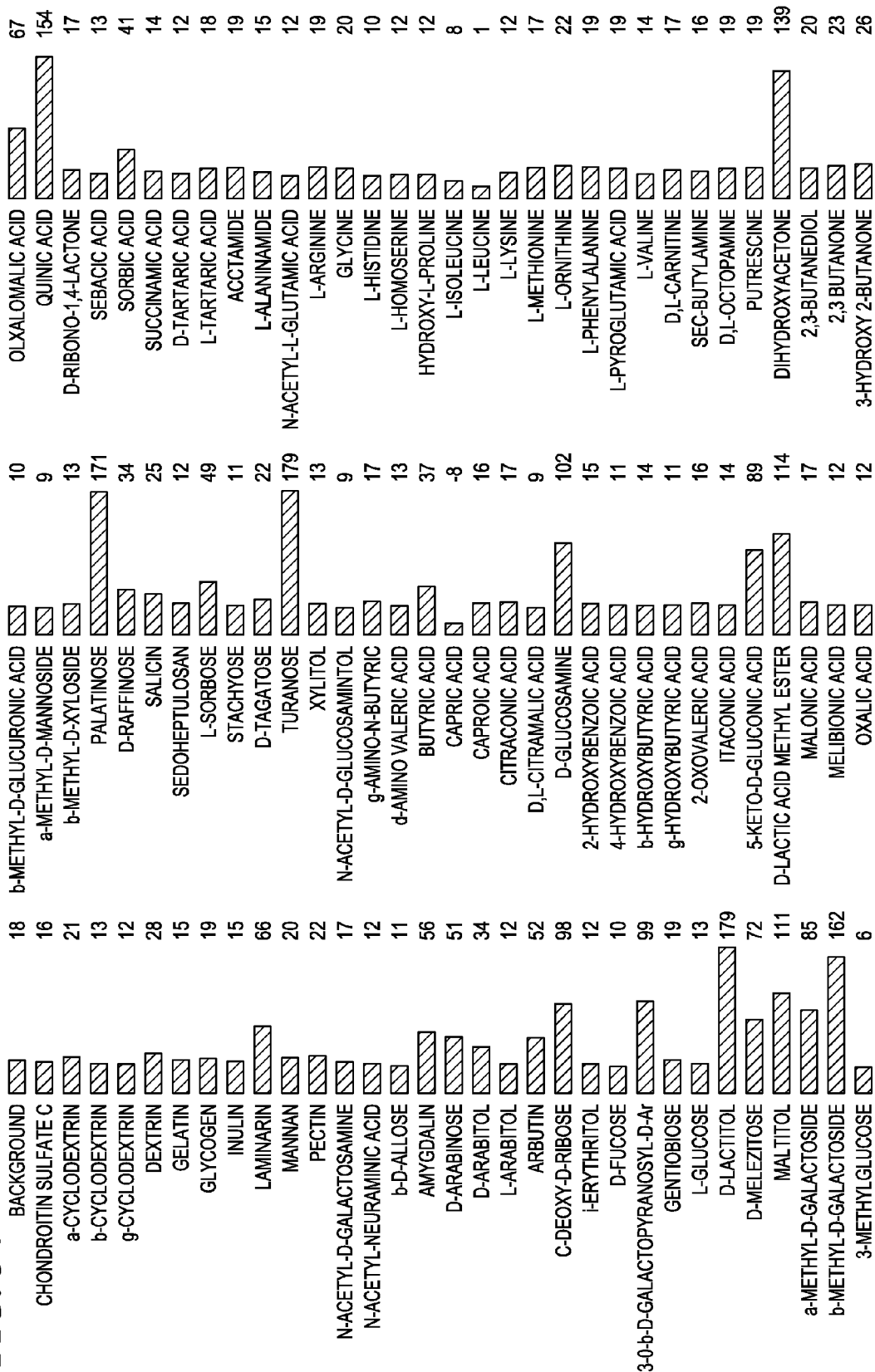
Figure 35:
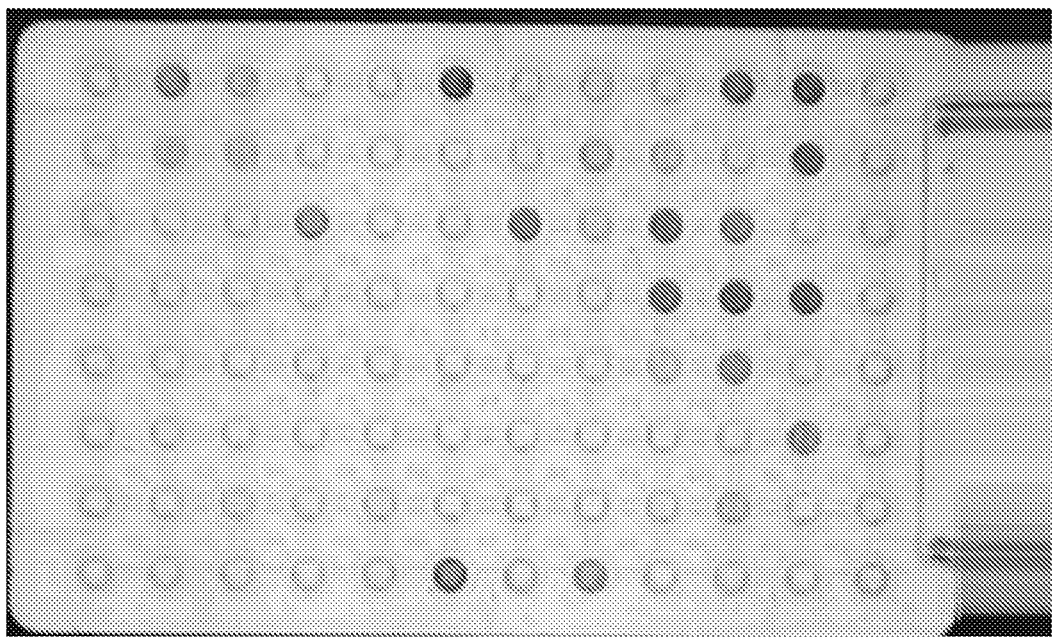
FIG. 35. PM1_1 after 5 days of incubation at 30° C.
Figure 36:
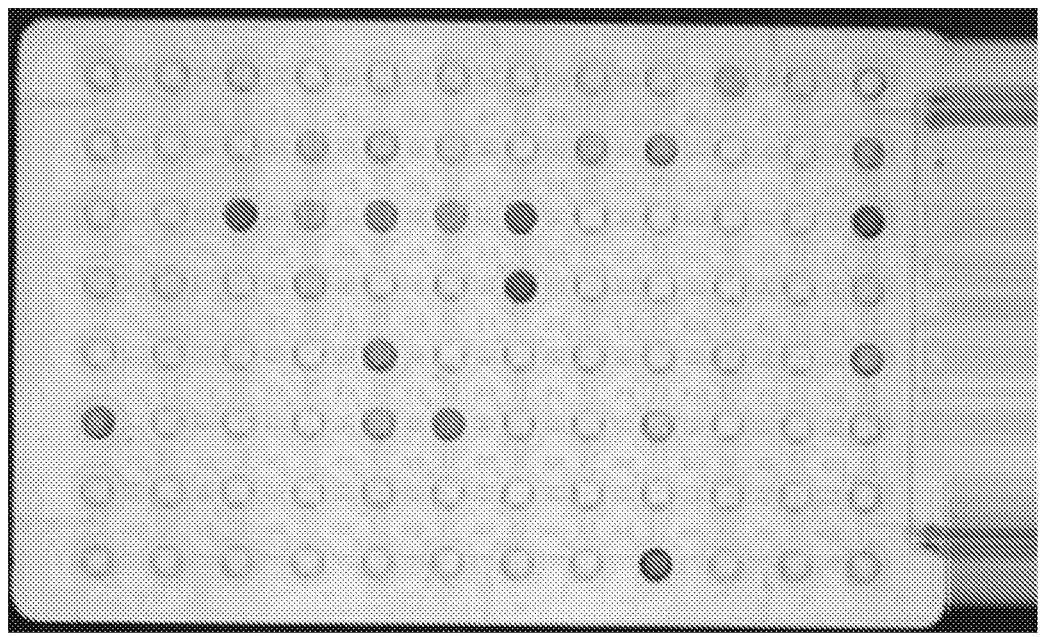
FIG. 36. PM2_2, after 6.5 days of incubation at 30° C.
Figure 37:
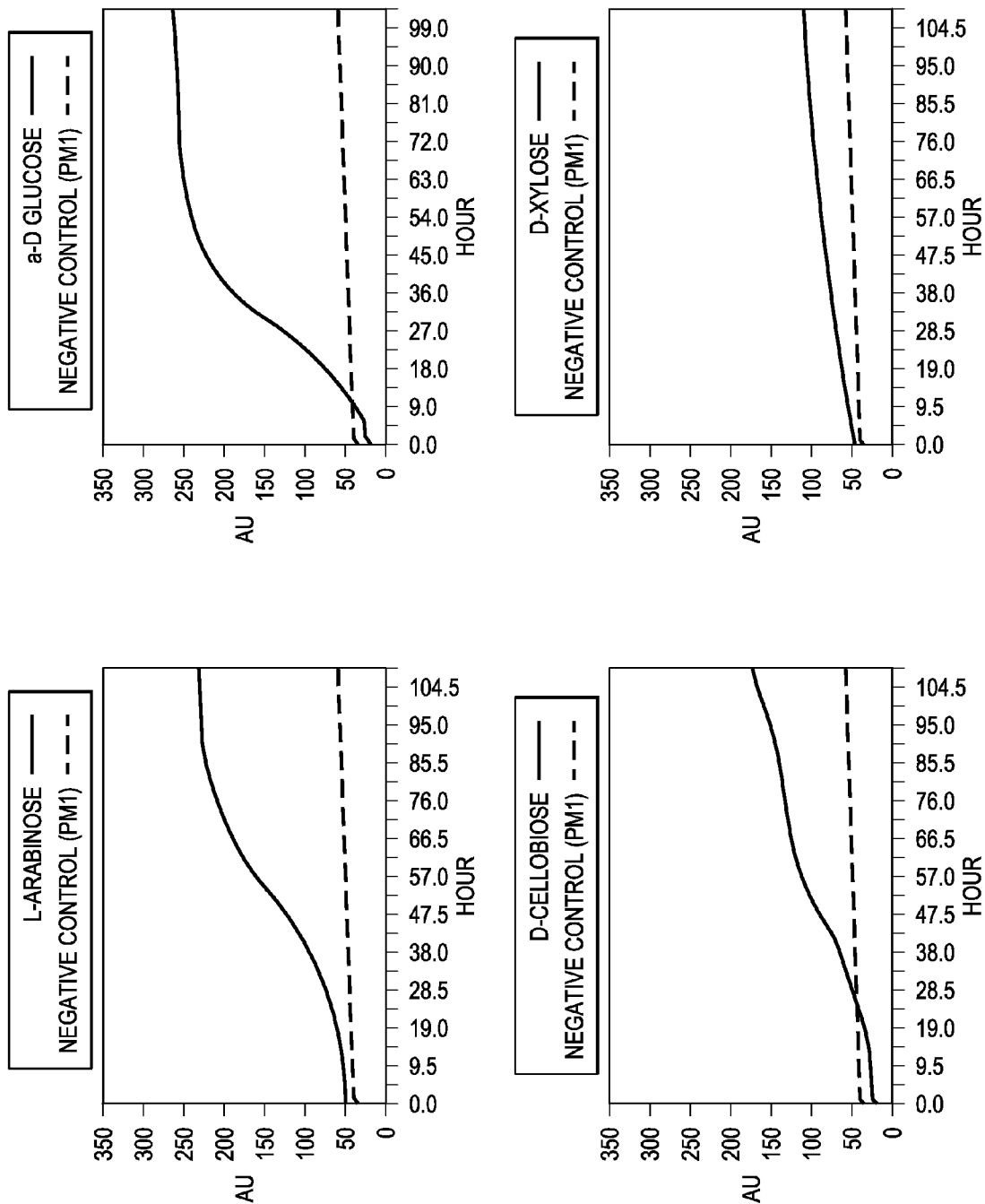
FIG. 37. Time course of *D. hansenii* growth in the presence of various carbon sources (as measured using the OMNILOG PM).
Figure 38:
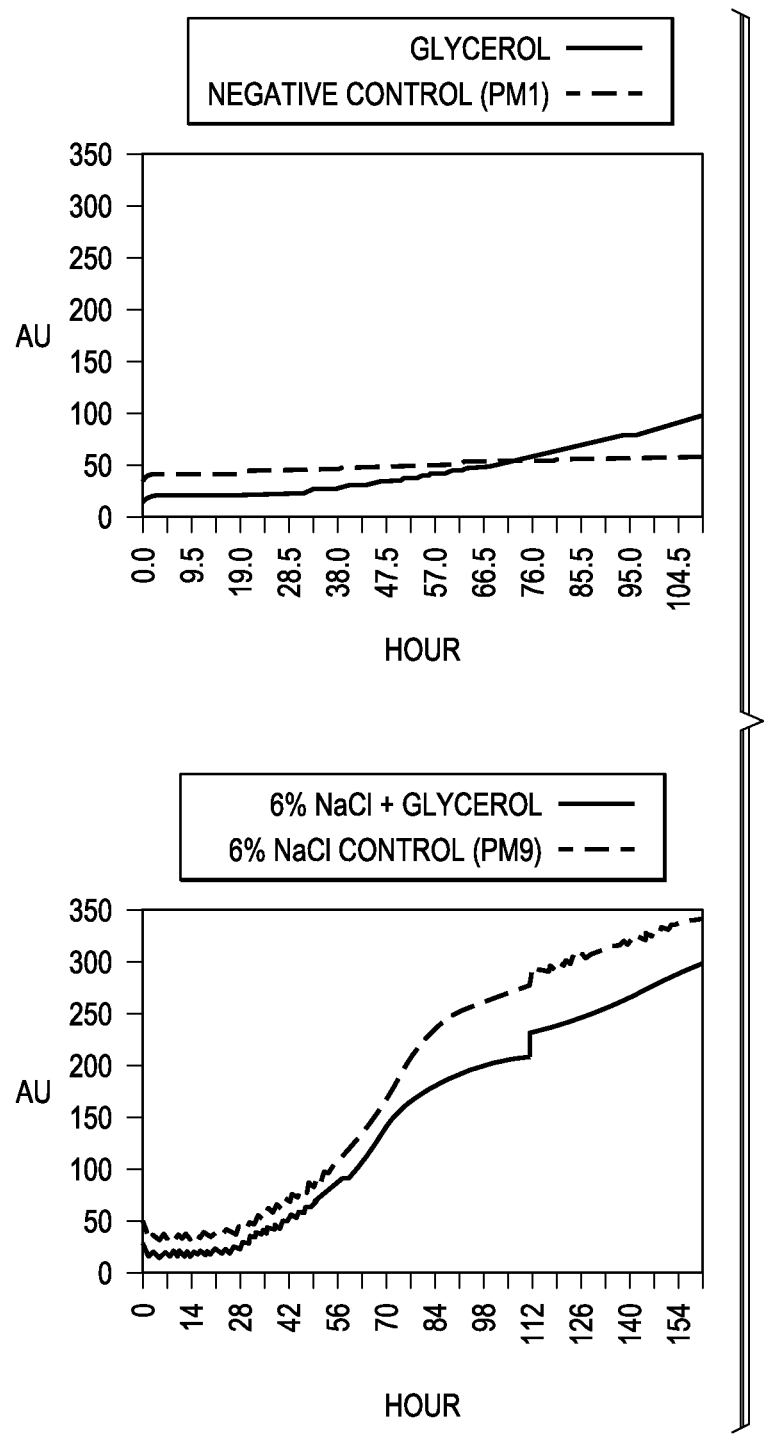
FIG. 38. Growth of *D. hansenii* in glycerol alone or with NaCl (as measured using the OMNILOG PM).
Figure 39:
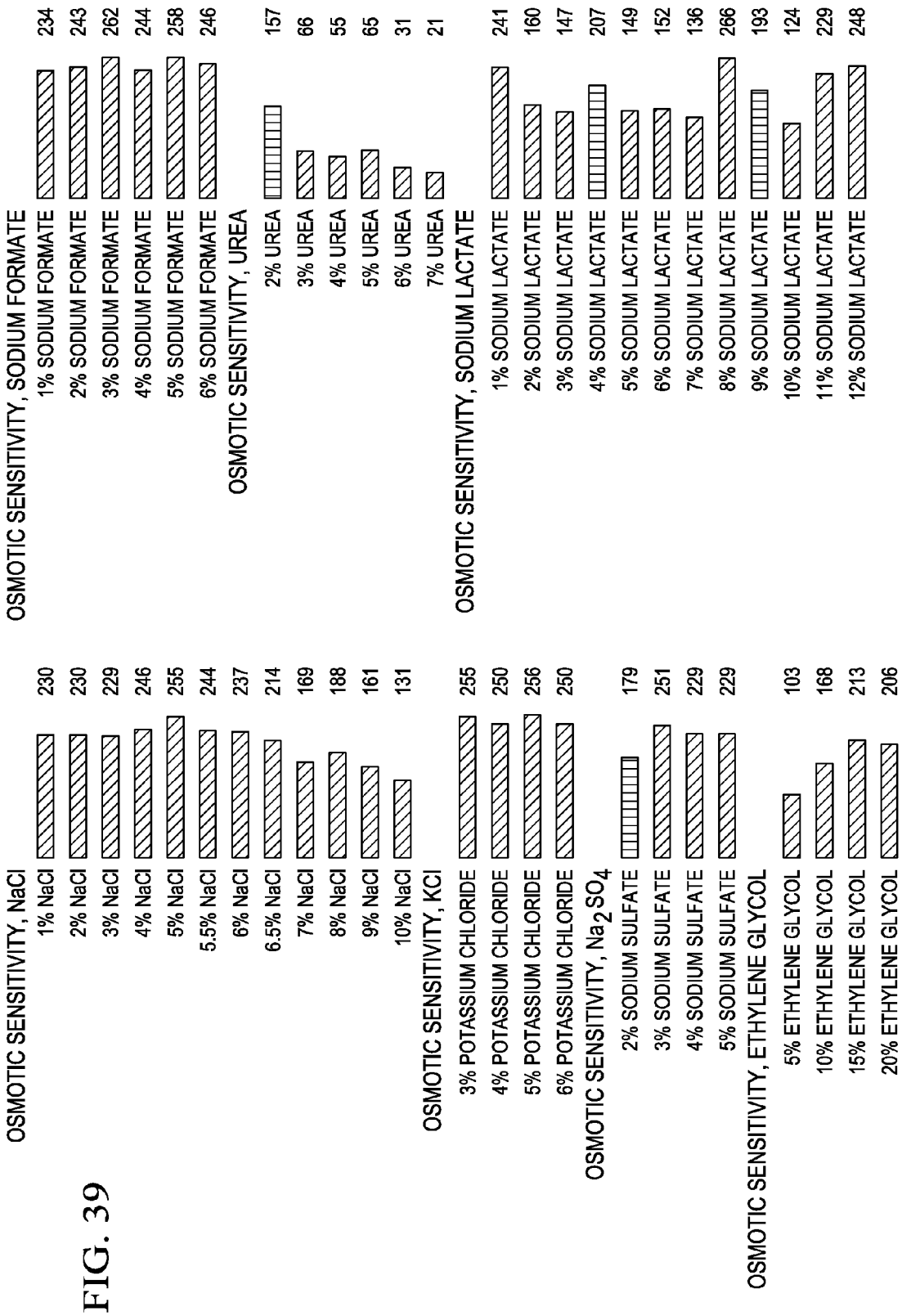
FIG. 39. Growth of *D. hansenii* in assorted osmolytes (as measured using the OMNILOG PM).
Figure 40:
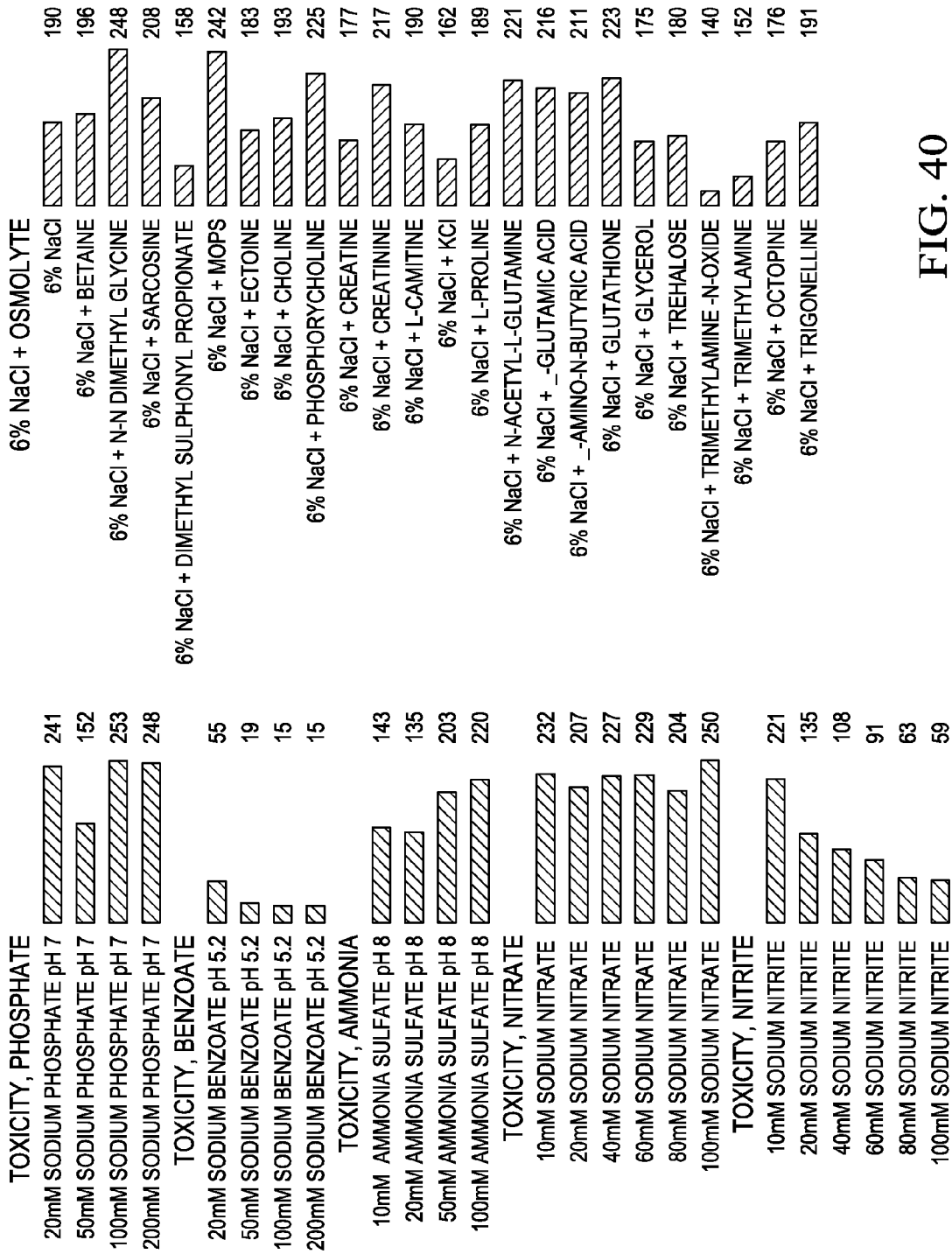
FIG. 40. Growth of *D. hansenii* in osmolytes, cont'd. (as measured using the OMNILOG PM).
Figure 41:
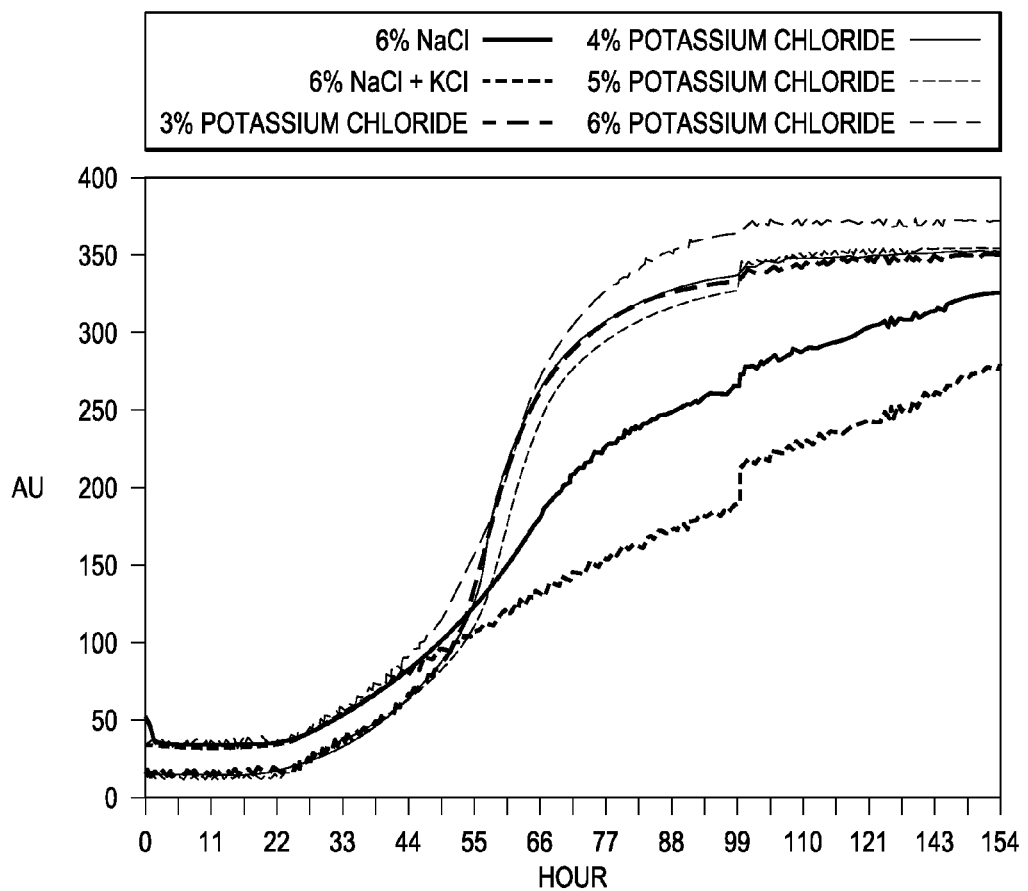
FIG. 41. Growth of *D. hansenii* in potassium chloride (as measured using the OMNILOG PM).
Figure 42:
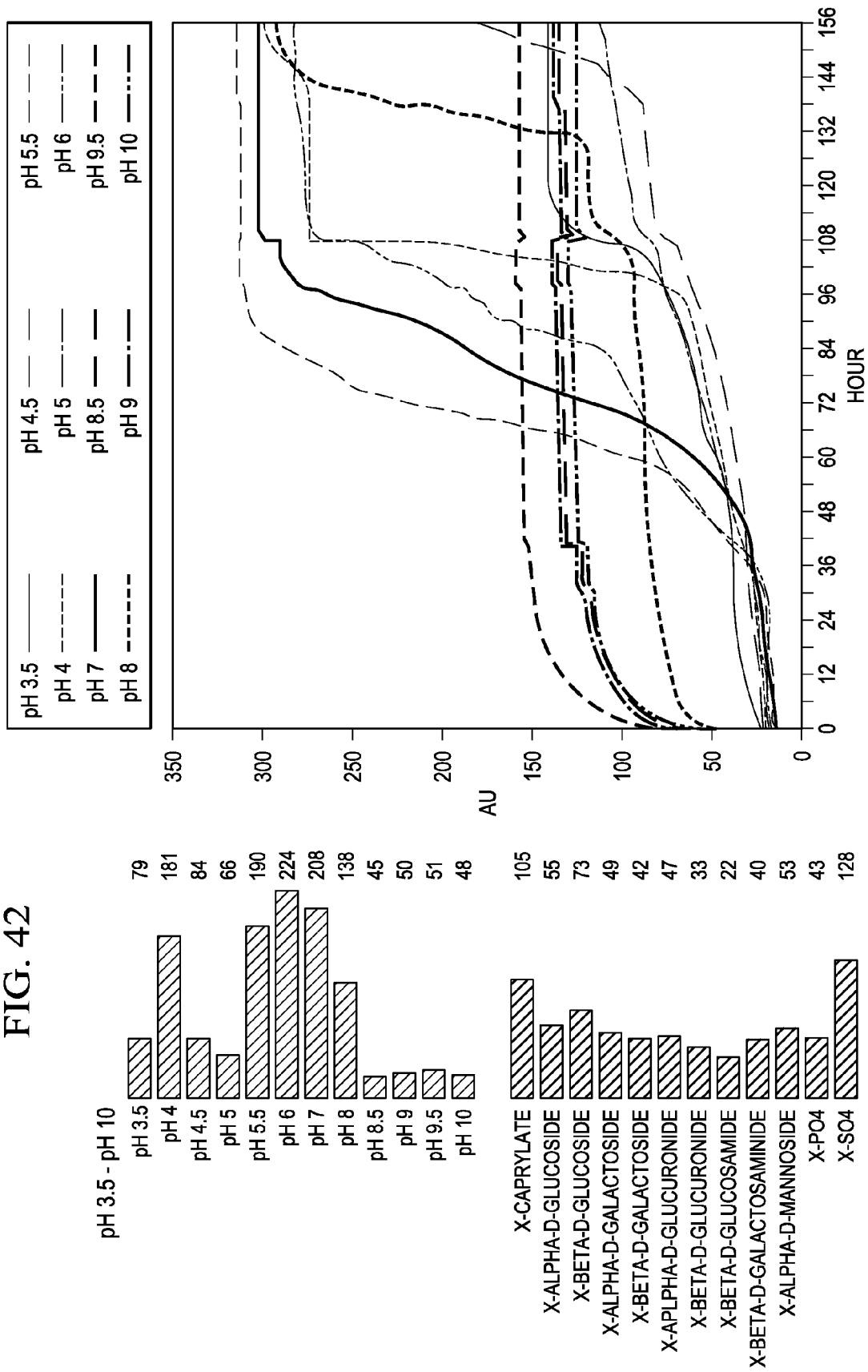
FIG. 42. Growth of *D. hansenii* at various pH values (as measured using the OMNILOG PM).
Figure 43:
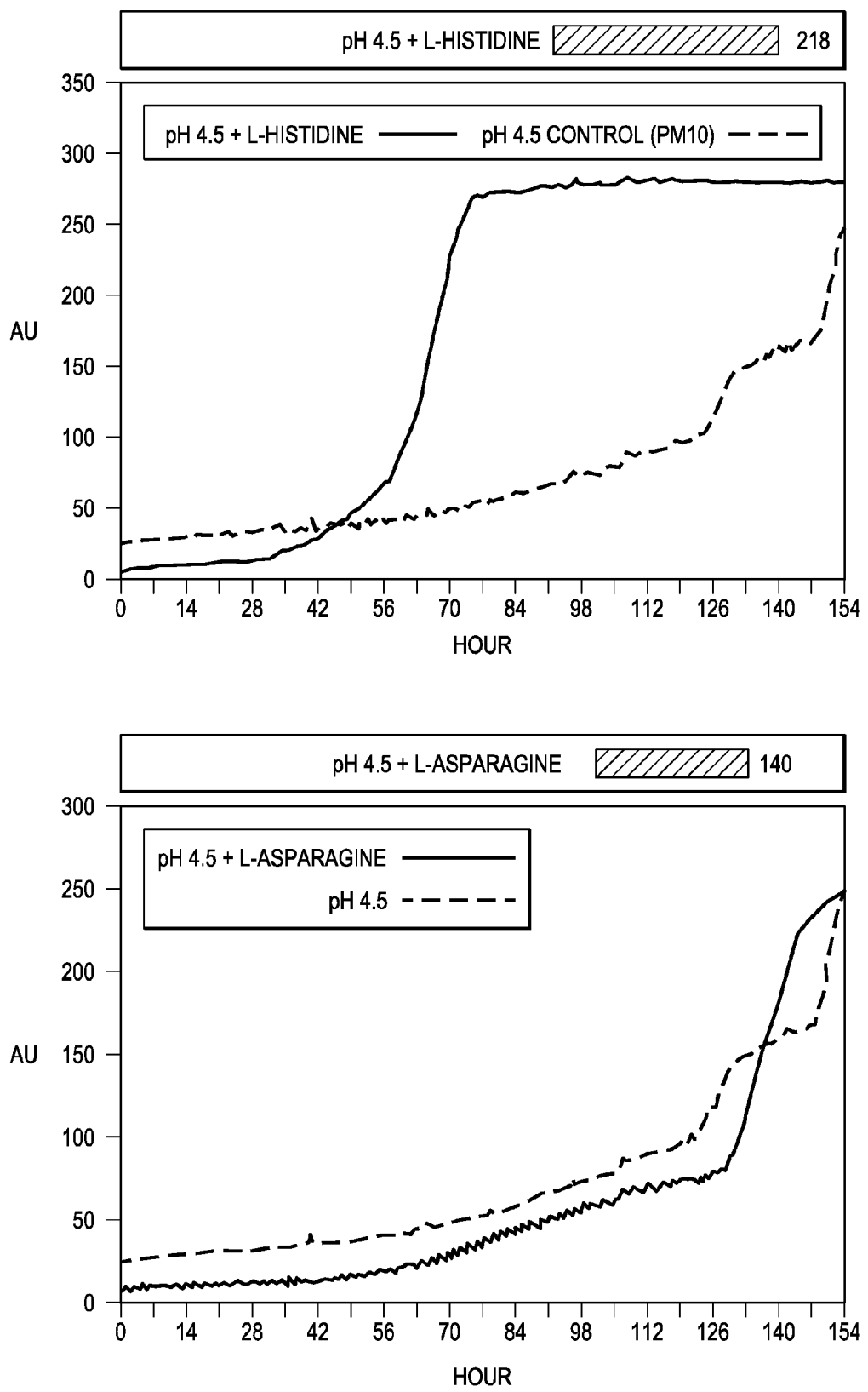
FIGS. 43 and 44. Growth of *D. hansenii* in acid and base (as measured using the OMNILOG PM).
Figure 44:
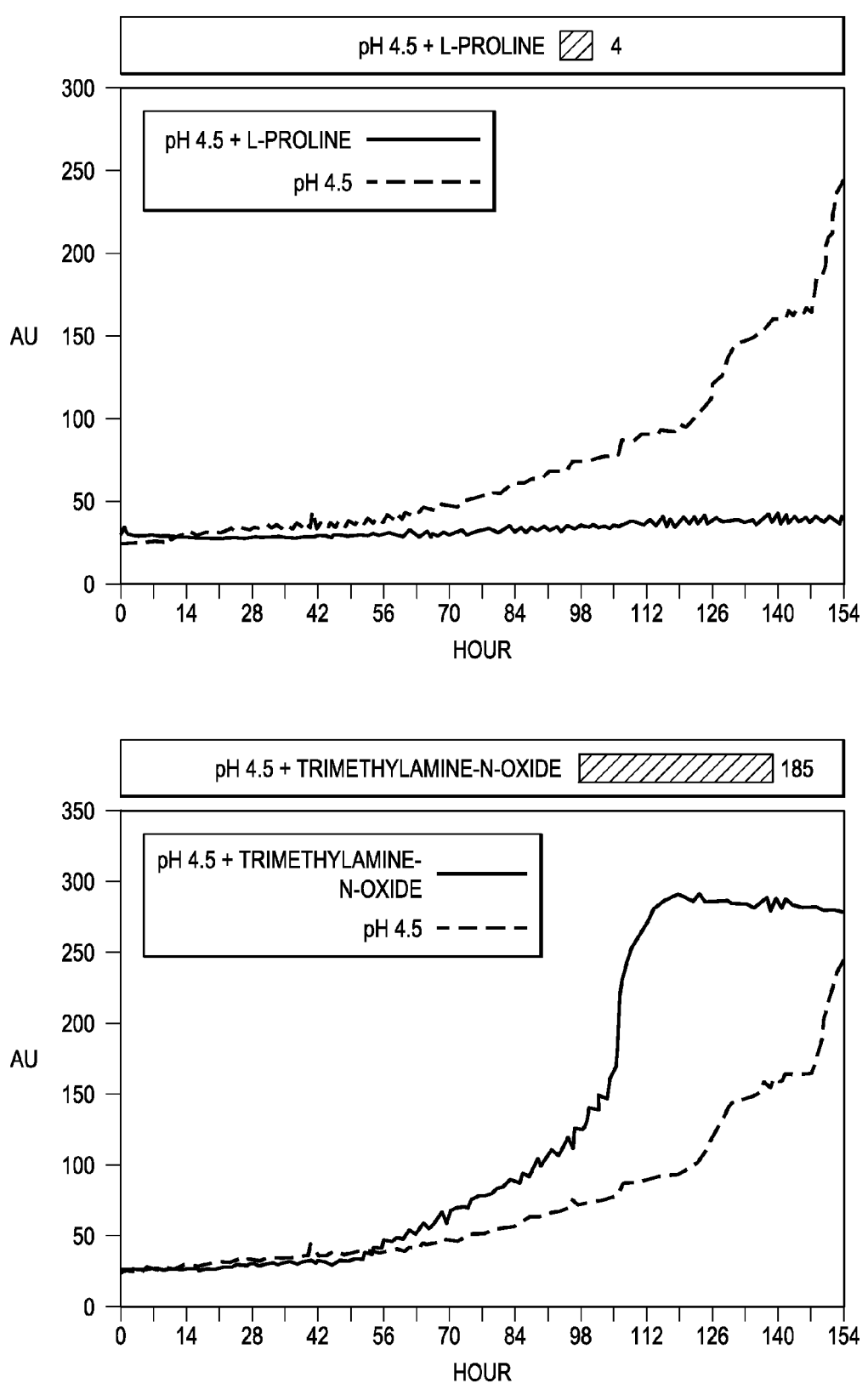

In addition to the above tested carbon sources, D. hansenii was able to efficiently utilize a variety of other pure carbon sources including various pentoses, hexoses, disaccharides and trisaccharides, (FIG. 33-38), many of which are components of plant cell wall materials. D. hansenii tolerated unfavorable growth conditions that are unsuitable for many microbial species. For examples, D. hansenii tolerated high levels of salt solutions (up to 6.5% NaCl, 6% KCl, 5% Na$_2$SO$_4$) (FIG. 39-41) without severe compromise in growth. D. hansenii also had a wider range of pH tolerance (FIG. 42-45). [FIGS. 33 and 34. Growth of D. hansenii in the presence of various carbon sources (as measured using the OMNILOG PM). FIG. 35. PM1_1 after 5 days of incubation at 30° C. FIG. 36. PM2_2, after 6.5 days of incubation at 30° C. FIG. 37. Time course of D. hansenii growth in the presence of various carbon sources (as measured using the OMNILOG PM). FIG. 38. Growth of D. hansenii in glycerol alone or with NaCl (as measured using the OMNILOG PM). FIG. 39. Growth of D. hansenii in assorted osmolytes (as measured using the OMNILOG PM). FIG. 40. Growth of D. hansenii in osmolytes, cont'd. (as measured using the OMNILOG PM). FIG. 41. Growth of D. hansenii in potassium chloride (as measured using the OMNILOG PM). FIG. 42. Growth of D. hansenii at various pH values (as measured using the OMNILOG PM). FIGS. 43 and 44. Growth of D. hansenii in acid and base (as measured using the OMNILOG PM). FIG. 45. Growth of D. hansenii at various pH values (as measured using the OMNILOG PM).

Media and reagents. Defined medium A for D. hansenii (Kimura et al., 2004) was employed. All nutrient supplements including uracil and amino acids were obtained from Sigma. The Biolog PM media contained 100 mM glucose, 1 mM disodium pyrophosphate, 2 mM sodium sulfate, 5 mM L-glutamic acid monosodium, and a proprietary tetrazolium dye mix D and IFY-0 medium. The additive sugar and salt were obtained from Sigma.

BioLog Protocol. The protocol provided by BioLog has been used on S. cerevisiae and other fungi. To apply on D. hansenii, determining the most efficient carbon substrate to optimize the protocol became the first step. According to Kimura et al., 2004, glucose or glycerol is usually used as carbon sources, and pH5.5 is the appropriate pH for D. hansenii. Since glycerol cannot be concentrated as 32× as needed, succinate that was broadly applied as carbon sources in BioLog system was used instead. The gradient concentration of glucose (50-150 mM) and succinate (10-40 mM) were tested. The inoculants lacking carbon sources were served as control.

PM assays. Inoculums for PM panels were prepared according to the manufacturer's protocols with modifications; Procedures for S. cerevisiae and other Fungi version 8 Feb. 2006 (Biolog) was used to prepare inoculums for PM01, PM02, and PM09, while version 29 Apr. 2008 (Biolog) was used for PM10. In brief, D. hansenii were streaked onto defined Medium A (Table 6) and cultivated at 30° C. for 48 hours. Cells were redistributed onto fresh agar using a sterile swab and incubated for an additional 4 hours at 30° C. to ensure active growth and avoid late-growth clumping (Oliver R Homann, Houjian Cai, 2005). (Kimura et al., 2004)

Cells were then transferred into the appropriate PM inoculation fluid (Table 7) and re-suspended to 62% transmittance (approximately 200 cells per 100 μL assay). PM1 and PM2 measure carbon source utilization and/or sensitivity; as such, the inoculation fluid lacks a defined carbon source (e.g., glycerol or glucose). In contrast, the inoculating fluids for PM9 (osmolytes) and PM10 (pH) required the inclusion of a carbon source (Table 7); in this case glucose was supplemented to 100 mM.

*D. hansenii*-containing inoculation fluid was inoculated into PM panels and incubated at 30° C. for 6.5 days. Color intensity for each well was measured every 15 minutes. Exemplary time course (kinetic) results (means) from representative PM assays are plotted.

In order to simplify the comparison of individual assay conditions, the full time-course kinetic plots were converted into a single unitless numerical value, which is weighted to more greatly value latter time points (e.g., endpoints), as described by Homann et al. (2005). Signal value=[(average signal+maximum signal)/2−average signal over first 2 h]; Represent the full time course by a single number; Weight the value towards latter time points; Subtract the "baseline" signal level for each well (Oliver R Homann, 2005) and Replicate PM assay runs were conducted, and the average of the signal values was used.

The formulation of final ingredients in PM Inoculating Fluids after the addition of cell suspension: SC medium is composed of 6.7 g of YNB without amino acid and 2 g of Synthetic Complete Supplement Mixture (SC mixture) per liter. Both YNB and SC bought from Sunrise Science.

TABLE 5

Formulation of phenotype microarray (PM) inoculation fluids for PM1, PM2, PM 9, and PM10. Note that only PM10 requires the addition of SC medium (Table 6) (Sunrise Science).

| PM5,9 (mM) | Ingredient | PM10+ (mM) |
|---|---|---|
| 1× | IFY-0 | — |
| — | SC Medium | 1× |
| 1× | Dye mix D | — |
| — | Dye mix E | 1× |
| 100 | D-glucose | 100 |
| 5 | L-glutamic acid monosodium | — |
| 1 | potassium phosphate [pH 6.0] | — |
| 2 | sodium sulfate | — |
| 0.05 | adenine HCl$^a$ | 0.05 |
| 0.01 | L-histidine HCl monohydrate$^a$ | 0.01 |
| 0.1 | L-leucine$^a$ | 0.1 |
| 0.05 | L-lysine HCl$^a$ | 0.05 |
| 0.025 | L-methionine$^a$ | 0.025 |
| 0.025 | L-tryptophan$^a$ | 0.025 |
| 0.03 | uracil$^a$ | 0.03 |

TABLE 6

The formulation of SC Medium (Sunrise Science).

| Component in SC Mixture | mg/L |
|---|---|
| Adenine | 21 |
| L-Alanine | 85.6 |
| L-Arginine | 85.6 |
| L-Asparagine | 85.6 |
| L-Aspartic Acid | 85.6 |
| L-Cysteine | 85.6 |
| Glutamine | 85.6 |
| L-Glutamic Acid | 85.6 |
| Glycine | 85.6 |
| L-Histidine | 85.6 |
| Myo-Inositol | 85.6 |
| L-Isoleucine | 85.6 |
| L-Leucine | 173.4 |
| Para-AminoBenzoic Acid (PABA) | 8.6 |
| L-Methionine | 85.6 |
| L-Lysine | 85.6 |
| L-Phenylalenine | 85.6 |
| L-Proline | 85.6 |
| L-Serine | 85.6 |
| L-Threonine | 85.6 |
| L-Tyrptophan | 85.6 |
| L-Tyrosine | 85.6 |
| Uracil | 85.6 |
| L-Valine | 85.6 |

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrequited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

[1] Mabee, W. E., Policy options to support biofuel production. Adv Biochem Eng Biotechnol 2007, 108, 329-357.
[2] Otero, J. M., Panagiotou, G., Olsson, L., Fueling industrial biotechnology growth with bioethanol. Adv Biochem Eng Biotechnol 2007, 108, 1-40.
[3] Balat, M., Global bio-fuel processing and production trends. Energy Exploration & Exploitation 2007, 25, 195-218.
[4] Charles, M., Ryan, R., Oloruntoba, R., Public policy and biofuels: The way forward. Energy Policy 2007, 35, 5737-5746.
[5] Hillring, B., Rural development and bioenergy-experience from 20 years of development in Sweden. Biomass and Bioenergy 2002, 23, 443-451.
[6] Prasad, G., The role of biomass in rural development. Global Network of Energy for Sustainable Development 2004, 1-57.
[7] Gmyrek, R., The time of biofuels and three "E"—energy, ecology, economy. Przemysl Chemiczny 2006, 85, 1560-1567.
[8] Mabee, W. E., Policy options to support biofuel production. Biofuels 2007, 108, 329-357.
[9] Kulczycki, A., The role of scientific research in the development of biofuels. Przemysl Chemiczny 2006, 85, 1576-1578.
[10] Pagliaro, M., Ciriminna, R., Kimura, H., Rossi, M., Della Pina, C., From glycerol to value-added products. Angew Chem Int Ed Engl 2007, 46, 4434-4440.
[11] Ranganathan, S. V., Narasimhan, S. L., Muthukumar, K., An overview of enzymatic production of biodiesel. Bioresour Technol 2007.
[12] Dharmadi, Y., Murarka, A., Gonzalez, R., Anaerobic fermentation of glycerol by *Escherichia coli*: a new platform for metabolic engineering. Biotechnol Bioeng 2006, 94, 821-829.
[13] Murarka, A., Dharmadi, Y., Yazdani, S. S., Gonzalez, R., Fermentative utilization of glycerol by *Escherichia coli* and its implications for the production of fuels and chemicals. Appl Environ Microbiol 2008, 74, 1124-1135.
[14] Sakai, S., Yagishita, T., Microbial production of hydrogen and ethanol from glycerol-containing wastes discharged from a biodiesel fuel production plant in a bioelectrochemical reactor with thionine. Biotechnol Bioeng 2007, 98, 340-348.
[15] Wang, Z. X., Zhuge, J., Fang, H., Prior, B. A., Glycerol production by microbial fermentation: a review. Biotechnol Adv 2001, 19, 201-223.
[16] Breuer, U., Harms, H., *Debaryomyces hansenii*—an extremophilic yeast with biotechnological potential. Yeast 2006, 23, 415-437.
[17] Breuer, U., Harms, H., *Debaryomyces hansenii*—an extremophilic yeast with biotechnological potential. Yeast 2006, 23, 415-437.
[18] Alvarez, H. M., Steinbuchel, A., Triacylglycerols in prokaryotic microorganisms. Appl Microbiol Biotechnol 2002, 60, 367-376.
[19] Leman, J., Oleaginous microorganisms: an assessment of the potential. Adv Appl Microbiol 1997, 43, 195-243.
[20] Ratledge, C., Regulation of lipid accumulation in oleaginous micro-organisms. Biochem Soc Trans 2002, 30, 1047-1050.
[21] Ratledge, C., Fatty acid biosynthesis in microorganisms being used for Single Cell Oil production. Biochimie 2004, 86, 807-815.
[22] Dai, C. C., Tao, J., Xie, F., Dai, Y. J., Zhao, M., Biodiesel generation from oleaginous yeast *Rhodotorula glutinis* with xylose assimilating capacity. African Journal of Biotechnology 2007, 6, 2130-2134.
[23] Chisti, Y., Biodiesel from microalgae. Biotechnol Adv 2007, 25, 294-306.
[24] Gangar, a., Raychaudhuri, S., Rajasekharan, R., Alteration in the cytosolic triacylglycerol biosynthetic machinery leads to decreased cell growth and triacylglycerol synthesis in oleaginous yeast. Biochemical Journal 2002, 365, 577-589.
[25] Ratledge, C., Wynn, J. P., The biochemistry and molecular biology of lipid accumulation in oleaginous microorganisms. Adv Appl Microbiol 2002, 51, 1-51.
[26] Granger, L. M., Perlot, P., Goma, G., Pareilleux, a., Efficiency of Fatty-Acid Synthesis by Oleaginous Yeasts—Prediction of Yield and Fatty-Acid Cell Content from Consumed C/N Ratio by a Simple Method. Biotechnology and Bioengineering 1993, 42, 1151-1156.
[27] Granger, L. M., Perlot, P., Goma, G., Pareilleux, a., Effect of Various Nutrient Limitations on Fatty-Acid Production by *Rhodotorula*-Glutinis. Applied Microbiology and Biotechnology 1993, 38, 784-789.
[28] Meesters, P. A. E. P., Huijberts, G. N. M., Eggink, G., High cell density cultivation of the lipid accumulating yeast *Cryptococcus curvatus* using glycerol as a carbon source. Applied Microbiology and Biotechnology 1996, 45, 575-579.
[29] Meesters, P. A. E. P., vanderWal, H., Weusthuis, R., Eggink, G., Cultivation of the oleaginous yeast *Cryptococcus curvatus* in a new reactor with improved mixing and mass transfer characteristics (Surer(R)). Biotechnology Techniques 1996, 10, 277-282.
[30] PAN, J. G., Rhee, J. S., Kinetic and Energetic Analyses of Lipid-Accumulation in Batch Culture of *Rhodotorula-Glutinis*. Journal of Fermentation Technology 1986, 64, 557-560.
[31] PAN, J. G., Rhee, J. S., Biomass Yields and Energetic Yields of Oleaginous Yeasts in Batch Culture. Biotechnology and Bioengineering 1986, 28, 112-114.
[32] Adams, I. P., Dack, S., Dickinson, F. M., Midgley, M., Ratledge, C., ATP: citrate lyase from *Aspergillus nidulans*. Biochem Soc Trans 1997, 25, 5670.
[33] Wynn, J. P., Hamid, A. A., Li, Y., Ratledge, C., Biochemical events leading to the diversion of carbon into storage lipids in the oleaginous fungi *Mucor circinelloides* and *Mortierella alpina*. Microbiology 2001, 147, 2857-2864.

[34] Evans, C. T., Ratledge, C., Biochemical activities during lipid accumulation in *Candida curvata*. Lipids 1983, 18, 630-635.

[35] Evans, C. T., Ratledge, C., A comparison of the oleaginous yeast, *Candida curvata*, grown on different carbon sources in continuous and batch culture. Lipids 1983, 18, 623-629.

[36] Hassan, M., Blanc, P. J., Granger, L. M., Pareilleux, A., Goma, G., Influence of nitrogen and iron limitations on lipid production by *Cryptococcus curvatus* grown in batch and fed-batch culture. Process Biochemistry 1996, 31, 355-361.

[37] Merdinger, E., Devine, E. M., Jr., Lipids Of *Debaryomyces hansenii*. J Bacteriol 1965, 89, 1488-1493.

[38] Coleman, R. a., Lee, D. P., Enzymes of triacylglycerol synthesis and their regulation. Progress in Lipid Research 2004, 43, 134-176.

[39] Sorger, D., Daum, G., Triacylglycerol biosynthesis in yeast. Applied Microbiology and Biotechnology 2003, 61, 289-299.

[40] Dyal, S. D., Narine, S. S., Implications for the use of *Mortierella* fungi in the industrial production of essential fatty acids. Food Research International 2005, 38, 445-467.

[41] Sattur, a. P., Karanth, N. G., Production of Microbial Lipids by Oleaginous Yeasts—a Review. Journal of Microbial Biotechnology 1988, 3, 51-63.

[42] Ratledge, C., Gilbert, S. C., Carnitine Acetyltransferase Activity in Oleaginous Yeasts. Ferns Microbiology Letters 1985, 27, 273-275.

[43] Ladygina, N., Dedyukhina, E. G., Vainshtein, M. B., A review on microbial synthesis of hydrocarbons. Process Biochemistry 2006, 41, 1001-1014.

[44] Merdinge. E, Devine, E. M., Lipids of *Debaryomyces hansenii*. Journal of Bacteriology 1965, 89, 1488-&.

[45] Ricaurte, M. L., Govind, N. S., Construction of Plasmid Vectors and Transformation of the Marine Yeast *Debaryomyces hansenii*. Mar Biotechnol (NY) 1999, 1, 15-19.

[46] Maggi, R. G., Govind, N. S., Regulated expression of green fluorescent protein in *Debaryomyces hansenii*. Journal of Industrial Microbiology & Biotechnology 2004, 31, 301-310.

[47] Prista, C., Loureiro-Dias, M. C., Montiel, V., Garcia, R., Ramos, J., Mechanisms underlying the halotolerant way of *Debaryomyces hansenii*. FEMS Yeast Res 2005, 5, 693-701.

[48] Butinar, L., Santos, S., Spencer-Martins, I., Oren, A., Gunde-Cimerman, N., Yeast diversity in hypersaline habitats. FEMS Microbiol Lett 2005, 244, 229-234.

[49] Olofsson, S. O., Bostrom, P., Andersson, L., Rutberg, M., et al., Triglyceride containing lipid droplets and lipid droplet-associated proteins. Curr Opin Lipidol 2008, 19, 441-447.

[50] Goodman, J. M., The gregarious lipid droplet. J Biol Chem 2008, 283, 28005-28009.

[51] Thiele, C., Spandl, J., Cell biology of lipid droplets. Curr Opin Cell Biol 2008, 20, 378-385.

[52] Fujimoto, T., Ohsaki, Y., Cheng, J., Suzuki, M., Shinohara, Y., Lipid droplets: a classic organelle with new outfits. Histochem Cell Biol 2008, 130, 263-279.

[53] Greenberg, A. S., Obin, M. S., Many roads lead to the lipid droplet. Cell Metab 2008, 7, 472-473.

[54] Benado, A., Nasagi-Atiya, Y., Sagi-Eisenberg, R., Protein trafficking in immune cells. Immunobiology 2009, 214, 403-421.

[55] Kreft, M., Potokar, M., Stenovec, M., Pangrsic, T., Zorec, R., Regulated exocytosis and vesicle trafficking in astrocytes. Ann N Y Acad Sci 2009, 1152, 30-42.

[56] Nedvetsky, P. I., Tamma, G., Beulshausen, S., Valenti, G., et al., Regulation of aquaporin-2 trafficking. Handb Exp Pharmacol 2009, 133-157.

[57] Storrie, B., Starr, T., Forsten-Williams, K., Using quantitative fluorescence microscopy to probe organelle assembly and membrane trafficking. Methods Mol Biol 2008, 457, 179-192.

[58] Braulke, T., Bonifacino, J. S., Sorting of lysosomal proteins. Biochim Biophys Acta 2009, 1793, 605-614.

[59] Nathan, J. A., Lehner, P. J., The trafficking and regulation of membrane receptors by the RING-CH ubiquitin E3 ligases. Exp Cell Res 2009, 315, 1593-1600.

[60] Alvers, A. L., Fishwick, L. K., Wood, M. S., Hu, D., et al., Autophagy and amino acid homeostasis are required for chronological longevity in *Saccharomyces cerevisiae*. Aging Cell 2009.

[61] Camougrand, N., Kissova, I., Salin, B., Devenish, R. J., Monitoring mitophagy in yeast. Methods Enzymol 2008, 451, 89-107.

[62] Noda, T., Viability assays to monitor yeast autophagy. Methods Enzymol 2008, 451, 27-32.

[63] Chen, C. N., Chen, H. R., Yeh, S. Y., Vittore, G., Ho, T. H., Autophagy is enhanced and floral development is impaired in AtHVA22d RNA interference *Arabidopsis*. Plant Physiol 2009, 149, 1679-1689.

[64] Longatti, A., Tooze, S. A., Vesicular trafficking and autophagosome formation. Cell Death Differ 2009, 16, 956-965.

[65] Kraft, C., Reggiori, F., Peter, M., Selective types of autophagy in yeast. Biochim Biophys Acta 2009.

[66] Noda, N. N., Ohsumi, Y., Inagaki, F., ATG systems from the protein structural point of view. Chem Rev 2009, 109, 1587-1598.

[67] Kourtis, N., Tavernarakis, N., Autophagy and cell death in model organisms. Cell Death Differ 2009, 16, 21-30.

[68] Pollack, J. K., Harris, S. D., Marten, M. R., Autophagy in filamentous fungi. Fungal Genet Biol 2009, 46, 1-8.

[69] Li, S. C., Kane, P. M., The yeast lysosome-like vacuole: endpoint and crossroads. Biochim Biophys Acta 2009, 1793, 650-663.

[70] Homann et al. 2005. Harnessing natural diversity to probe metabolic pathways. PLoS Genetics 1:715-729.

What is claimed is:

1. A method of making a biofuel comprising:
obtaining a sugarcane bagasse biomass and an isolated oleaginous microbe; and
mixing the sugarcane bagasse biomass and the oleaginous microbe in a nitrogen-limiting minimal growth media comprising glycerol, or glucose generated from the sugarcane bagasse biomass, under conditions in which an oleaginous microbe converts the growth media into a triacylglycerol (TAG), wherein the oleaginous microbe overexpress Autophagy Protein ATG8.

2. The method of claim 1, wherein the microbe secretes TAG.

3. The method of claim 1, wherein the minimal growth media further comprises 0.5, 1.0, 1.5, or 2.0 M salt.

4. The method of claim 1, wherein the minimal growth media is defined further as comprising a source of glucose selected from at least one of a cellulose, a cellulosic substrate, cellobiose, carboxymethylcellulose, hemicellulose, a sweet sorghum extract, a sugar cane extract, a sugar cane, or cellulosic substrates derived therefrom.

5. The method of claim 1, wherein the TAG further comprises oleic acid at the Sn-1, Sn-2 or Sn-3 position.

6. The method of claim 1, wherein the oleaginous microbes are grown for 48, 72, 96, or 120 hours at a temperature of 25° C., 30° C., or 37° C. and at a pH of 5.0, 5.5, 6.0, 6.5, 7.0 or 7.5.

7. The method of claim 1, wherein the minimal growth media further comprises 0.1% by weight nitrogen.

8. The method of claim 1, wherein the oleaginous microbes secrete the triacylglycerol, without cell death.

9. The method of claim 1, wherein the oleaginous microbes are induced to overexpress Autophagy Protein ATG8.

10. The method of claim 1, wherein the oleaginous microbes are genetically modified to overexpress Autophagy Protein ATG8.

11. The method of claim 10, wherein the overexpressed Autophagy Protein ATG8 is integrated into the genome of the oleaginous microbes or expressed by an autonomously replicating plasmid.

12. The method of claim 1, wherein the oleaginous microbe is *Debaryomyces* sp.

13. A method of producing a biofuel comprising:
   obtaining a cellulosic biomass and an isolated oleaginous microbe; and
   growing the oleaginous microbe in a nitrogen-limiting minimal media to late log phase and/or stationary phase, whereby the oleaginous microbe secretes an oil, wherein the oleaginous microbe overexpress Autophagy Protein ATG8.

14. The method of claim 13, wherein the minimal growth media further comprises 0.1% by weight nitrogen.

15. The method of claim 13, wherein the oleaginous microbe is grown for 48, 72, 96, or 120 hours at a temperature of 25° C., 30° C., or 37° C. and at a pH of 5.0, 5.5, 6.0, 6.5, 7.0 or 7.5.

16. The method of claim 13, wherein the minimal growth media further comprises 0.5, 1.0, 1.5, or 2.0M salt.

17. The method of claim 13, wherein the minimal growth media further comprises salt that is at least one of NaCl, KCl, or both KCl and NaCl.

18. The method of claim 13, wherein the oleaginous microbe is disrupted by mechanical or chemical treatment to release intracellular oils.

19. A method of reducing bioreactor waste comprising:
   obtaining a cellulosic biomass and isolated *Debaryomyces hansenii*; and
   mixing a reaction waste product comprising glycerol with a growth media and an inoculum of *Debaryomyces hansenii* under conditions in which *Debaryomyces hansenii* converts the glycerol into TAG comprising oleic acid at the Sn-1, Sn-2 or Sn-3 position; and
   recovering the TAG comprising oleic acid at the Sn-1, Sn-2 or Sn-3 position produced thereby, wherein the oleaginous microbe overexpress Autophagy Protein ATG8.

20. A method of reducing bioreactor waste comprising
   generating a biofuel by fermentation;
   collecting a glycerol waste stream from the fermentation;
   mixing a biofuel reactor waste product comprising glycerol with a growth media and an inoculum of *Debaryomyces hansenii* under conditions in which *Debaryomyces hansenii* converts the glycerol into TAG comprising oleic acid at the Sn-1, Sn-2 or Sn-3 position; and
   recovering the TAG comprising oleic acid at the Sn-1, Sn-2 or Sn-3 position produced thereby, wherein the oleaginous microbe overexpress Autophagy Protein ATG8.

* * * * *